US009790219B2

(12) United States Patent
Bastos et al.

(10) Patent No.: US 9,790,219 B2
(45) Date of Patent: Oct. 17, 2017

(54) COMPOUNDS, COMPOSITIONS, AND METHODS FOR INCREASING CFTR ACTIVITY

(71) Applicant: Proteostasis Therapeutics, Inc., Cambridge, MA (US)

(72) Inventors: Cecilia M. Bastos, South Grafton, MA (US); Benito Munoz, Newtonville, MA (US); Bradley Tait, Malden, MA (US)

(73) Assignee: Proteostasis Therapeutics, Inc., Cambridge, MA (US)

( * ) Notice: Subject to any disclaimer, the term of this patent is extended or adjusted under 35 U.S.C. 154(b) by 0 days.

(21) Appl. No.: 15/125,827

(22) PCT Filed: Mar. 13, 2015

(86) PCT No.: PCT/US2015/020460
§ 371 (c)(1),
(2) Date: Sep. 13, 2016

(87) PCT Pub. No.: WO2015/138909
PCT Pub. Date: Sep. 17, 2015

(65) Prior Publication Data
US 2017/0001993 A1   Jan. 5, 2017

Related U.S. Application Data

(60) Provisional application No. 62/102,199, filed on Jan. 12, 2015, provisional application No. 62/096,413, filed on Dec. 23, 2014, provisional application No. 61/952,551, filed on Mar. 13, 2014.

(51) Int. Cl.
| | | |
|---|---|---|
| C07D 417/12 | (2006.01) | |
| A61K 31/433 | (2006.01) | |
| A61K 31/4245 | (2006.01) | |
| C07D 413/12 | (2006.01) | |
| A61K 45/06 | (2006.01) | |
| A61K 31/404 | (2006.01) | |
| A61K 31/443 | (2006.01) | |
| A61K 31/47 | (2006.01) | |

(52) U.S. Cl.
CPC .......... *C07D 417/12* (2013.01); *A61K 31/404* (2013.01); *A61K 31/4245* (2013.01); *A61K 31/433* (2013.01); *A61K 31/443* (2013.01); *A61K 31/47* (2013.01); *A61K 45/06* (2013.01); *C07D 413/12* (2013.01)

(58) Field of Classification Search
None
See application file for complete search history.

(56) References Cited

U.S. PATENT DOCUMENTS

| | | |
|---|---|---|
| 5,780,393 A | 7/1998 | Newton |
| 5,888,941 A | 3/1999 | Bartroli et al. |
| 7,846,951 B2 | 12/2010 | Miller et al. |
| 7,915,297 B2 | 3/2011 | Cho et al. |
| 7,981,935 B2 | 7/2011 | Olson et al. |
| 8,193,225 B2 | 6/2012 | Schneider et al. |
| 8,236,838 B2 | 8/2012 | Jones et al. |
| 8,623,860 B2 | 1/2014 | Fleck et al. |
| 8,815,924 B2 | 8/2014 | Dorsch et al. |
| 2006/0041006 A1 | 2/2006 | Ibrahim et al. |
| 2006/0100226 A1 | 5/2006 | Sikorski et al. |
| 2008/0090882 A1 | 4/2008 | Dorsch et al. |
| 2009/0069288 A1 | 3/2009 | Breinlinger et al. |
| 2009/0163545 A1 | 6/2009 | Goldfarb |
| 2009/0264486 A1 | 10/2009 | Jones et al. |
| 2009/0318429 A1 | 12/2009 | Doyle et al. |
| 2010/0234367 A1 | 9/2010 | Nomura et al. |
| 2011/0003784 A1 | 1/2011 | Garvey et al. |
| 2011/0082181 A1 | 4/2011 | Seiders et al. |
| 2011/0212975 A1 | 9/2011 | Kao et al. |
| 2012/0095002 A1 | 4/2012 | Ratcliffe et al. |
| 2012/0264738 A1 | 10/2012 | Sugimoto et al. |
| 2013/0217883 A1 | 8/2013 | Adaway |
| 2013/0237502 A1 | 9/2013 | Curtis et al. |
| 2014/0364467 A1 | 12/2014 | Schneider et al. |
| 2016/0151335 A1 | 6/2016 | Tait et al. |
| 2017/0001991 A1 | 1/2017 | Bastos et al. |
| 2017/0001993 A1 | 1/2017 | Bastos et al. |

FOREIGN PATENT DOCUMENTS

| | | |
|---|---|---|
| CA | 2736441 A1 | 10/2012 |
| EP | 0337263 A2 | 10/1989 |
| EP | 0957099 A2 | 11/1999 |
| JP | 2006176443 A | 7/2006 |
| WO | WO-0200651 A2 | 1/2002 |
| WO | WO-03093297 A2 | 11/2003 |

(Continued)

OTHER PUBLICATIONS

Database CAPLUS in STN, Acc. No. 2014:2182008, Tait et al., WO 2014210159 A1 (Dec. 31, 2014) abstract.*
"AID 775-Screen for Chemicals that Extend Yeast Lifespan," PubChem, 1-11 (Jul. 12, 2007), XP055331102.
Bai et al., "Synthesis and Structure-Activity Relationship Studies of Conformationally Flexible Tetrahydroisoquinolinyl Triazole Carboxamide and Triazole Substituted Benzamide Analogues as sigma 2 Receptor Ligands,"Journal of Medicinal Chemistry, 57:10 4239-4251(2014), XP002754990.
Chang, X., "3-(2-chlorophenyl)-N-methylisoxazole-5-Carboxamide," Acta Crystallographica, Section E: Structure Reports Online, vol. E63(7), pp. 03074-sup-7 (2007).
Compound Summary for CID 70741394, Pubchem: Create Date: Mar. 4, 2013 [retrieved on May 12, 2015].
Compound Summary for CID 70756362, Pubchem: Create Date: Mar. 4, 2013 [retrieved on May 12, 2015].
Compound Summary for: CID 36257620, Pubchem: Create Date: May 29, 2009 [retrieved on May 12, 2015].

(Continued)

*Primary Examiner* — Brian J Davis
(74) *Attorney, Agent, or Firm* — Goodwin Procter LLP

(57) ABSTRACT

The invention encompasses compounds such as compounds having the Formula (I) or (II), compositions thereof, and methods of modulating CFTR activity. The invention also encompasses methods of treating a condition associated with CFTR activity or condition associated with a dysfunction of proteostasis comprising administering to a subject an effective amount of a disclosed compound.

38 Claims, No Drawings

(56) References Cited

FOREIGN PATENT DOCUMENTS

| | | |
|---|---|---|
| WO | WO-2005035514 A2 | 4/2005 |
| WO | WO-2005077345 A1 | 8/2005 |
| WO | WO-2005077373 A2 | 8/2005 |
| WO | WO-2006014134 A1 | 2/2006 |
| WO | WO-2006136924 A1 | 12/2006 |
| WO | WO-2007075896 A2 | 7/2007 |
| WO | WO-2007078113 A1 | 7/2007 |
| WO | WO-2007086584 A1 | 8/2007 |
| WO | WO-2007126362 A1 | 11/2007 |
| WO | WO-2008046072 A2 | 4/2008 |
| WO | WO-2008051757 A1 | 5/2008 |
| WO | WO-2008070739 A1 | 6/2008 |
| WO | WO-2009005269 A2 | 1/2009 |
| WO | WO-2009011850 A2 | 1/2009 |
| WO | WO-2009016241 A1 | 2/2009 |
| WO | WO-2010089297 A1 | 8/2010 |
| WO | WO-2010142801 A1 | 12/2010 |
| WO | WO-2011008931 A2 | 1/2011 |
| WO | WO-2012007500 A2 | 1/2012 |
| WO | WO-2013019561 A1 | 2/2013 |
| WO | WO-2013146970 A1 | 10/2013 |
| WO | WO-2014144860 A1 | 9/2014 |
| WO | WO-2014181287 A1 | 11/2014 |
| WO | WO 2014/210159 * 12/2014 ........... A61K 31/422 |
| WO | WO-2014210159 A1 | 12/2014 |
| WO | WO-2015051230 A1 | 4/2015 |
| WO | WO-2015138909 A1 | 9/2015 |
| WO | WO-2015138934 A1 | 9/2015 |
| WO | WO-2015196071 A1 | 12/2015 |
| WO | WO-2016054560 A1 | 4/2016 |
| WO | WO-2016105468 A1 | 6/2016 |
| WO | WO-2016105477 A1 | 6/2016 |
| WO | WO-2016105484 A1 | 6/2016 |
| WO | WO-2016105485 A2 | 6/2016 |
| WO | WO-2016115090 A1 | 7/2016 |
| WO | WO-2017019589 A1 | 2/2017 |

OTHER PUBLICATIONS

Compound Summary for: CID 55795703, Pubchem: Create Date: Jan. 25, 2012 [retrieved on May 12, 2015].

Demina et al., "5-substituted Pyridylisoxazoles as Effective Inhibitors of Platelet Aggregation," Russian Chemical Bulletin, International Edition, vol. 63(2) 2095-2113 (2014).

International Search Report and Written Opinion for International Application No. PCT/US2014/044100, mailed Oct. 10, 2014, 8 pages.

International Search Report and Written Opinion for International Application No. PCT/US2015/000189, mailed Mar. 18, 2016, 10 pages.

International Search Report and Written Opinion for International Application No. PCT/US2015/000202, mailed Mar. 22, 2016, 8 pages.

International Search Report and Written Opinion for International Application No. PCT/US2015/000211, mailed Mar. 29, 2016, 10 pages.

International Search Report and Written Opinion for International Application No. PCT/US2015/000212, mailed Jul. 1, 2016, 22 pages.

International Search Report and Written Opinion for International Application No. PCT/US2015/020460, mailed Jun. 9, 2015, 7 pages.

International Search Report and Written Opinion for International Application No. PCT/US2015/020499, mailed Jun. 9, 2015, 8 pages.

International Search Report and Written Opinion for International Application No. PCT/US2015/036691, mailed Aug. 20, 2015, 12 pages.

International Search Report and Written Opinion for International Application No. PCT/US2016/012982, mailed Mar. 7, 2016, 12 pages.

International Search Report and Written Opinion for International Application No. PCT/US2016/043835, mailed Oct. 10, 2016, 8 pages.

Kalid et al., "Small Molecule Correctors of F508del-CFTR Discovered by Structure-based Virtual Screening," Journal of Computer-Aided Molecular Design, vol. 24:971-991 (2010).

Lack et al., "Targeting the Binding Function 3 (BF3) Site of the Human Androgen Receptor through Virtual Screening," Journal of Medicinal Chemistry, vol. 54(24) 8563-8573 (2011).

Liedtke, W., "Role of TRPV ion Channels in Sensory Transduction of Osmotic Stimuli in Mammals," Experimental Physiology, 92:3 507-512 (2007) XP055252392.

Lukevics et al.,"Synthesis and Cytotoxicity of Silyl- and Carbonyl-substituted Isoxazoles," Chemistry of Heterocyclic Compounds, Springer New York LLC, vol. 36(10); 1226-1231 (1995).

Munchhof et al., "Discovery of PF-04449913, a Potent and Orally Bioavailable Inhibitor of Smoothened," ACS Medicinal Chemistry Letters, vol. 3(2) 106-111 (2012).

Phuan Puay-Wah et al., "Potentiators of Defective Delta F508-CFTR Gating that Do Not Interfere with Corrector Action," XP002754658, Database Accession No. PREV201500722877, Database Biosis [Online] Biosciences Information Service, Philadelphia, PA, US; Oct. 1, 2015 (Oct. 1, 2015). 1 page.

Qian et al., "Potent MCH-1 Receptor Antagonists from Cis-1,4-Diaminocyclohexane-derived Indane Analogs," Bioorganic & Medicinal Chemistry Letters, 23:14 4216-4220 (2013).

Stoops et al., "Identification and Optimization of Small Molecules that Restore E-cadherin Expression and Reduce Invasion in Colorectal Carcinoma Cells," ACS Chemical Biology, American Chemical Society, Washington, DC, US, vol. 6., No. 5, pp. 452-465 (2011).

Supplemental European Search Report mailed Jan. 9, 2017 in European Patent No. 14816975.8 (19 pages).

Pubchem: "ST062658 I C15H12N2O3—PubChem", Jul. 9, 2005 (Jul. 9, 2005), XP055331105, Retrieved from the Internet: URL:https://pubchem.ncbi.nlm.nih.gov/compound/973870#section=Biological-Test-Results [retrieved on Dec. 22, 2016].

U.S. Appl. No. 14/900,345, published as US 2016-0151335 A1 on Jun. 2, 2016, Methods of Modulating CFTR Activity, Dec. 21, 2015.

U.S. Appl. No. 15/125,830; published as US 2017-0001991 A1 on Jan. 5, 2017, Compounds, Compositions and Methods for Increasing CFTR Activity, Sep. 13, 2016.

U.S. Appl. No. 15/320,172, Compounds, Compositions and Methods for Increasing CFTR Activity, Dec. 19, 2016.

* cited by examiner

COMPOUNDS, COMPOSITIONS, AND METHODS FOR INCREASING CFTR ACTIVITY

CROSS-REFERENCE TO RELATED APPLICATIONS

This application is a national stage filing under 35 U.S.C. §371 of PCT/US2015/020460, filed on Mar. 13, 2015, which claims the benefit of United States ("U.S.") Provisional Application No. 61/952,551, filed on Mar. 13, 2014; U.S. Provisional Application No. 62/096,413, filed on Dec. 23, 2014; and U.S. Provisional Application No. 62/102,199, filed on Jan. 12, 2015; each of these prior applications is incorporated herein by reference in its entirety.

BACKGROUND

Cells normally maintain a balance between protein synthesis, folding, trafficking, aggregation, and degradation, referred to as protein homeostasis, utilizing sensors and networks of pathways (Sitia et al., *Nature* 426: 891-894, 2003; Ron et al., *Nat Rev Mol Cell Biol* 8: 519-529, 2007). The cellular maintenance of protein homeostasis, or proteostasis, refers to controlling the conformation, binding interactions, location and concentration of individual proteins making up the proteome. Protein folding in vivo is accomplished through interactions between the folding polypeptide chain and macromolecular cellular components, including multiple classes of chaperones and folding enzymes, which minimize aggregation (Wiseman et al., *Cell* 131: 809-821, 2007). Whether a given protein folds in a certain cell type depends on the distribution, concentration, and subcellular localization of chaperones, folding enzymes, metabolites and the like (Wiseman et al.). Cystic fibrosis and other maladies of protein misfolding arise as a result of an imbalance in the capacity of the protein homeostasis (proteostasis) environment to handle the reduced energetic stability of misfolded, mutated proteins that are critical for normal physiology (Balch et al., *Science* 319, 916-9 (2008); Powers, et al., *Annu Rev Biochem* 78, 959-91 (2009); Hutt et al., *FEBS Lett* 583, 2639-46 (2009)).

Cystic Fibrosis (CF) is caused by mutations in the cystic fibrosis transmembrane conductance regulator (CFTR) gene which encodes a multi-membrane spanning epithelial chloride channel (Riordan et al., *Annu Rev Biochem* 77, 701-26 (2008)). Approximately ninety percent of patients have a deletion of phenylalanine (Phe) 508 (ΔF508) on at least one allele. This mutation results in disruption of the energetics of the protein fold leading to degradation of CFTR in the endoplasmic reticulum (ER). The ΔF508 mutation is thus associated with defective folding and trafficking, as well as enhanced degradation of the mutant CFTR protein (Qu et al., *J Biol Chem* 272, 15739-44 (1997)). The loss of a functional CFTR channel at the plasma membrane disrupts ionic homeostasis ($Cl^-$, $Na^+$, $HCO_3^-$) and airway surface hydration leading to reduced lung function (Riordan et al.). Reduced periciliary liquid volume and increased mucus viscosity impede mucociliary clearance resulting in chronic infection and inflammation, phenotypic hallmarks of CF disease (Boucher, *J Intern Med* 261, 5-16 (2007)). In addition to respiratory dysfunction, ΔF508 CFTR also impacts the normal function of additional organs (pancreas, intestine, gall bladder), suggesting that the loss-of-function impacts multiple downstream pathways that will require correction.

In addition to cystic fibrosis, mutations in the CFTR gene and/or the activity of the CFTR channel has also been implicated in other conditions, including for example, congenital bilateral absence of vas deferens (CBAVD), acute, recurrent, or chronic pancreatitis, disseminated bronchiectasis, asthma, allergic pulmonary aspergillosis, smoking-related lung diseases, such as chronic obstructive pulmonary disease (COPD), dry eye disease, Sjogren's syndrome and chronic sinusitis, (Sloane et al. (2012), PLoS ONE 7(6): e39809.doi:10.1371/journal. pone.0039809; Bombieri et al. (2011), J Cyst Fibros. 2011 June; 10 Suppl 2:S86-102; (Albert et al. (2008). Clinical Respiratory Medicine, Third Ed., Mosby Inc.; Levin et al. (2005), Invest Ophthalmol Vis Sci., 46(4):1428-34; Froussard (2007), Pancreas 35(1):94-5).

There remains a need in the art for compounds, compositions and methods of increasing CFTR activity as well as for methods of treating CF, other CFTR-related diseases, and other maladies of protein misfolding.

SUMMARY

The present disclosure is based, in part, on the discovery that disclosed compounds such as those having Formula (I) can increase cystic fibrosis transmembrane conductance regulator (CFTR) activity as measured in human bronchial epithelial (hBE) cells. Disclosed herein are compounds such as those having Formula (I):

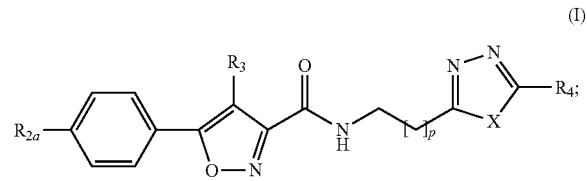

(I)

or a pharmaceutically acceptable salt, prodrug or solvate thereof, wherein:

X is oxygen or sulfur;

$R_{2a}$ is hydrogen or fluoro;

$R_3$ is hydrogen or fluoro;

$R_4$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $NR_d(CO-OR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, optionally substituted heterocyclic and optionally substituted heteroaryl. For example, in some embodiments, $R_4$ is optionally substituted $C_1$-$C_{10}$ alkyl, e.g., $C_1$-$C_{10}$ alkyl or $C_1$-$C_6$ alkyl optionally substituted with one or more (e.g., one, two or three) $OR_f$, and/or one or more halo (e.g., one, two or three) (e.g., F), in which $R_f$ can be, e.g., H or $C_1$-$C_{10}$ alkyl, e.g., $C_1$-$C_6$ alkyl, e.g., $CH_3$; e.g., $R_4$ can be a primary, secondary, or tertiary alcohol (e.g., OH) or ether moiety (e.g., —$OCH_3$), optionally further substituted with one or more halo, e.g., F;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl;

each n is independently 0, 1 or 2; and p is 1 or 2; and in some embodiments, provided that the compound is not for example, N-[2-(5-ethyl-1,3,4-thiadiazol-2-yl)ethyl]-5-phenyl-3-isoxazolecarboxamide.

Also disclosed herein are compounds having formula (II):

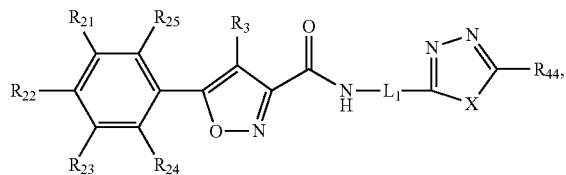

(II)

in which:

X is oxygen or sulfur;

$R_{21}$, $R_{22}$, $R_{23}$, $R_{24}$, and $R_{25}$ are each independently selected from hydrogen or fluoro;

$R_3$ is hydrogen or fluoro;

$L_1$ is $C_{2-3}$ alkylene, optionally substituted by one, two or three substituents selected from the group consisting of halogen, hydroxyl, $C_{1-3}$alkyl (optionally substituted by one, two or three substituents each selected independently from $R_{ff}$);

$R_{44}$ is selected from the group consisting of halogen, hydroxyl, $C_{1-6}$alkyl, $C_{1-6}$alkoxy, $C_{2-6}$alkenyl, $C_{2-6}$ alkynyl, and $C_{3-7}$ cycloalkyl, wherein $C_{1-6}$ alkyl is substituted by one, two or three substituents each independently selected from $R_{gg}$, and each of $C_{1-6}$ alkoxy, $C_{2-6}$ alkenyl, $C_{2-6}$ alkynyl, and $C_{3-7}$ cycloalkyl may be optionally substituted by one, two or three substituents each independently selected from $R_{gg}$;

$R_{gg}$ is selected from the group consisting of halogen, $C_{1-6}$alkyl, $C_{1-6}$alkoxy, hydroxyl, C(O)OH, —C(O)OC$_{1-6}$alkyl, —O—$C_{3-6}$ cycloalkyl, —O-heterocycle, —O-heteroaryl, —O-phenyl, CN, N$_3$, —NR'R", —NR'—S(O)$_w$—$C_{1-3}$alkyl, S(O)$_w$—NR'R", and —S(O)$_w$—$C_{1-3}$alkyl, where w is 0, 1, or 2;

$R_{ff}$ is selected for each occurrence from group consisting of halogen, hydroxyl, $C_{1-4}$alkyl, $C_{1-4}$ alkoxy, $C_{2-4}$ alkenyl, $C_{3-6}$ cycloalkyl, —NR'R", —NR'—S(O)$_w$—$C_{1-3}$alkyl, S(O)$_w$—NR'R", and —S(O)$_w$—$C_{1-3}$alkyl, where w is 0, 1, or 2, wherein $C_{1-4}$ alkyl, $C_{1-4}$alkyoxy, $C_{2-4}$alkenyl and $C_{3-6}$cycloalkyl may be optionally substituted by one, two or three substituents each independently selected from the group consisting of halogen, hydroxyl, —NR'R", —NR'—S(O)$_w$—$C_{1-3}$alkyl, S(O)$_w$—NR'R", and —S(O)$_w$—$C_{1-3}$ alkyl; and R' and R" are each independently selected for each occurrence from H and $C_{1-4}$alkyl or taken together with the nitrogen to which they are attached form a heterocyclic ring.

Also contemplated herein are pharmaceutical compositions that include a disclosed compound such as those compounds having Formula (I) or (II), and a pharmaceutically acceptable carrier or excipient.

In additional embodiments, a method of increasing cystic fibrosis transmembrane conductance regulator (CFTR) activity in a subject in need thereof is provided, comprising administering to said subject an effective amount of a disclosed compound.

In yet additional aspects, a method of treating a patient suffering from cystic fibrosis comprising administering to said patient an effective amount of a disclosed compound is provided herein.

In certain of these embodiments, the activity of one or more (e.g., one or two) mutant CFTRs (e.g., ΔF508, S549N, G542X, G551D, R117H, N1303K, W1282X, R553X, 621+1G>T, 1717-1G>A, 3849+10kbC>T, 2789+5G>A, 3120+1G>A, I507del, R1162X, 1898+1G>A, 3659delC, G85E, D1152H, R560T, R347P, 2184insA, A455E, R334W, Q493X, and 2184delA CFTR) is enhanced (e.g., increased). In certain embodiments, ΔF508 CFTR activity is enhanced (e.g., increased). In other embodiments, the activities of two mutant CFTRs (e.g., ΔF508 and G551D; ΔF508 and A455E; or G542X and Δ508F) are enhanced (e.g., increased).

DETAILED DESCRIPTION

As used herein, the words "a" and "an" are meant to include one or more unless otherwise specified. For example, the term "an agent" encompasses both a single agent and combination of two or more agents.

As discussed above, the present disclosure is directed in part to compounds as described herein, or a pharmaceutically acceptable salt, prodrug or solvate thereof, pharmaceutical compositions, methods of increasing CFTR activity and methods of treating cystic fibrosis.

In certain aspects, the compound has the Formula (I), wherein p is 1.

In yet additional aspects, the compound has the Formula (I), wherein p is 2.

In additional embodiments, the compound has the Formula (I), wherein X is oxygen.

In yet additional embodiments, the compound has the Formula (I), wherein X is sulfur.

In some embodiments, the compound has the Formula (I), wherein $R_3$ is hydrogen.

In additional embodiments, the compound has the Formula (I), wherein $R_3$ is fluoro.

In additional embodiments, the compound has the Formula (I), wherein $R_{2a}$ is hydrogen. In yet additional embodiments, the compound has the Formula (I), wherein $R_{2a}$ is fluoro.

In further aspects, the compound has the Formula (I), wherein $R_4$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, halo, $OR_c$, $NR_dR_d$, $S(O)_nR_c$, $C(O)OR_c$, $NO_2$, CN, and $C(O)R_c$. In yet additional aspects, $R_4$ is selected from the group consisting of optionally substituted $C_1$-$C_{10}$ alkyl, optionally substituted $C_3$-$C_{12}$ cycloalkyl, and $OR_3$, wherein $R_3$ is an optionally substituted $C_1$-$C_{10}$ alkyl. In additional embodiments, $R_4$ is $C_1$-$C_4$ alkyl or $C_3$-$C_7$ cycloalkyl, wherein the $C_1$-$C_4$ alkyl and $C_3$-$C_7$ cycloalkyl are each optionally substituted with one or more groups selected from $OR_f$, $NR_gR_g$, and $SR_h$, wherein each of $R_f$ and $R_h$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; and each $R_g$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl; or alternatively, two geminal $R_g$ groups are taken together with the nitrogen atom to which they are attached to form an optionally substituted heterocyclic or an optionally substituted heteroaryl. In further aspects, $R_4$ is $C_1$-$C_4$ alkyl optionally substituted with $OR_f$, wherein $R_f$ is selected from the group consisting of hydrogen, optionally substituted $C_1$-$C_{10}$ alkyl, and optionally substituted $C_3$-$C_{12}$ cycloalkyl. In certain aspects, $R_f$ is hydrogen or optionally substituted $C_1$-$C_4$ alkyl. In yet additional embodiments, $R_4$ is a $C_1$-$C_4$ alkyl substituted with one or more halo, and optionally further substituted. In additional aspects, $R_4$ is a $C_1$-$C_4$ alkyl substituted with one or more fluoro, and optionally further substituted.

In yet additional embodiments, the compound has the Formula (I), wherein $R_4$ is:

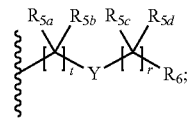

wherein $R_{5a}$, $R_{5b}$, $R_{5c}$, and $R_{5d}$ are each independently selected from the group consisting of hydrogen, optionally substituted $C_1$-$C_{10}$ alkyl and optionally substituted $C_3$-$C_{12}$ cycloalkyl; or alternatively, a geminal $R_{5a}$ and $R_{5b}$ can be taken together with the carbon atom to which they are attached to form an optionally substituted $C_3$-$C_{12}$ cycloalkyl or an optionally substituted heterocyclic, and/or a geminal $R_{5c}$ and $R_{5d}$ can be taken together with the carbon atom to which they are attached to form an optionally substituted $C_3$-$C_{12}$ cycloalkyl or an optionally substituted heterocyclic; Y is O, S or $NR_1$; t and r are each independently 0, 1, 2 or 3; $R_6$ is selected from the group consisting of optionally substituted $C_1$-$C_{10}$ alkyl and optionally substituted $C_3$-$C_{12}$ cycloalkyl, optionally substituted heterocyclic, optionally substituted aryl, and optionally substituted heteroaryl; and $R_1$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl. In some embodiments, the geminal $R_{5a}$ and $R_{5b}$ can be taken together with the carbon atom to which they are attached to form an optionally substituted $C_3$-$C_7$ cycloalkyl or an optionally substituted 3- to 7-membered heterocyclic, and/or a geminal $R_{5c}$ and $R_{5d}$ can be taken together with the carbon atom to which they are attached to form an optionally substituted $C_3$-$C_7$ cycloalkyl or an optionally substituted 3- to 7-membered heterocyclic. In yet additional embodiments, t and r are each independently 0, 1 or 2.

In yet additional embodiments, a disclosed compound has the Formula (II) wherein for example. $R_{44}$ is $C_{1-6}$alkyl is substituted by one, two or three substituents each independently selected from $R_{gg}$. For example, $R_{44}$ can be methyl substituted by one, two or three substituents each selected from halogen, hydroxyl, CN, $N_3$, methoxy and ethoxy, ethyl substituted by one, two or three substituents each selected from halogen, hydroxyl, methoxy and ethoxy, propyl substituted by one, two or three substituents each selected from halogen, hydroxyl, —CN, $N_3$, methoxy and ethoxy), isopropyl substituted by one, two or three substituents each selected from halogen, CN, $N_3$, hydroxyl, methoxy and ethoxy, n-butyl substituted by one, two or three substituents each selected from halogen, CN, $N_3$, hydroxyl, methoxy and ethoxy, t-butyl substituted by one, two or three substituents each selected from halogen, CN, $N_3$, hydroxyl, methoxy and ethoxy, s-butyl substituted by one, two or three substituents each selected from halogen, CN, $N_3$, hydroxyl, methoxy and ethoxy and isobutyl substituted by one, two or three substituents each selected from halogen, CN, $N_3$, hydroxyl, methoxy and ethoxy. For example, $R_{44}$ may be substituted on a primary, secondary, and/or tertiary carbon.

In certain embodiments, a disclosed compound has Formula (I), provided that the compound is not one or more of 5-phenyl-N-[2-(5-phenyl-1,2,4-oxadiazol-3-yl)ethyl]-3-isoxazolecarboxamide, N-[2-(5-phenyl-1,3,4-oxadiazol-2-yl)ethyl]-5-phenyl-3-isoxazolecarboxamide; N-[2-(5-methyl-1,3,4-thiadiazol-2-yl)ethyl]-5-phenyl-3-isoxazolecarboxamide, N-[2-(5-ethyl-1,3,4-thiadiazol-2-yl)ethyl]-5-phenyl-3-isoxazolecarboxamide, or N-(3-(5-amino-1,3,4-thiadiazol-2-yl)propyl)-5-phenylisoxazole-3-carboxamide.

Exemplary compounds of Formula (I) are Compounds A1 to A25 shown below in Table 1.

TABLE 1

| Compound | Structure |
| --- | --- |
| A1 (Example 6) | ![structure] |
| A2 (Example 3) | ![structure] |

TABLE 1-continued

| Compound | Structure |
| --- | --- |
| A3 (Example 4) | 5-phenylisoxazole-3-carboxamide linked via -NH-CH₂CH₂- to 5-(bromomethyl)-1,3,4-thiadiazol-2-yl |
| A4 (Example 2) | 5-phenylisoxazole-3-carboxamide linked via -NH-CH₂CH₂- to 5-(methoxymethyl)-1,3,4-thiadiazol-2-yl |
| A5 (Example 5) | 5-phenylisoxazole-3-carboxamide linked via -NH-CH₂CH₂- to 5-(methoxymethyl)-1,3,4-oxadiazol-2-yl |
| A6 (Example 1) | 5-phenylisoxazole-3-carboxamide linked via -NH-CH₂CH₂CH₂- to 5-methyl-1,3,4-thiadiazol-2-yl |
| A7 (Example 7) | 5-(azidomethyl)-1,3,4-thiadiazol-2-yl linked via -CH₂CH₂-NH- to 5-phenylisoxazole-3-carboxamide |
| A8 (Example 8) | 5-phenylisoxazole-3-carboxamide linked via -NH-CH₂CH₂- to 5-isopropyl-1,3,4-oxadiazol-2-yl |
| A9 (Example 9) | 5-phenylisoxazole-3-carboxamide linked via -NH-CH₂CH₂- to 5-(2-hydroxypropan-2-yl)-1,3,4-thiadiazol-2-yl |
| A10 (Example 10) | 5-phenylisoxazole-3-carboxamide linked via -NH-CH₂CH₂- to 5-(2-hydroxypropan-2-yl)-1,3,4-oxadiazol-2-yl |

TABLE 1-continued

| Compound | Structure |
|---|---|
| A11 (Example 11) | 5-phenyl-4-fluoro-isoxazole-3-carboxamide linked via -NH-CH₂CH₂- to 5-(hydroxymethyl)-1,3,4-thiadiazol-2-yl |
| A12 (Example 12) | 5-(4-fluorophenyl)-4-fluoro-isoxazole-3-carboxamide linked via -NH-CH₂CH₂- to 5-(hydroxymethyl)-1,3,4-thiadiazol-2-yl |
| A13 (Example 13) | 5-phenyl-isoxazole-3-carboxamide linked via -NH-CH₂CH₂- to 5-[(S)-1-hydroxyethyl]-1,3,4-thiadiazol-2-yl |
| A14 (Example 14) | 5-phenyl-isoxazole-3-carboxamide linked via -NH-CH₂CH₂- to 5-(1-hydroxyethyl)-1,3,4-oxadiazol-2-yl |
| A15 (Example 15) | 5-phenyl-isoxazole-3-carboxamide linked via -NH-CH₂CH₂- to 5-(OCF₃-methyl)-1,3,4-oxadiazol-2-yl |
| A16 (Example 16) | 5-phenyl-isoxazole-3-carboxamide linked via -NH-CH₂CH₂- to 5-(OCF₃-methyl)-1,3,4-thiadiazol-2-yl |
| A17 (Example 17) | 5-phenyl-isoxazole-3-carboxamide linked via -NH-CH₂CH₂- to 5-[(R)-1-hydroxyethyl]-1,3,4-thiadiazol-2-yl |
| A18 (Example 18) | 5-phenyl-isoxazole-3-carboxamide linked via -NH-CH₂CH₂- to 5-[(R)-1-hydroxyethyl]-1,3,4-oxadiazol-2-yl |
| A19 (Example 19) | 5-phenyl-isoxazole-3-carboxamide linked via -NH-CH₂CH₂- to 5-[(R)-1,2-dihydroxyethyl]-1,3,4-oxadiazol-2-yl |

TABLE 1-continued

| Compound | Structure |
|---|---|
| A20 (Example 20) | 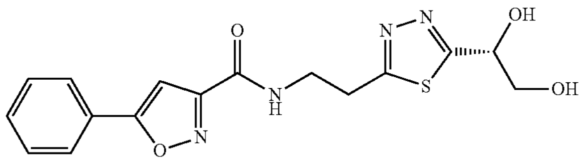 |
| A21 (Example 21) | 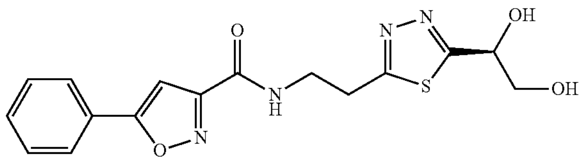 [SMILES: O=C(NCCc1nnc([C@@H](O)CO)s1)c1cc(-c2ccccc2)on1] |
| A22 (Example 22) | 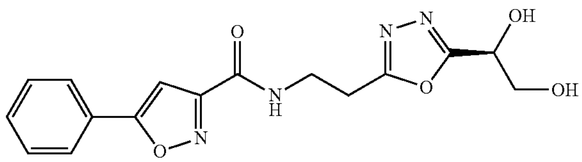 |
| A23 (Example 23) | 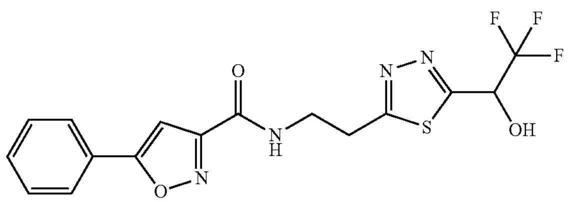 [SMILES: O=C(NCCc1nnc(C(O)C(F)(F)F)s1)c1cc(-c2ccccc2)on1] |
| A24-a (Example 24) | 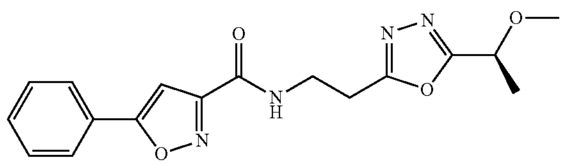 |
| A24-b (Example 24) | 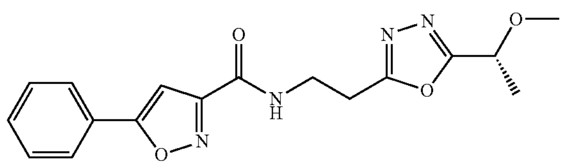 [SMILES: CO[C@H](C)c1nnc(CCNC(=O)c2cc(-c3ccccc3)on2)o1] |
| A25-a (Example 25) | 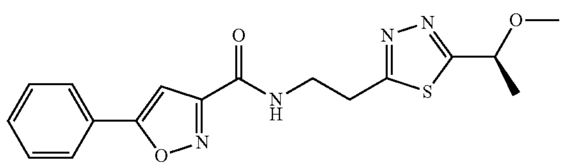 |
| A25-b (Example 25) | 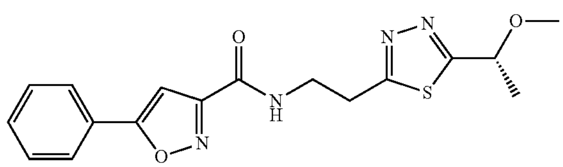 |

In yet additional embodiments, provided herein is a pharmaceutical composition comprising a contemplated compound, for example, a compound of Formula (I) or (II), and a pharmaceutically acceptable carrier or excipient.

It is to be understood that the specific embodiments described herein can be taken in combination with other specific embodiments delineated herein. For example, as discussed above, in some embodiments, $R_{2a}$ is fluoro, X is sulfur in some embodiments, and in some embodiments described above, $R_4$ is optionally substituted $C_1$-$C_{10}$ alkyl. For example, the disclosure contemplates a compound of Formula (I) wherein $R_{2a}$ is fluoro, X is sulfur and $R_4$ is an optionally substituted $C_1$-$C_{10}$ alkyl. In an additional example, as discussed above, in some embodiments, $R_{2a}$ is fluoro, X is oxygen in some embodiments, and in some embodiments described above, $R_4$ is optionally substituted $C_1$-$C_{10}$ alkyl. In another embodiment, the disclosure contemplates compounds of Formula (I) wherein $R_{2a}$ is fluoro, X is oxygen and $R_4$ is an optionally substituted $C_1$-$C_{10}$ alkyl.

The features and other details of the disclosure will now be more particularly described. Before further description, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

It will be appreciated that the description of disclosed compounds herein should be construed in congruity with the laws and principals of chemical bonding.

The term "alkyl", as used herein, unless otherwise indicated, refers to both branched and straight-chain saturated aliphatic hydrocarbon groups having the specified number of carbon atoms; for example, "$C_1$-$C_{10}$ alkyl" denotes alkyl having 1 to 10 carbon atoms, and straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

The term, "alkenyl", as used herein, refers to both straight and branched-chain moieties having the specified number of carbon atoms and having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

The term, "alkynyl", as used herein, refers to both straight and branched-chain moieties having the specified number or carbon atoms and having at least one carbon-carbon triple bond.

The term "cycloalkyl," as used herein, refers to saturated cyclic alkyl moieties having 3 or more carbon atoms, for example, 3-10, 3-6, or 4-6 carbons, referred to herein as $C_{3-10}$cycloalkyl, $C_{3-6}$cycloalkyl or $C_{4-6}$cycloalkyl, respectively for example, Examples of cycloalkyl include, but are not limited to, cyclopropyl, cyclobutyl, cyclopentyl, cyclohexyl, cycloheptyl and adamantyl.

The term "cycloalkenyl," as used herein, refers to cyclic alkenyl moieties having 3 or more carbon atoms.

The term "cycloalkynyl," as used herein, refers to cyclic alkynyl moieties having 5 or more carbon atoms.

"Alkylene" means a straight or branched, saturated aliphatic divalent radical having the number of carbons indicated. "Cycloalkylene" refers to a divalent radical of carbocyclic saturated hydrocarbon group having the number of carbons indicated.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "heterocyclic" or "heterocycle" encompasses heterocycloalkyl, heterocycloalkenyl, heterobicycloalkyl, heterobicycloalkenyl, heteropolycycloalkyl, heteropolycycloalkenyl, and the like unless indicated otherwise. Heterocycloalkyl refers to cycloalkyl groups containing one or more heteroatoms (O, S, or N) within the ring. Heterocycloalkenyl as used herein refers to cycloalkenyl groups containing one or more heteroatoms (O, S or N) within the ring. Heterobicycloalkyl refers to bicycloalkyl groups containing one or more heteroatoms (O, S or N) within a ring. Heterobicycloalkenyl as used herein refers to bicycloalkenyl groups containing one or more heteroatoms (O, S or N) within a ring, a heterocycle can refer to, for example, a saturated or partially unsaturated 4- to 12 or 4-10-membered ring structure, including bridged or fused rings, and whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran etc.

Cycloalkyl, cycloalkenyl, heterocyclic, groups also include groups similar to those described above for each of these respective categories, but which are substituted with one or more oxo moieties.

The term "aryl", as used herein, refers to mono- or polycyclic aromatic carbocyclic ring systems. A polycyclic aryl is a polycyclic ring system that comprises at least one aromatic ring. Polycyclic aryls can comprise fused rings, covalently attached rings or a combination thereof. The term "aryl" embraces aromatic radicals, such as, phenyl, naphthyl, indenyl, tetrahydronaphthyl, and indanyl. An aryl group may be substituted or unsubstituted. In some embodiments, the aryl is a $C_4$-$C_{10}$ aryl. Examples of optionally substituted aryl are phenyl, substituted phenyl, napthyl and substituted naphthyl.

The term "heteroaryl", as used herein, refers to aromatic carbocyclic groups containing one or more heteroatoms (O, S, or N) within a ring. A heteroaryl group, unless indicated otherwise, can be monocyclic or polycyclic. A heteroaryl group may additionally be substituted or unsubstituted. Contemplated heteroaryl groups can also include ring systems substituted with one or more oxo moieties. A polycyclic heteroaryl can comprise fused rings, covalently attached rings or a combination thereof. A polycyclic heteroaryl is a polycyclic ring system that comprises at least one aromatic ring containing one or more heteroatoms within a ring. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, thiazolopyridinyl, oxazolopyridinyl and azaindolyl. The foregoing heteroaryl groups may be C-attached or heteroatom-attached (where such is possible). For instance, a group derived from pyrrole may be pyrrol-1-yl (N-attached) or pyrrol-3-yl (C-attached). In some embodiments, the heteroaryl is a mono or bicyclic 4- to 12-membered heteroaryl. In yet other embodiments, the heteroaryl is a 4- to 10-membered heteroaryl.

The term "substituted" refers to substitution by independent replacement of one, two, or three or more of the hydrogen atoms with substituents including but not limited to, and unless indicated otherwise, —$C_1$-$C_{12}$ alkyl, —$C_2$-$C_{12}$ alkenyl, —$C_2$-$C_{12}$ alkynyl, —$C_3$-$C_{12}$ cycloalkyl, —$C_3$-$C_{12}$ cycloalkenyl, $C_3$-$C_{12}$ cycloalkynyl, -heterocyclic, —F, —Cl, —Br, —I, —OH, —NO$_2$, —N$_3$, —CN, —NH$_2$, oxo, thioxo, —NHR$_x$, —NR$_x$R$_x$, dialkylamino, -diarylamino, -diheteroarylamino, —OR$_x$, —C(O)R$_y$, —C(O)C(O)R$_y$, —OCO$_2$R$_y$, —OC(O)R$_y$, OC(O)C(O)R$_y$, —NHC(O)R$_y$, —NHCO$_2$R$_y$, —NHC(O)C(O)R$_y$, NHC(S)NH$_2$, —NHC(S)NHR$_x$, —NHC(NH)NH$_2$, —NHC(NH)NHR$_x$, —NHC(NH)R$_x$, —C(NH)NHR$_x$, and (C=NR$_x$)R$_x$; —NRxC(O)R$_x$, —NR$_x$C(O)N(R$_x$)$_2$, —NRxCO$_2$R$_y$, —NRxC(O)C(O)R$_y$, —NR$_x$C(S)NH$_2$, —NR$_x$C(S)NHR$_x$, —NR$_x$C(NH)NH$_2$, —NR$_x$C(NH)NHR$_x$, —NRxC(NH)R$_x$, —C(NRx)NHR$_x$—S(O)R$_y$, —NHSO$_2$R$_x$, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, -polyalkoxyalkyl, -polyalkoxy, -methoxymethoxy, -methoxyethoxy, —SH, —S—R$_x$, or -methylthiomethyl, wherein R$_x$ is selected from the group consisting of hydrogen, —C$_1$-C$_{12}$ alkyl, —C$_2$-C$_{12}$ alkenyl, —C$_2$-C$_{12}$ alkynyl, —C$_3$-C$_{12}$ cycloalkyl, -aryl, -heteroaryl and -heterocyclic and —R$_y$ is selected from the group consisting of hydrogen, —C$_1$-C$_{12}$ alkyl, —C$_2$-C$_{12}$ alkenyl, —C$_2$-C$_{12}$ alkynyl, —C$_3$-C$_{12}$ cycloalkyl, -aryl, -heteroaryl, -heterocyclic, —NH$_2$, —NH—C$_1$-C$_{12}$ alkyl, —NH—C$_2$-C$_{12}$ alkenyl, —NH—C$_2$-C$_{12}$-alkynyl, —NH—C$_3$-C$_{12}$ cycloalkyl, —NH-aryl, —NH-heteroaryl and —NH-heterocyclic. It is understood that the aryls, heteroaryls, alkyls, and the like can be further substituted.

The terms "halo" or "halogen" as used herein refer to F, Cl, Br, or I.

The term "haloalkyl" as used herein refers to an alkyl group having 1 to (2n+1) substituent(s) independently selected from F, Cl, Br or I, where n is the maximum number of carbon atoms in the alkyl group. It will be understood that haloalkyl is a specific example of an optionally substituted alkyl.

The terms "hydroxy" and "hydroxyl" as used herein refers to the radical —OH.

As will be understood by the skilled artisan, "H" is the symbol for hydrogen, "N" is the symbol for nitrogen, "S" is the symbol for sulfur, "O" is the symbol for oxygen. "Me" is an abbreviation for methyl.

Compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. For example, various stereoisomers of disclosed compounds and mixtures thereof are contemplated. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ⁓ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic ring may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diasteriomers of disclosed compounds can be prepared for example by synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing a disclosed compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009. Where a particular compound is described or depicted, it is intended to encompass that chemical structure as well as tautomers of that structure.

The term "enantiomerically pure" means a stereomerically pure composition of a compound. For example, a stereochemically pure composition is a composition that is free or substantially free of other stereoisomers of that compound. In another example, for a compound having one chiral center, an enantiomerically pure composition of the compound is free or substantially free of the other enantiomer. In yet another example, for a compound having two chiral centers, an enantiomerically pure composition is free or substantially free of the other diastereomers.

Where a particular stereochemistry is described or depicted it is intended to mean that a particular enantiomer is present in excess relative to the other enantiomer. A compound has an R-configuration at a specific position when it is present in excess compared to the compound having an S-configuration at that position. A compound has an S-configuration at a specific position when it is present in excess compared to the compound having an R-configuration at that position.

Compounds disclosed herein can exist in solvated as well as unsolvated forms with pharmaceutically acceptable solvents such as water, ethanol, and the like, and it is intended that compounds described herein can for example embrace both solvated and unsolvated forms. In one embodiment, a disclosed compound is amorphous. In one embodiment, a disclosed compound is a single polymorph. In another embodiment, a disclosed compound is a mixture of polymorphs. In another embodiment, a disclosed compound is in a crystalline form.

Contemplated herein in certain embodiments are isotopically labeled compounds which are identical to those recited herein, except that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. For example, a disclosed compound may for example have one or more H atom replaced with deuterium.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds, for example, can generally be prepared by following procedures analogous to those disclosed in the examples herein by substituting an isotopically labeled reagent for a non-isotopically labeled reagent. Also contemplated herein are compounds wherein one or more of the nitrogen atoms in a disclosed compound is oxidized to N-oxide.

An exemplary synthetic route for the preparation of compound of Formula (I) is shown in the exemplary schemes below. As will be understood by the skilled artisan, diastereomers can be separated from the reaction mixture for example, using column chromatography.

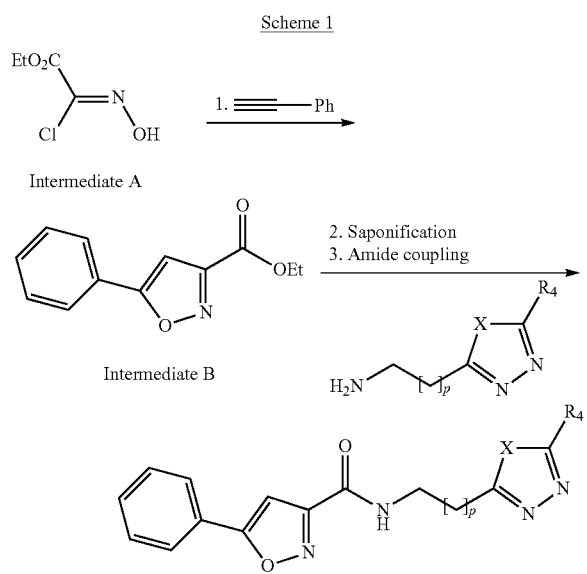

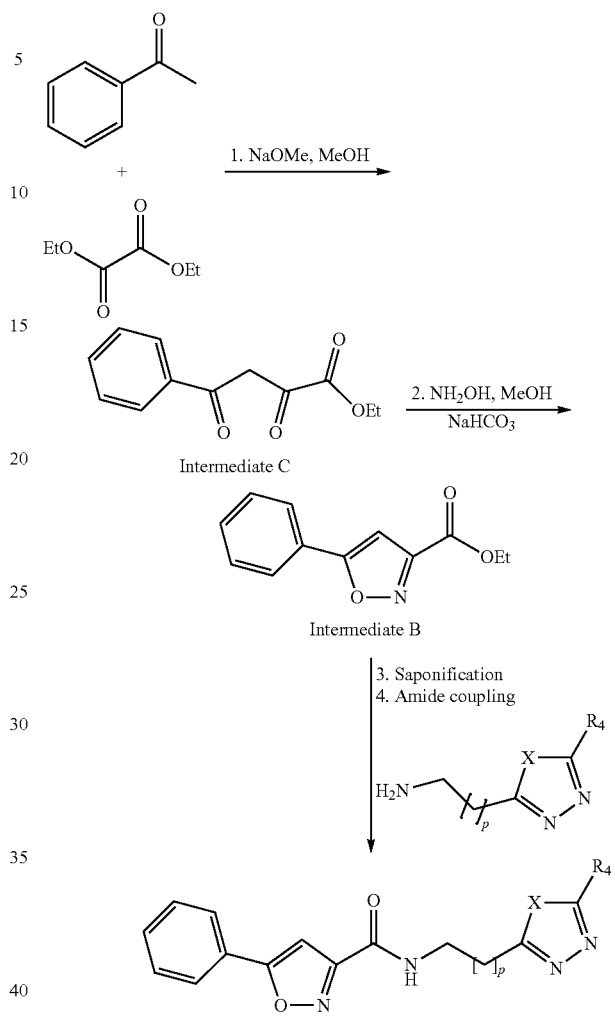

Disclosed compounds can also be prepared for example, using methods described in the literature, including, but not limited to, *J. Med. Chem.* 2011, 54(13), 4350-64; *Russian Journal of Organic Chemistry*, 2011, 47(8), 1199-1203; U.S. Patent Application Publication No. 2009/0036451 A1; WO2008/046072 A2, and U.S. Pat. No. 4,336,264, the contents of each of which are expressly incorporated by reference herein.

As discussed above, also disclosed herein is a method of increasing CFTR activity in a subject comprising administering a disclosed compound in an effective amount. In an embodiment, a method of treating a patient suffering from a condition associated with CFTR activity comprising administering to said patient an effective amount of a compound described herein "Treating" or "treatment" includes preventing or delaying the onset of the symptoms, complications, or biochemical indicia of a disease, alleviating or ameliorating the symptoms or arresting or inhibiting further development of the disease, condition, or disorder. A "subject" is an animal to be treated or in need of treatment. A "patient" is a human subject in need of treatment.

An "effective amount" refers to that amount of an agent that is sufficient to achieve a desired and/or recited effect. In the context of a method of treatment, an "effective amount"

of the therapeutic agent that is sufficient to ameliorate of one or more symptoms of a disorder and/or prevent advancement of a disorder, cause regression of the disorder and/or to achieve a desired effect.

The term "modulating" encompasses increasing, enhancing, inhibiting, decreasing, suppressing, and the like. The terms "increasing" and "enhancing" mean to cause a net gain by either direct or indirect means. As used herein, the terms "inhibiting" and "decreasing" encompass causing a net decrease by either direct or indirect means.

In some examples, CFTR activity is enhanced after administration of a compound described herein when there is an increase in the CFTR activity as compared to that in the absence of the administration of the compound. CFTR activity encompasses, for example, chloride channel activity of the CFTR, and/or other ion transport activity (for example, $HCO_3^-$ transport). In certain of these embodiments, the activity of one or more (e.g., one or two) mutant CFTRs (e.g., ΔF508, S549N, G542X, G551D, R117H, N1303K, W1282X, R553X, 621+1G>T, 1717-1G>A, 3849+10kbC>T, 2789+5G>A, 3120+1G>A, I507del, R1162X, 1898+1G>A, 3659delC, G85E, D1152H, R560T, R347P, 2184insA, A455E, R334W, Q493X, and 2184delA CFTR) is enhanced (e.g., increased). Contemplated patients may have a CFTR mutation(s) from one or more classes, such as without limitation, Class I CFTR mutations, Class II CFTR mutations, Class III CFTR mutations, Class IV CFTR mutations, Class V CFTR mutations, and Class VI mutations. Contemplated subject (e.g., human subject) CFTR genotypes include, without limitation, homozygote mutations (e.g., ΔF508/ΔF508 and R117H/R117H) and compound heterozygote mutations (e.g., ΔF508/G551D; ΔF508/A455E; ΔF508/G542X; Δ508F/W1204X; R553X/W1316X; W1282X/N1303K, 591Δ18/E831X, F508del/R117H/N1303K/3849+10kbC>T; Δ303K/384; and DF508/G178R).

In certain embodiments, the mutation is a Class I mutation, e.g., a G542X Class I mutation; e.g., a Class II/I mutation, e.g., a ΔF508/G542X compound heterozygous mutation. In other embodiments, the mutation is a Class III mutation, e.g., a G551D Class III mutation; e.g., a Class II/Class III mutation, e.g., a ΔF508/G551D compound heterozygous mutation. In still other embodiments, the mutation is a Class V mutation, e.g., a A455E Class V mutation; e.g., a Class II/Class V mutation, e.g., a ΔF508/A455E compound heterozygous mutation. Of the more than 1000 known mutations of the CFTR gene, ΔF508 is the most prevalent mutation of CFTR which results in misfolding of the protein and impaired trafficking from the endoplasmic reticulum to the apical membrane (Dormer et al. (2001). *J Cell Sci* 114, 4073-4081; http://www.genet.sickkids.on.ca/app). In certain embodiments, ΔF508 CFTR activity is enhanced (e.g., increased). In certain embodiments, ΔF508 CFTR activity and/or G542X CFTR activity and/or G551D CFTR activity and/or A455E CFTR activity is enhanced (e.g., increased). An enhancement of CFTR activity can be measured, for example, using literature described methods, including for example, Ussing chamber assays, patch clamp assays, and hBE Ieq assay (Devor et al. (2000), Am J Physiol Cell Physiol 279(2): C461-79; Dousmanis et al. (2002), J Gen Physiol 119(6): 545-59; Bruscia et al. (2005), PNAS 103(8): 2965-2971).

Provided herein is a method of treating cystic fibrosis in a subject or patient in need thereof comprising administering a disclosed compound. Methods of treating other conditions associated with CFTR activity, including conditions associated with deficient CFTR activity is also contemplated.

In some embodiments, a method of treating a condition associated with deficient or decreased CFTR activity comprising administering an effective amount of a compound of Formula (I) that enhances CFTR activity is provided. Non-limiting examples of conditions associated with deficient CFTR activity are cystic fibrosis, congenital bilateral absence of vas deferens (CBAVD), acute, recurrent, or chronic pancreatitis, disseminated bronchiectasis, asthma, allergic pulmonary aspergillosis, smoking-related lung diseases, such as chronic obstructive pulmonary disease (COPD), chronic sinusitis, dry eye disease, protein C deficiency, Aβ-lipoproteinemia, lysosomal storage disease, type 1 chylomicronemia, mild pulmonary disease, lipid processing deficiencies, type 1 hereditary angioedema, coagulation-fibrinolyis, hereditary hemochromatosis, CFTR-related metabolic syndrome, chronic bronchitis, constipation, pancreatic insufficiency, hereditary emphysema, and Sjogren's syndrome.

In some embodiments, disclosed methods of treatment further comprise administering an additional therapeutic agent. For example, in an embodiment, provided herein is a method of administering a disclosed compound and at least one additional therapeutic agent. In certain aspects, the invention is directed to a method comprising administering a disclosed compound, and at least two additional therapeutic agents. Additional therapeutic agents include, for example, mucolytic agents, bronchodilators, antibiotics, anti-infective agents, anti-inflammatory agents, ion channel modulating agents, therapeutic agents used in gene therapy, CFTR correctors, and CFTR potentiators, or other agents that modulates CFTR activity. In some embodiments, at least one additional therapeutic agent is selected from the group consisting of a CFTR corrector and a CFTR potentiator. Non-limiting examples of CFTR correctors and potentiators include VX-770 (Ivacaftor), VX-809 (3-(6-(1-(2,2-difluorobenzo[d][1,3]dioxol-5-yl)cyclopropanecarbox-amido)-3-methylpyridin-2-yl)benzoic acid, VX-661 (1-(2,2-difluoro-1,3-benzodioxol-5-yl)-N-[1-[(2R)-2,3-dihydroxypropyl]-6-fluoro-2-(2-hydroxy-1,1-dimethylethyl)-1H-indol-5-yl]-cyclopropanecarboxamide), VX-983, and Ataluren (PTC124) (3-[5-(2-fluorophenyl)-1,2,4-oxadiazol-3-yl]benzoic acid), FDL169, GLPG1837/ABBV-974 (for example, a CFTR potentiator), GLPG2222 (for example, a CFTR corrector); and compounds described in, e.g., WO2014/144860 and 2014/176553, hereby incorporated by reference. Non-limiting examples of modulators include QBW-251, QR-010, NB-124, and compounds described in, e.g., WO2014/045283; WO2014/081821, WO2014/081820, WO2014/152213; WO2014/160440, WO2014/160478, US2014027933; WO2014/0228376, WO2013/038390, WO2011/113894, WO2013/038386; and WO2014/180562, of which the disclosed modulators in those publications are contemplated as an additional therapeutic agents and incorporated by reference. Non-limiting examples of anti-inflammatory agents include N6022 (3-(5-(4-(1H-imidazol-1-yl) phenyl)-1-(4-carbamoyl-2-methyl-phenyl)-$^1$H-pyrrol-2-yl) propanoic acid), CTX-4430, N1861, N1785, and N91115.

In some embodiments, the methods described herein can further include administering an additional therapeutic agent or administering at least two additional CFTR therapeutic agents. In some embodiments, the methods described herein can further include administering an additional CFTR modulator or administering at least two additional CFTR modulators. In certain embodiments, at least one CFTR modulator is a CFTR corrector (e.g., VX-809, VX-661, VX-983 and GLPG2222) or potentiator (e.g., ivacaftor, genistein and GLPG1837). In certain of these embodiments, one of the at least two additional therapeutic agents is a CFTR corrector (e.g., VX-809, VX-661 and VX-983) and the other is a CFTR potentiator (e.g., ivacaftor and genistein). In certain of these embodiments, one of the at least two additional therapeutic agents is a CFTR corrector (e.g., GLPG2222) and the other is a CFTR potentiator (e.g., GLPG1837). In certain of these embodiments, one of the at least two additional therapeutic agents is a CFTR corrector (e.g., VX-809 or VX-661) and the other is a CFTR potentiator (e.g., ivacaftor). In certain of these embodiments, at least one CFTR modulator is an agent that enhances read-through of stop codons (e.g., NB 124 or ataluren).

Accordingly, in another aspect, this disclosure provides a method of treating a condition associated with deficient or decreased CFTR activity (e.g., cystic fibrosis), which includes administering to a subject in need thereof (e.g., a human patient in need thereof) an effective amount of a disclosed compound and at least one or two additional CFTR therapeutic agent(s) (e.g., at least one or two additional CFTR therapeutic agents, e.g., in which one of the at least one or two additional therapeutic agents is optionally a CFTR corrector or modulator (e.g., VX-809, VX-661, VX-983, GLPG2222, NB 124, ataluren) and/or the other is a CFTR potentiator (e.g., ivacaftor, genistein, and GLPG1837); e.g., one of the at least two additional therapeutic agents is GLPG2222, and the other is GLPG1837; or one of the at least two additional therapeutic agents is VX-809 or VX-661, and the other is a ivacaftor). In certain embodiments, the subject's CFTR genotype includes, without limitation, one or more Class I CFTR mutations, one or more Class II CFTR mutations, one or more Class III CFTR mutations, one or more Class IV CFTR mutations, or one or more Class V CFTR mutations, or one or more Class VI CFTR mutations. In certain embodiments, the subject's CFTR genotype includes, without limitation, one or more homozygote mutations (e.g., ΔF508/ΔF508 or R117H/R117H) and/or one or more compound heterozygote mutations (e.g., ΔF508/G551D; ΔF508/A455E; ΔF508/G542X; Δ508F/W1204X; R553X/W1316X; W1282X/N1303K; F508del/R117H; N1303K/3849+10kbC>T; ΔF508/R334W; DF508/G178R, and 591Δ18/E831X). In certain embodiments, the subject's CFTR genotype includes a Class I mutation, e.g., a G542X Class I mutation, e.g., a ΔF508/G542X compound heterozygous mutation. In other embodiments, the subject's CFTR genotype includes a Class III mutation, e.g., a G551D Class III mutation, e.g., a ΔF508/G551D compound heterozygous mutation. In still other embodiments, the subject's CFTR genotype includes a Class V mutation, e.g., a A455E Class V mutation, e.g., a ΔF508/A455E compound heterozygous mutation. In certain embodiments, ΔF508 CFTR activity and/or G542X CFTR activity and/or G551D CFTR activity and/or A455E activity is enhanced (e.g., increased). In certain embodiments, the enhancement in activity (e.g., increase in activity) provided by the combination of the disclosed compound and one or two additional therapeutic agents is greater than additive when compared to the enhancement in activity provided by each therapeutic component individually.

| Class | Effect on CFTR protein | Example of mutation |
|---|---|---|
| I | Shortened protein | W1282X Instead of inserting the amino acid tryptophan (W), the protein sequence is prematurely stopped (indicated by an X). |

-continued

| Class | Effect on CFTR protein | Example of mutation |
|---|---|---|
| II | Protein fails to reach cell membrane | ΔF508 A phenylalanine amino acid (F) is deleted |
| III | Channel cannot be regulated properly | G551D A "missense" mutation: instead of a glycine amino acid (G), aspartate (D) is added |
| IV | Reduced chloride conductance | R117H Missense |
| V | Reduced due to incorrect splicing of gene | 3120 + 1G > A Splice-site mutation in gene intron 16 |
| VI | Reduced due to protein instability | N287Y a A → T at 991 |

| Genotype | Description | Possible Symptoms |
|---|---|---|
| Δ508F/Δ508F | homozygote | Severe lung disease, pancreatic insufficient |
| R117H/R117H | homozygote | Congenital bilateral absence of the vas deferens, No lung or pancreas disease |
| WT/Δ508F | heterozygote | Unaffected |
| WT/3120 + 1 G > A | heterozygote | Unaffected |
| Δ508F/W1204X | compound heterozygote | pancreatic insufficient |
| R553X and W1316X | compound heterozygote | Mild lung disease, pancreatic insufficient |
| 591Δ18/E831X | compound heterozygote | No lung or pancreas disease, nasal polyps |

For example, provided herein is a method of treating a patient having one or more of the following mutations in the CFTR gene: G1244E, G1349D, G178R, G551S, S1251N, S1255P, 5549N, S549R, G970R, or R117H, and/or e.g., a patient with one or two copies of the F508del mutation, or one copy of the ΔF508 mutation and a second mutation that results in a gating effect in the CFTR protein (e.g., a patient that is heterozygous for ΔF508 and G551D mutation), a patient with one copy of the ΔF508 mutation and a second mutation that results in residual CFTR activity, or a patient with one copy of the ΔF508 mutation and a second mutation that results in residual CFTR activity, comprising administering an effective amount of a disclosed compound. As described herein, such exemplary methods (e.g., of a patient having one or mutations such as those described above) may include, for example, administering to such patient a combination therapy, e.g., administering (simultaneously or sequentially) an effective amount of ivacaftor to said patient and an effective amount of disclosed compound that may act as an amplifier. Such administration may result, for example, in increased chloride transport in human bronchial epithelial cells with e.g., one or two copies of mutations, e.g., ΔF508 mutation, as compared to administration of ivacaftor alone. Another combination therapy that includes a disclosed compound may also include an effective amount of a read through agent (e.g., ataluren, NB 124) and an effective amount of disclosed compound that may act as an amplifier.

The phrase "combination therapy," as used herein, refers to an embodiment where a patient is co-administered a disclosed compound, a CFTR potentiator agent (e.g., ivacaftor) and optionally, one or more CFTR corrector agent(s) (e.g., VX-661 and/or lumacaftor) as part of a specific treatment regimen intended to provide the beneficial effect from the co-action of these therapeutic agents. For example, a beneficial effect of a combination may include, but is not limited to, pharmacokinetic or pharmacodynamic co-action resulting from the combination of therapeutic agents. For example, administration of a disclosed compound with ivacaftor alone or with a CFTR corrector agent (e.g., lumacaftor or VX-661) may result in a level of function (e.g., as measured by chloride activity in HBE cells or patients that have a ΔF508 mutation, that achieves clinical improvement (or better) as compared to the chloride activity level in cells or patients with a G551D mutation receiving ivacaftor alone, or ivacaftor and a corrector agent (lumacaftor or VX-661; or for example, administration of a disclosed compound with ivacaftor alone or ivacaftor with a CFTR corrector agent (e.g., lumacaftor or VX-661) may result in a level of function (e.g., as measured by chloride activity in HBE cells or patients that have a A455E mutation, that achieves clinical improvement (or better) as compared to the chloride activity level at e.g., 50% or more of wild type cells; or upon administration of a disclosed compound and ivacaftor to a patient (e.g. having a G551D class III mutation) may show e.g., about two times or more improved activity of ivacaftor as compared to administration of ivacaftor alone. Administration of disclosed therapeutic agents in combination typically is carried out over a defined time period (usually a day, days, weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single tablet or capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, inhalational routes, intravenous routes, intramuscular routes, and direct absorption through mucous membrane tissues. The therapeutic agents can be administered by the same route or by different routes. For example, a first therapeutic agent of the combination selected may be administered by intravenous injection or inhalation or nebulizer while the other therapeutic agents of the combination may be administered orally. Alternatively, for example, all therapeutic agents may be administered orally or all therapeutic agents may be administered by intravenous injection, inhalation or nebulization.

Combination therapy also can embrace the administration of the therapeutic agents as described above in further combination with other biologically active ingredients and non-drug therapies. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by a day, days or even weeks.

The components of a disclosed combination may be administered to a patient simultaneously or sequentially. It will be appreciated that the components may be present in the same pharmaceutically acceptable carrier and, therefore, are administered simultaneously. Alternatively, the active ingredients may be present in separate pharmaceutical carriers, such as, conventional oral dosage forms, that can be administered either simultaneously or sequentially.

In a further aspect, a method of identifying a candidate agent that increases CFTR activity is provided, which includes: (i) contacting a cell that expresses a CFTR protein with the candidate agent and a disclosed compound; (ii) measuring the CFTR activity in the cell in the presence of the candidate agent and the disclosed compound; and (iii) comparing the CFTR activity to that in the absence of the test agent, wherein an increase in CFTR activity in the presence of the test agent indicates that the agent increases CFTR activity. In certain embodiments, the cell expresses a mutant CFTR protein. In certain embodiments, CFTR activity is measured by measuring chloride channel activity of the CFTR, and/or other ion transport activity. In certain of these embodiments, the method is high-throughput. In certain of these embodiments, the candidate agent is a CFTR corrector or a CFTR potentiator.

The term "pharmaceutically acceptable salt(s)" as used herein refers to salts of acidic or basic groups that may be present in a disclosed compounds used in disclosed compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

Also included in the present invention are methods that include administering a prodrug of compound described herein, for example, prodrugs of a compound of Formula (I) or a pharmaceutical composition thereof or method of use of the prodrug.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as $(C_{1-8})$alkyl, $(C_{2-12})$alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_{1-2})$alkylamino$(C_{2-3})$alkyl (such as β-dimethylaminoethyl), carbamoyl-$(C_{1-2})$alkyl, N,N-di$(C_{1-2})$alkylcarbamoyl-$(C_{1-2})$alkyl and piperidino-, pyrrolidino- or morpholino$(C_{2-3})$alkyl.

Similarly, if a compound of the invention contains an alcohol functional group, a prodrug can be formed by the replacement of the hydrogen atom of the alcohol group with a group such as $(C_{1-6})$alkylcarbonyloxymethyl, 1-(($C_{1-6}$)alkylcarbonyloxy)ethyl, 1-methyl-1-$(C_{1-6})$alkylcarbonyloxy)ethyl $(C_{1-6})$alkoxycarbonyloxymethyl, N—$(C_{1-6})$alkoxycarbonylaminomethyl, succinoyl, $(C_{1-6})$alkylcarbonyl, α-amino$(C_{1-4})$alkylcarbonyl, arylalkylcarbonyl and α-aminoalkylcarbonyl, or α-aminoalkylcarbonyl-α-aminoalkylcarbonyl, where each α-aminoalkylcarbonyl group is independently selected from the naturally occurring L-amino acids, $P(O)(OH)_2$, —$P(O)(O(C_{1-6})$alkyl$)_2$or glycosyl (the radical resulting from the removal of a hydroxyl group of the hemiacetal form of a carbohydrate).

If a compound of the invention incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplício, et al., *Molecules* 2008, 13, 519 and references therein The invention additionally includes use of clathrates of compounds described herein, pharmaceutical compositions comprising the clathrates, and methods of use of the clathrates. In some embodiments, the invention is directed to clathrates of a compound of Formula (I) or a pharmaceutical composition thereof.

As discussed above, the disclosure contemplates administration of pharmaceutical compositions comprising a pharmaceutically acceptable carrier or excipient and a compound described herein. A disclosed compound, or a pharmaceutically acceptable salt, solvate, clathrate or prodrug thereof, can be administered in pharmaceutical compositions comprising a pharmaceutically acceptable carrier or excipient. The excipient can be chosen based on the expected route of administration of the composition in therapeutic applications. The route of administration of the composition depends on the condition to be treated. For example, intravenous injection may be preferred for treatment of a systemic disorder and oral administration may be preferred to treat a gastrointestinal disorder. The route of administration and the dosage of the composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. A pharmaceutical composition comprising a disclosed compound or a pharmaceutically acceptable salt, solvate, clathrate or prodrug, can be administered by a variety of routes including, but not limited to, parenteral, oral, pulmonary, ophthalmic, nasal, rectal, vaginal, aural, topical, buccal, transdermal, intravenous, intramuscular, subcutaneous, intradermal, intraocular, intracerebral, intralymphatic, intraarticular, intrathecal and intraperitoneal. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the pharmacologic agent or composition. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Pharmaceutical compositions can also include large, slowly metabolized macromolecules such as proteins, polysaccharides such as chitosan, polylactic acids, polyglycolic acids and copolymers (such as latex functionalized SEPHAROSE™, agarose, cellulose, and the like), polymeric amino acids, amino acid copolymers, and lipid aggregates (such as oil droplets or liposomes).

The compositions can be administered parenterally such as, for example, by intravenous, intramuscular, intrathecal or subcutaneous injection. Parenteral administration can be accomplished by incorporating a composition into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Injectable formulations can be prepared either as liquid solutions or suspensions; solid forms suitable for solution in, or suspension in, liquid vehicles prior to injection can also be prepared. The preparation also can also be emulsified or encapsulated in liposomes or micro particles such as polylactide, polyglycolide, or copolymer for enhanced adjuvant effect, as discussed above [Langer, *Science* 249: 1527, 1990 and Hanes, *Advanced Drug Delivery Reviews* 28: 97-119, 1997]. The compositions and pharmacologic agents described herein can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, transdermal applications and ocular delivery. For suppositories, binders and carriers include, for example, polyalkylene glycols or triglycerides; such suppositories can be formed from mixtures containing the active ingredient in the range of about 0.5% to about 10%, preferably about 1% to about 2%. Oral formulations include excipients, such as pharmaceutical grades of mannitol, lactose, starch, magnesium stearate, sodium saccharine, cellulose, and magnesium carbonate. Topical application can result in transdermal or intradermal delivery. Transdermal delivery can be achieved using a skin patch or using transferosomes. [Paul et al., *Eur. J. Immunol.* 25: 3521-24, 1995; Cevc et al., *Biochem. Biophys. Acta* 1368: 201-15, 1998].

For the purpose of oral therapeutic administration, the pharmaceutical compositions can be incorporated with excipients and used in the form of tablets, troches, capsules, elixirs, suspensions, syrups, wafers, chewing gums and the like. Tablets, pills, capsules, troches and the like may also contain binders, excipients, disintegrating agent, lubricants, glidants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and non-toxic in the amounts used. In another embodiment, the composition is administered as a tablet or a capsule.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor, and the like. For vaginal administration, a pharmaceutical composition may be presented as pessaries, tampons, creams, gels, pastes, foams or spray.

The pharmaceutical composition can also be administered by nasal administration. As used herein, nasally administering or nasal administration includes administering the composition to the mucus membranes of the nasal passage or nasal cavity of the patient. As used herein, pharmaceutical compositions for nasal administration of a composition include therapeutically effective amounts of the compounds prepared by well-known methods to be administered, for example, as a nasal spray, nasal drop, suspension, gel, ointment, cream or powder. Administration of the composition may also take place using a nasal tampon or nasal sponge.

For topical administration, suitable formulations may include biocompatible oil, wax, gel, powder, polymer, or other liquid or solid carriers. Such formulations may be administered by applying directly to affected tissues, for example, a liquid formulation to treat infection of conjunctival tissue can be administered dropwise to the subject's eye, or a cream formulation can be administered to the skin.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120°C., dissolving the pharmaceutical composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

In addition to the usual meaning of administering the formulations described herein to any part, tissue or organ whose primary function is gas exchange with the external environment, for purposes of the present invention, "pulmonary" will also mean to include a tissue or cavity that is contingent to the respiratory tract, in particular, the sinuses. For pulmonary administration, an aerosol formulation containing the active agent, a manual pump spray, nebulizer or pressurized metered-dose inhaler as well as dry powder formulations are contemplated. Suitable formulations of this type can also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the compound intended for pulmonary administration is dissolved, suspended or emulsified in a mixture of a solvent, surfactant and propellant. The mixture is maintained under pressure in a canister that has been sealed with a metering valve.

The invention also encompasses the treatment of a condition associated with a dysfunction in proteostasis in a subject comprising administering to said subject an effective amount of a disclosed compound that enhances, improves or restores proteostasis of a protein. Proteostasis refers to protein homeostasis. Dysfunction in protein homeostasis is a result of protein misfolding, protein aggregation, defective protein trafficking or protein degradation. For example, the invention encompasses administering a compound of e.g., Formula (I) that corrects protein misfolding, reduces protein aggregation, corrects or restores protein trafficking and/or affects protein degradation for the treatment of a condition associated with a dysfunction in proteostasis. In some aspects of the invention, a compound of e.g., Formula (I) that corrects protein misfolding and/or corrects or restores protein trafficking is administered. In cystic fibrosis, the mutated or defective enzyme is the cystic fibrosis transmembrane conductance regulator (CFTR). One of the most common mutations of this protein is ΔF508 which is a deletion (Δ) of three nucleotides resulting in a loss of the amino acid phenylalanine (F) at the 508th (508) position on the protein. As described above, mutated cystic fibrosis transmembrane conductance regulator exists in a misfolded state and is characterized by altered trafficking as compared to the wild type CFTR. Additional exemplary proteins of which there can be a dysfunction in proteostasis, for example that can exist in a misfolded state, include, but are not limited to, glucocerebrosidase, hexosamine A, aspartylglucsaminidase, α-galactosidase A, cysteine transporter, acid ceremidase, acid α-L-fucosidase, protective protein, cathepsin A, acid β-glucosidase, acid β-galactosidase, iduronate 2-sulfatase, α-L-iduronidase, galactocerebrosidase, acid α-mannosidase, acid β-mannosidase, arylsulfatase B, arylsulfatase A, N-acetylgalactosamine-6-sulfate sulfatase, acid β-galactosidase, N-acetylglucosamine-1-phosphotransferase, acid sphingmyelinase, NPC-1, acid α-glucosidase, β-hexosamine B, heparin N-sulfatase, α-N-acetylglucosaminidase, α-glucosaminide N-acetyltransferase, N-acetylglucosamine-6-sulfate sulfatase, α-N-acetylgalactosaminidase, α-neuramidase, β-glucuronidase, β-hexosamine A and acid lipase, polyglutamine, α-synuclein, TDP-43, superoxide dismutase (SOD), Aβ peptide, tau protein, transthyretin and insulin. Disclosed compounds for example, in some embodiments, may be used to restore proteostasis (e.g., correct folding and/or alter trafficking) of the proteins described above.

Protein conformational diseases encompass gain of function disorders and loss of function disorders. In one embodiment, the protein conformational disease is a gain of function disorder. The terms "gain of function disorder," "gain of function disease," "gain of toxic function disorder" and "gain of toxic function disease" are used interchangeably herein. A gain of function disorder is a disease characterized by increased aggregation-associated proteotoxicity. In these diseases, aggregation exceeds clearance inside and/or outside of the cell. Gain of function diseases include, but are not limited to, neurodegenerative diseases associated with aggregation of polyglutamine, Lewy body diseases, amyotrophic lateral sclerosis, transthyretin-associated aggregation diseases, Alzheimer's disease, Machado-Joseph disease, cerebral B-amyloid angiopathy, retinal ganglion cell degeneration, tauopathies (progressive supranuclear palsy, corticobasal degeneration, frontotemporal lobar degeneration), cerebral hemorrhage with amyloidosis, Alexander disease, Serpinopathies, familial amyloidotic neuropathy, senile systemic amyloidosis, ApoAI amyloidosis, ApoAII amyloidosis, ApoAIV amyloidosis, familial amyloidosis of the Finnish type, lysoyzme amyloidosis, fibrinogen amyloidosis, dialysis amyloidosis, inclusion body myositis/myopathy, cataracts, medullary thyroid carcinoma, cardiac atrial amyloidosis, pituitary prolactinoma, hereditary lattice corneal dystrophy, cutaneous lichen amyloidosis, corneal lactoferrin amyloidosis, corneal lactoferrin amyloidosis, pulmonary alveolar proteinosis, odontogenic tumor amyloid, seminal vesical amyloid, sickle cell disease, critical illness myopathy, von Hippel-Lindau disease, spinocerebellar ataxia 1, Angelman syndrome, giant axon neuropathy, inclusion body myopathy with Paget disease of bone, frontotemporal dementia (IBMPFD) and prion diseases. Neurodegenerative diseases associated with aggregation of polyglutamine include, but are not limited to, Huntington's disease, dentatorubral and pallidoluysian atrophy, several forms of spino-cerebellar ataxia, and spinal and bulbar muscular atrophy. Alzheimer's disease is characterized by the formation of two types of aggregates: extracellular aggregates of Aβ peptide and intracellular aggregates of the microtubule associated protein tau. Transthyretin-associated aggregation diseases include, for example, senile systemic amyloidoses and familial amyloidotic neuropathy. Lewy body diseases are characterized by an aggregation of α-synuclein protein and include, for example, Parkinson's disease, lewy body dementia (LBD) and multiple system atrophy (SMA). Prion diseases (also known as transmissible spongiform encephalopathies or TSEs) are characterized by aggregation of prion proteins. Exemplary human prion diseases are Creutzfeldt-Jakob Disease (CJD), Variant Creutzfeldt-Jakob Disease, Gerstmann-Straussler-Scheinker Syndrome, Fatal Familial Insomnia and Kuru. In another embodiment, the misfolded protein is alpha-1 anti-trypsin.

In a further embodiment, the protein conformation disease is a loss of function disorder. The terms "loss of function disease" and "loss of function disorder" are used interchangeably herein. Loss of function diseases are a group of diseases characterized by inefficient folding of a protein resulting in excessive degradation of the protein. Loss of function diseases include, for example, lysosomal storage diseases. Lysosomal storage diseases are a group of diseases characterized by a specific lysosomal enzyme deficiency which may occur in a variety of tissues, resulting in the build-up of molecules normally degraded by the deficient enzyme. The lysosomal enzyme deficiency can be in a lysosomal hydrolase or a protein involved in the lysosomal trafficking. Lysosomal storage diseases include, but are not limited to, aspartylglucosaminuria, Fabry's disease, Batten disease, Cystinosis, Farber, Fucosidosis, Galactasidosialidosis, Gaucher's disease (including Types 1, 2 and 3), Gm1 gangliosidosis, Hunter's disease, Hurler-Scheie's disease, Krabbe's disease, α-Mannosidosis, β-Mannosidosis, Maroteaux-Lamy's disease, Metachromatic Leukodystrophy, Morquio A syndrome, Morquio B syndrome, Mucolipidosis II, Mucolipidosis III, Neimann-Pick Disease (including Types A, B and C), Pompe's disease, Sandhoff disease, Sanfilippo syndrome (including Types A, B, C and D), Schindler disease, Schindler-Kanzaki disease, Sialidosis, Sly syndrome, Tay-Sach's disease and Wolman disease.

In another embodiment, a disease associated with a dysfunction in proteostasis is a cardiovascular disease. Cardiovascular diseases include, but are not limited to, coronary artery disease, myocardial infarction, stroke, restenosis and arteriosclerosis. Conditions associated with a dysfunction of proteostasis also include ischemic conditions, such as, ischemia/reperfusion injury, myocardial ischemia, stable angina, unstable angina, stroke, ischemic heart disease and cerebral ischemia.

In yet another embodiment, the disease associated with a dysfunction in proteostasis is diabetes and/or complications of diabetes, including, but not limited to, diabetic retinopathy, cardiomyopathy, neuropathy, nephropathy, and impaired wound healing.

In a further embodiment, the disease associated with a dysfunction in proteostasis is an ocular disease including, but not limited to, age-related macular degeneration (AMD), diabetic macular edema (DME), diabetic retinopathy, glaucoma, cataracts, retinitis pigmentosa (RP) and dry macular degeneration.

In yet additional embodiments, a disclosed method is directed to treating a disease associated with a dysfunction in proteostasis, wherein the disease affects the respiratory system or the pancreas comprising administering a disclosed compound In certain additional embodiments, a disclosed method encompass treating a condition selected from the group consisting of polyendocrinopathy/hyperinsulinemia, diabetes mellitus, Charcot-Marie Tooth syndrome, Pelizaeus-Merzbacher disease, and Gorham's Syndrome comprising administering a disclosed compound.

Additional conditions associated with a dysfunction of proteostasis include hemoglobinopathies, inflammatory diseases, intermediate filament diseases, drug-induced lung damage and hearing loss. Methods for the treatment of hemoglobinopathies (such as sickle cell anemia), an inflammatory disease (such as inflammatory bowel disease, colitis, ankylosing spondylitis), intermediate filament diseases (such as non-alcoholic and alcoholic fatty liver disease) and drug induced lung damage (such as methotrexate-induced lung damage) are also contemplated herein. In other embodiments, methods for treating hearing loss, such as noise-induced hearing loss, aminoglycoside-induced hearing loss, and cisplatin-induced hearing loss comprising administering disclosed compounds are provided herein.

Additional conditions include those associated with a defect in protein trafficking and that can be treated according to disclosed methods include: PGP mutations, hERG trafficking mutations, nephrongenic diabetes insipidus mutations in the arginine-vasopressin receptor 2, persistent hyperinsulinemic hypoglycemia of infancy (PHH1) mutations in the sulfonylurea receptor 1, and α1AT.

The disclosure is illustrated by the following examples which are not meant to be limiting in any way.

EXEMPLIFICATION

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "intermediates" herein are contemplated as compounds of the invention.

Example 1

N-(3-(5-methyl-1,3,4-thiadiazol-2-yl)propyl)-5-phenylisoxazole-3-carboxamide

Step 1: 4-(1,3-Dioxo-1,3-dihydro-isoindol-2-yl)-butyric acid: A mixture of phthalic anhydride (10 g, 0.067 mol) and 4-amino-butyric acid (9.35 g, 0.0814 mol) was heated at 155° C. for 5 h. The reaction mixture was diluted with hot water (400 mL), solids were collected by filtration and dried to afford the product (14 g, 89%) as a white solid. $^1$H NMR (400 MHz, CDCl$_3$): δ 7.86-7.82 (m, 2H), 7.73-7.69 (m, 2H), 3.77-3.74 (t, 2H), 2.43-2.39 (t, 2H), 2.04-1.97 (m, 2H); LCMS [M−H]$^+$=232.1.

Step 2: N'-acetyl-4-(1,3-dioxoisoindolin-2-yl)butane hydrazide: Acetohydrazide (0.76 g, 0.012 mol), EDC.HCl (2.53 g, 0.0127 mol), HOBt (1.41 g, 0.0102 mol) and TEA (2.56 g, 0.0255 mol) were added to a solution of 4-(1,3-Dioxo-1,3-dihydro-isoindol-2-yl)-butyric acid (2.0 g, 0.0085 mol) in THF (30 mL) at room temperature and the mixture was stirred for 13 h. Volatiles were removed under vacuum, diluted with ice-water and extracted with EtOAc (3×150 mL). Combined organic layers were dried over anhydrous sodium sulfate and evaporated under vacuum to afford the crude product. The crude was triturated with DCM and dried to afford the product (1.4 g, 56%) as an off-white solid. $^1$H NMR (400 MHz, DMSO d$_6$): δ 9.72-9.68 (m, 2H), 7.89-7.82 (m, 4H), 3.61-3.57 (t, 2H), 2.17-2.13 (t, 2H), 1.85-1.78 (m, 5H); [M+H]$^+$=290.0.

Step 3: 2-[3-(5-Methyl-[1,3,4]thiadiazol-2-yl)-propyl]-isoindole-1,3-dione: A mixture of N'-acetyl-4-(1,3-dioxoisoindolin-2-yl)butane hydrazide (1 g, 0.003 mol) and Lawesson's reagent (2.1 g, 0.0055 mol) in 1,4-Dioxane (20 mL) was heated at 100° C. for 8 h. Volatiles were removed under vacuum and purified by column chromatography on neutral alumina eluted with 0.1% MeOH in DCM to afford the compound (0.75 g, 75%); $^1$H NMR (400 MHz, DMSO d$_6$): δ 7.86-7.82 (m, 4H), 3.69-3.65 (t, 2H), 3.10-3.07 (t, 2H), 2.64 (s, 3H), 2.08-2.00 (m, 2H); LCMS [M+H]$^+$ 288.1.

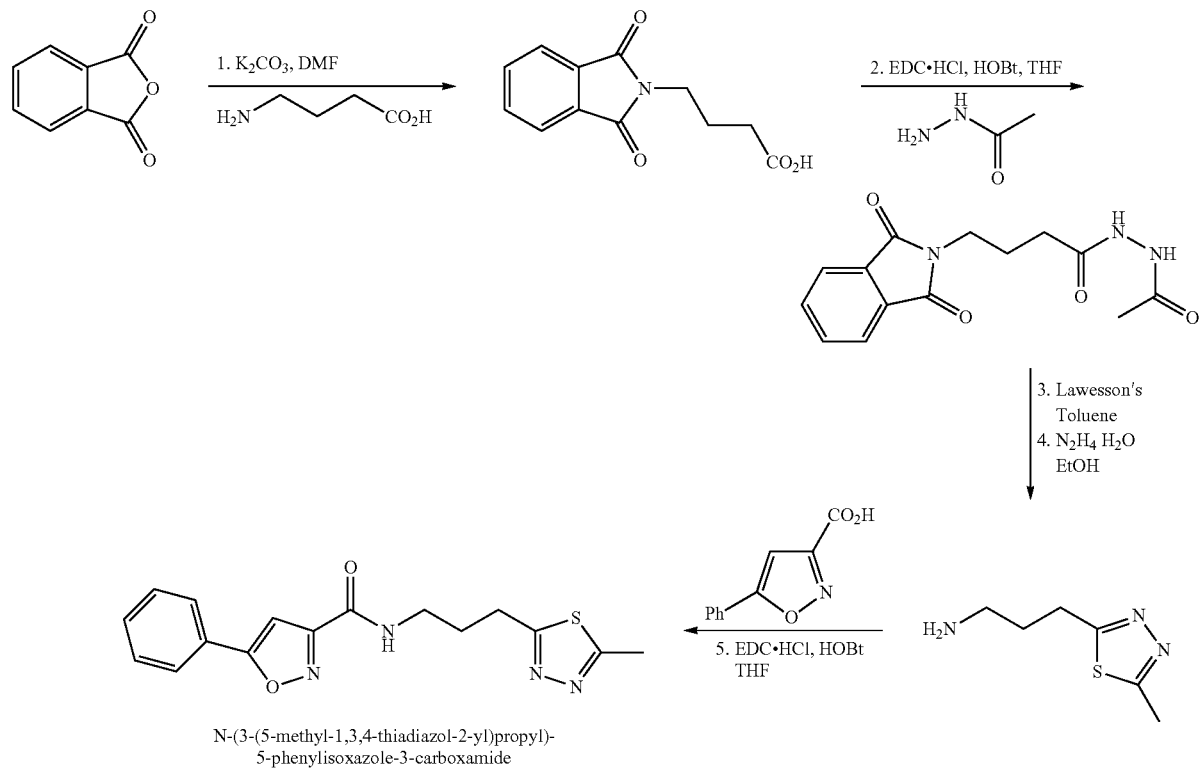

N-(3-(5-methyl-1,3,4-thiadiazol-2-yl)propyl)-5-phenylisoxazole-3-carboxamide

Step 4: 3-(5-methyl-1,3,4-thiadiazol-2-yl)propan-1-amine: A solution of 2-[3-(5-methyl-[1,3,4]thiadiazol-2-yl)-propyl]-isoindole-1,3-dione (0.5 g, 0.0017 mol) in ethanol and hydrazine hydrate (0.17 g, 0.00352 mol) was refluxed for 2 h. After completion, solid was removed by filtration and the filtrate was evaporated to obtain crude product (0.35 g crude); LC-MS: [M+H]$^+$ 157.9. The crude was used for next step without purification.

Step 5: N-(3-(5-methyl-1,3,4-thiadiazol-2-yl)propyl)-5-phenylisoxazole-3-carboxamide: A solution of 5-phenylisoxazole-3-carboxylic acid (0.30 g, 0.0015 mol), 3-(5-methyl-1,3,4-thiadiazol-2-yl)propan-1-amine (0.30 g, 0.0019 mol), EDC-HCl (0.45 g, 0.0027 mol), HOBt (0.25 g, 0.0019 mol) and TEA (0.48 g 0.0048 mol) in THF (20 mL) at room temperature was stirred for 13 h. Volatiles were removed under vacuum, diluted with ice-water and extracted with EtOAc (3×50 mL). Combined organic layers was dried over anhydrous sodium sulfate and concentrated under vacuum to afford crude product. The crude was purified by column chromatography on neutral alumina eluted with 30% Ethyl Acetate in Hexane to afford compound.

Yield: 34%; Appearance: white solid

Analytical data: $^1$H NMR (400 MHz, CDCl$_3$): δ 7.80-7.77 (m, 2H), 7.50-7.45 (m, 3H), 7.06 (m, 1H), 6.94 (s, 1H), 3.60-3.55 (t, 2H), 3.18-3.15 (t, 2H), 2.73 (s, 3H), 2.19-2.12 (m, 2H);

LCMS [M+H]$^+$ 329.3; HPLC Purity: 98.8% at 200 nm, 97.14% at 220 nm.

Example 2

N-(2-(5-(methoxymethyl)-1,3,4-thiadiazol-2-yl)ethyl)-5-phenylisoxazole-3-carboxamide

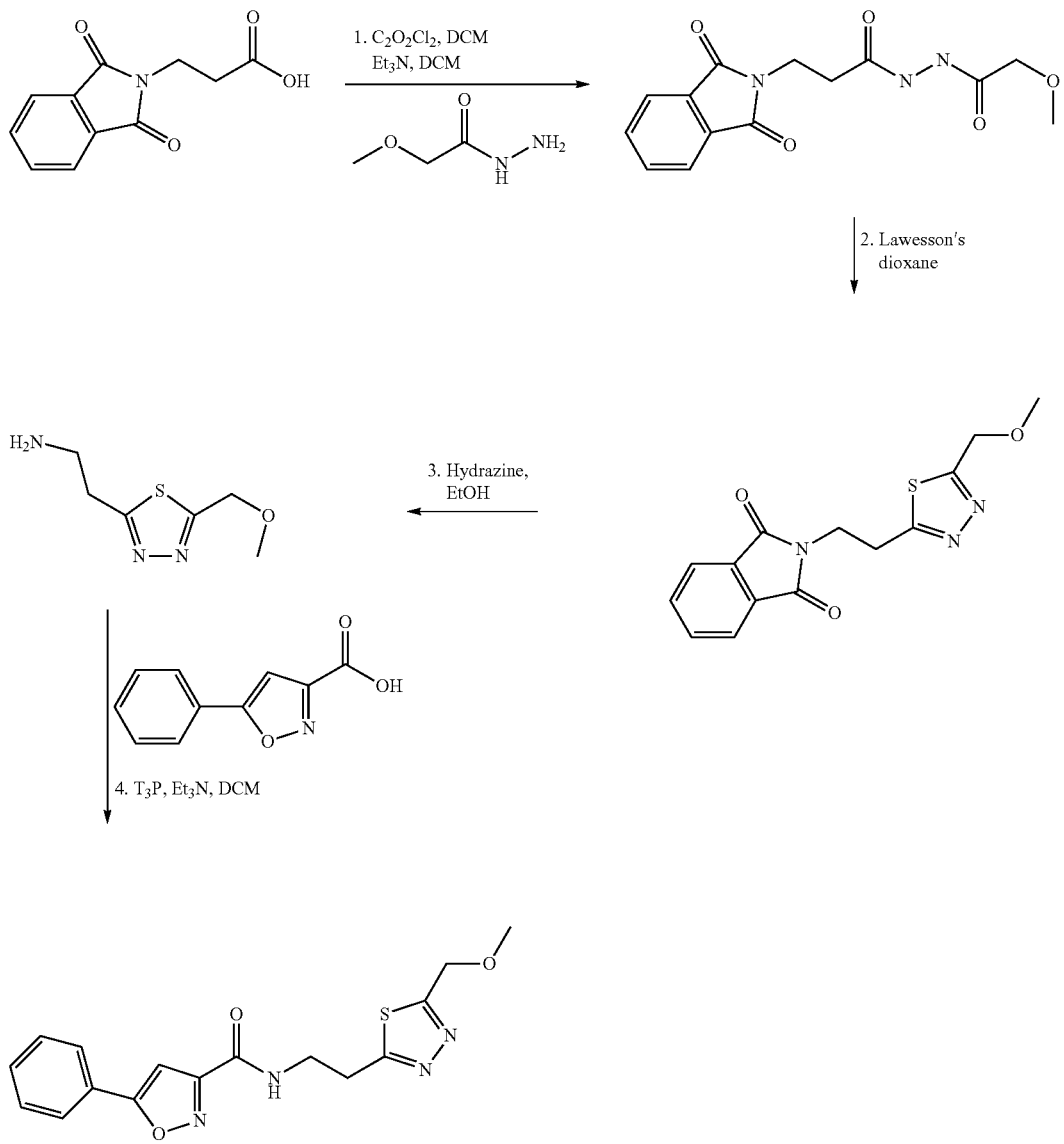

Step-1: 3-(1,3-dioxoisoindolin-2-yl)-N'-(2-methoxyacetyl)propanehydrazide: Oxalyl chloride (27.47 g, 0.216 mol) was added slowly to an ice-cooled solution of 3-(1,3-dioxoisoindolin-2-yl) propanoic acid (15.80 g, 0.072 mol) in DCM (250 mL) followed by catalytic DMF (0.5 mL). The reaction mixture was stirred at room temperature for 1 h and volatiles were removed completely under vacuum to obtain the intermediate acid chloride as a yellow solid. A solution of 2-methoxyacetohydrazide (2, 9.01 g, 0.086 mol) in DCM (50 mL) was added to a solution of this acid chloride in DCM (200 mL) at 0° C. followed by triethylamine (60.5 g, 0.597 mol). The resultant reaction mixture was stirred at room temperature for 1 h. The resulting yellow suspension was quenched onto crushed ice (200 mL). Separated organic layer was washed with water (2×200 mL), brine (150 mL) and concentrated under vacuum to afford crude product (5 g). The aqueous layer which also contains desired product was concentrated under reduced pressure to afford a solid residue. The crude residue was dried and extracted sequentially with THF (1000 mL), acetone (300 mL) and acetonitrile (400 mL). The combined organic layer was concentrated to obtain yellow semisolid (37 g) which was combined with solid residue (5 g) from organic layer and was used in the next reaction without purification. LC-MS [M+H]$^+$ 306.1 m/z.

Step-2: 2-[2-(5-methoxymethyl-[1,3,4]thiadiazol-2-yl)-ethyl]-isoindole-1,3-dione: A mixture of crude 3-(1,3-dioxoisoindolin-2-yl)-N'-(2-methoxyacetyl)propanehydrazide (42 g crude) and Lawesson's reagent (44 g, 0.11 mol) in 1,4-dioxane (250 mL) was heated to 100° C. for 18 h. The reaction was cooled to room temperature, filtered through a celite bed and the precipitate was washed with 1,4-dioxane (200 mL). Filtrate was concentrated under reduced pressure and the crude residue was partitioned between ice-water (400 mL) and EtOAc (800 mL). Combined organic layer was concentrated under reduced pressure to obtain a brown sticky mass. The brown mass was subjected to column chromatography on neutral alumina using 1% MeOH in DCM as eluant to afford material (5.40 g) as brown oil. LC-MS [M+H]$^+$=304.1.

Step-3: 2-(5-methoxymethyl-[1,3,4]thiadiazol-2-yl)-ethylamine: A mixture of impure 2-[2-(5-methoxymethyl-[1,3,4]thiadiazol-2-yl)-ethyl]-isoindole-1,3-dione (5.40 g crude) and hydrazine monohydrate (6.3 mL, 0.126 mol) in absolute ethanol (100 mL) was refluxed for 13 h. The reaction mixture was cooled to room temperature and the solid precipitated was filtered and washed with cold ethanol. Filtrate was concentrated under vacuum to obtain an oily crude product as brown oil. The crude product was chromatographed on basic alumina using 1% MeOH in DCM as eluant to obtain the compound (1.88 g, 61%) as pale brown oil. $^1$H NMR (400 MHz, CDCl$_3$): δ 4.81 (s, 2H), 3.45 (s, 3H), 3.27-3.23 (m, 2H), 3.20-3.16 (m, 2H); LC-MS [M+H]$^+$ 174.1 m/z.

Step-4: N-(2-(5-(methoxymethyl)-1,3,4-thiadiazol-2-yl) ethyl)-5-phenylisoxazole-3-carboxamide: To an ice-cooled suspension of 5-phenyl-isoxazole-3-carboxylic acid (2.08 g, 0.011 mol) in DCM (40 mL) was slowly added T$_3$P solution (10.5 mL, 0.016 mol, 50% solution in EtOAc) followed by addition of triethylamine (2.23 g, 0.022 mol) and solution of 2-(5-methoxymethyl-[1,3,4]thiadiazol-2-yl)-ethylamine (1.88 g, ca. 0.011 mol) in DCM (10 mL). The reaction mixture was stirred at room temperature for 18 h and quenched onto ice-water (150 mL). Separated DCM layer was washed with saturated NaHCO$_3$ solution (3×75 mL), water (2×50 mL) and brine (100 mL). Organic layer was dried over anhydrous Na$_2$SO$_4$ and concentrated under vacuum to obtained crude solid product. The crude solid was triturated in diethyl ether (50 mL), filtered and dried to afford desired product.

Yield: 48%; Appearance: off-whites solid

Analytical data: $^1$H NMR (400 MHz, CDCl$_3$): δ 7.79-7.76 (m, 2H), 7.50-7.46 (m, 3H), 7.41 (br, 1H), 6.93 (s, 1H), 4.82 (s, 2H), 3.99-3.94 (m, 2H), 3.45 (s, 3H), 3.42-3.41 (m, 2H).

LC-MS: (M+H)$^+$ 345.0; HPLC Purity: 99.87% at 254 nm & 99.32% at 220 nm.

Examples 3 and 4

N-(2-(5-(hydroxymethyl)-1,3,4-thiadiazol-2-yl) ethyl)-5-phenylisoxazole-3-carboxamide

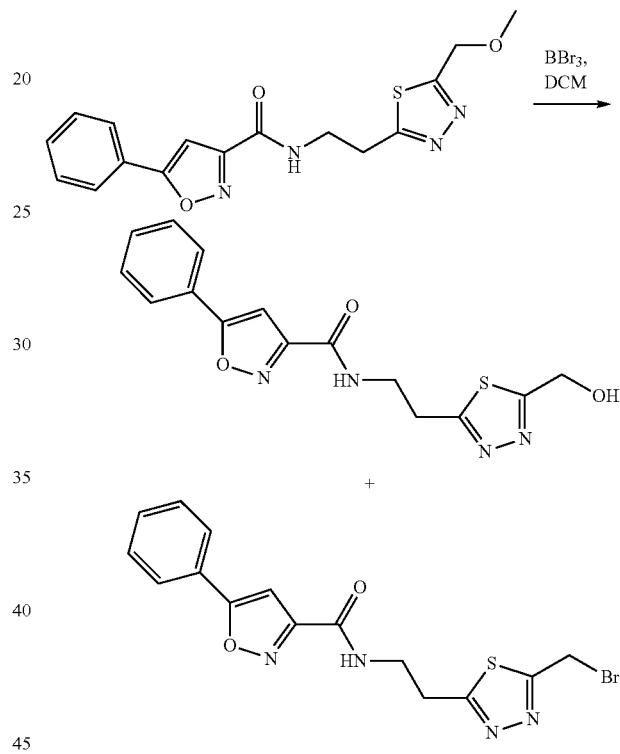

BBr$_3$ solution (0.73 g, 0.0029 mol, 1.0 M solution in DCM) was added slowly to a solution of N-(2-(5-(methoxymethyl)-1,3,4-thiadiazol-2-yl)ethyl)-5-phenylisoxazole-3-carboxamide (1.3 g, 0.0029 mol) in DCM (30 mL) at −78° C. The reaction was slowly allowed to stir at room temperature for 2 h. It was quenched with KOH (212 mg, 3.48m mol) solution in water (30 mL). Separated organic layer was dried over Na$_2$SO$_4$ and concentrated under vacuum to obtain crude as a pale yellow solid. The crude was chromatographed on neutral alumina using 30 to 80% EtOAc in hexane afforded two products:

Step 1: N-(2-(5-(hydroxymethyl)-1,3,4-thiadiazol-2-yl) ethyl)-5-phenylisoxazole-3-carboxamide: Yield: 12%; appearance: off white solid Analytical data: $^1$H NMR (400 MHz, DMSO d6): δ 9.05-9.02 (t, J=5.7 Hz, 1H), 7.95-7.92 (m, 2H), 7.58-7.52 (m, 3H), 7.37 (s, 1H), 6.14 (t, J=5.9 Hz, 1H), 4.80 (d, J=5.96 Hz, 2H), 3.66 (m, 2H), 3.37-3.33 (m, 2H).

LC-MS [M+H]$^+$=331.0; HPLC Purity: 97.36% at 220 nm and 98.50% at 254 nm.

Step 2: N-(2-(5-(bromomethyl)-1,3,4-thiadiazol-2-yl)ethyl)-5-phenylisoxazole-3-carboxamide: Yield: 9%; Appearance: white solid Analytical data: ¹H NMR (400 MHz, CDCl₃): δ 7.79-7.77 (m, 2H), 7.49-7.47 (m, 3H), 7.40 (br, 1H), 6.94 (s, 1H), 4.77 (s, 2H), 3.97 (q, J=6.3 Hz, 2H), 3.42 (t, J=6.3 Hz, 2H).

LC-MS [M+H]$^+$=393.1 & 395.0; HPLC Purity: 99.56% at 220 nm and 99.62% at 254 nm.

Example 5

N-(2-(5-(methoxymethyl)-1,3,4-oxadiazol-2-yl)ethyl)-5-phenylisoxazole-3-carboxamide Step-3: N-(2-(5-(methoxymethyl)-1,3,4-oxadiazol-2-yl)ethyl)-5-phenylisoxazole-3-carboxamide: A solution of 2-(5-methoxymethyl-[1,3,4]oxadiazol-2-yl)-ethylamine (100 mg, 0.00064 mol), 5-phenylisoxazole-3-carboxylic acid (144 mg, 0.00076 mol), TEA (0.13 ml, 0.00093 mol) and T₃P (0.303 mg, 0.00093 mol) in THF (5 mL) was stirred at room temperature for 12 h at room temperature. The reaction mixture was evaporated, diluted with aqueous NaHCO₃ solution (5 mL) and extracted with EtOAc (2×5 ml). Combined organic layers were washed with water, brine, dried over sodium sulfate and concentrated under vacuum to afford crude product. The crude compound was

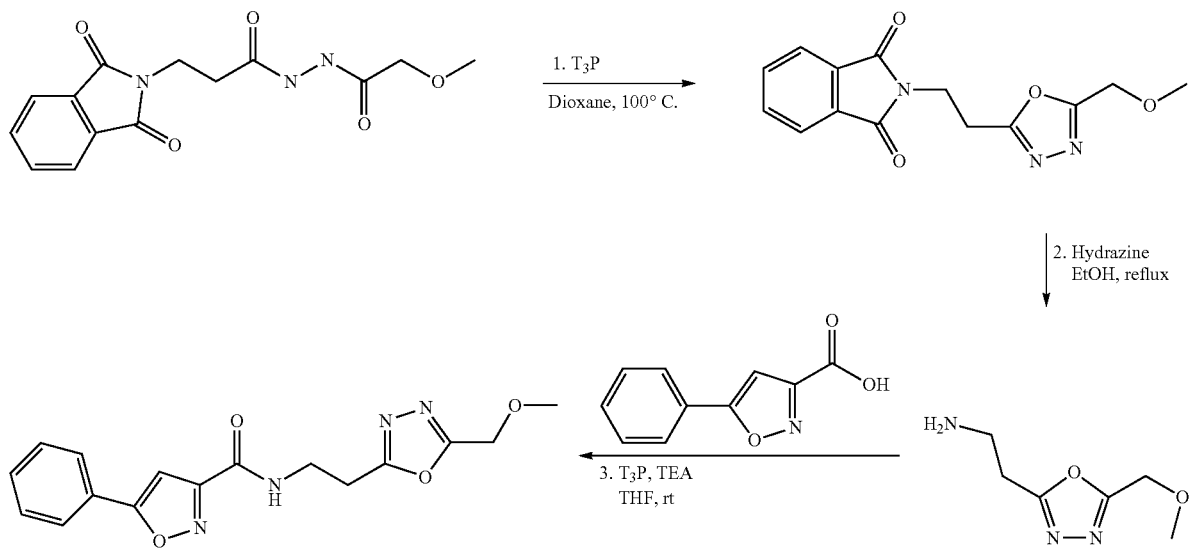

Step-1: 2-[2-(5-Methoxymethyl-[1,3,4]oxadiazol-2-yl)-ethyl]-isoindole-1,3-dione: A solution of 3-(1,3-dioxoisoindolin-2-yl)-N'-(2-methoxyacetyl)propane hydrazide (3 g, 0.0098 mol) and T₃P (15 g, 0.049 mol in 1,4-dioxane (100 mL) was heated at 100° C. for 18 h. The reaction mixture was evaporated, diluted with aqueous NaHCO₃ solution (50 mL) and extracted with EtOAc (2×10 mL). Combined organic layers were washed with water, brine, dried over sodium sulfate, filtered and concentrated under vacuum to afford crude product. The crude was triturated with n-pentane and dried to obtain compound (1.5 g, 52%) as off-white solid. ¹H NMR (400 MHz, CDCl₃): δ 7.83-7.81 (dd, J=8.5, 2.3 Hz, 2H), 7.72-7.70 (dd, J=8.5, 2.3 Hz, 2H), 4.61 (s, 2H), 4.14-4.10 (t, 2H), 3.43 (s, 3H), 3.27-3.24 (t, 2H); LC-MS: [M+H]$^+$=288.2.

Step-2: 2-(5-Methoxymethyl-[1,3,4]oxadiazol-2-yl)-ethylamine (5): Hydrazine hydrate (5 ml) was added to the solution of 2-[2-(5-Methoxymethyl-[1,3,4]oxadiazol-2-yl)-ethyl]-isoindole-1, 3-dione (0.700 g, 0.0024 mol) in ethanol (20 mL) at 0° C. and the resultant reaction mixture was stirred at room temperature for 24 h. Volatiles were evaporated, solid was stirred in 5% MeOH in DCM (50 ml), filtered and the filtrate was concentrated under vacuum to obtain crude compound (250 mg, 65%) as brownish liquid. ¹H NMR (400 MHz, CDCl₃): δ 4.61 (s, 2H), 3.44 (s, 3H), 3.19-3.16 (t, 2H), 3.00-2.97 (t, 2H); LC-MS: [M+H]$^+$ 158.1.

purified by preparative HPLC to obtain compound (100 mg) as off-white solid.

Yield: 48% Appearance: off-white solid

Analytical data: ¹H NMR (400 MHz, CDCl₃): δ 7.79-7.76 (m, 2H), 7.49-7.45 (m, 3H), 7.40 (br, 1H), 6.93 (s, 1H), 4.62 (s, 2H), 3.98-3.94 (q, 2H, J=6.4 Hz), 3.45 (s, 3H), 3.21-3.18 (t, 2H, J=4.7 Hz).

LC-MS: [M+H]$^+$=329.2; HPLC purity: 98.26% at 220 nm, 99.23% at 254 nm.

Example 6

N-(2-(5-(hydroxymethyl)-1,3,4-oxadiazol-2-yl)ethyl)-5-phenylisoxazole-3-carboxamide

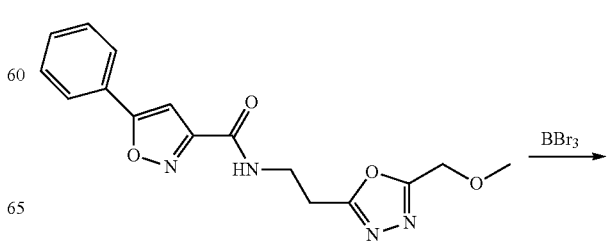

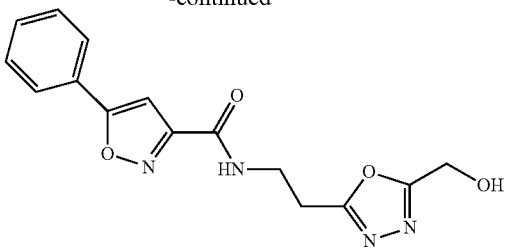

BBr₃ (1 ml, 0.00036 mol) was added slowly to a cold (−78° C.) solution of N-(2-(5-(methoxymethyl)-1,3,4-oxadiazol-2-yl)ethyl)-5-phenylisoxazole-3-carboxamide (70 mg, 0.00021 mol) in DCM (10 mL) and the reaction mixture was allowed to stirred at room temperature for 5 h. Reaction mixture was poured onto ice, stirred for 10 minutes and extracted with DCM (2×10 ml). Combined organic layers were washed with water, brine, dried over sodium sulfate and concentrated under vacuum to afford crude product. The crude was purified by column chromatography on neutral alumina using 5% MeOH in DCM to obtain product (22 mg).

Yield: 33%; Appearance: off-white solid

Analytical data: ¹H NMR (400 MHz, CDCl₃+3drops DMSO d6): δ 7.73-7.71 (m, 3H), 7.43-7.41 (m, 3H), 6.88 (s, 1H), 4.90-4.87 (t, 1H), 4.73-4.71 (d, 2H), 3.89-3.85 (m, 2H), 3.15-3.12 (t, 2H).

LC-MS: [M+H]⁺=315.2; HPLC purity: 98.12% at 270 nm, 98.03% at 254 nm.

Example 7

N-(2-(5-(azidomethyl)-1,3,4-thiadiazol-2-yl)ethyl)-5-phenylisoxazole-3-carboxamide

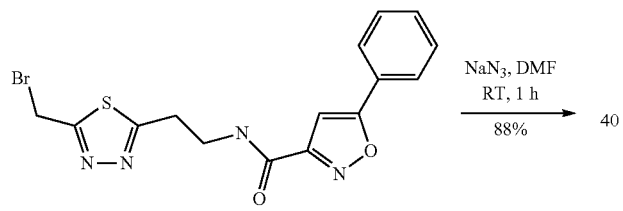

NaN₃ (0.0099 g, 0.15 mmol) was added to an ice-cooled solution of N-(2-(5-(bromomethyl)-1, 3,4-thiadiazol-2-yl)ethyl)-5-phenylisoxazole-3-carboxamide (0.05 g, 0.13 mmol, example 4) in DMF (3 mL) under nitrogen atmosphere and the reaction mixture was stirred at room temperature for 1 h. The reaction mixture was diluted with water (30 mL) and extracted with ethyl acetate (30 mL×3). Combined organic layer was washed with brine (30 mL×3), dried over anhydrous sodium sulfate and concentrated under reduced pressure to get crude compound. The crude compound thus obtained was washed with n-pentane (2 mL×2) and dried in vacuum to obtain N-(2-(5-(azidomethyl)-1,3,4-thiadiazol-2-yl)ethyl)-5-phenylisoxazole-3-carboxamide (0.040 g).

Yield: 88%

Appearance: white solid

Analytical data: ¹H NMR (400 MHz, CDCl₃): δ 7.79-7.77 (m, 2H), 7.48-7.46 (m, 3H), 7.39 (t, J=6 Hz, 1H), 6.94 (s, 1H), 4.78 (s, 2H), 3.98 (q, J=6.3 Hz, 2H), 3.44 (t, J=6.3 Hz, 2H).

LC-MS: [M+H]⁺=356.1

HPLC purity: 99.28% at 220 nm and 99.27% at 254 nm

Example 8

N-(2-(5-isopropyl-1,3,4-oxadiazol-2-yl)ethyl)-5-phenylisoxazole-3-carboxamide

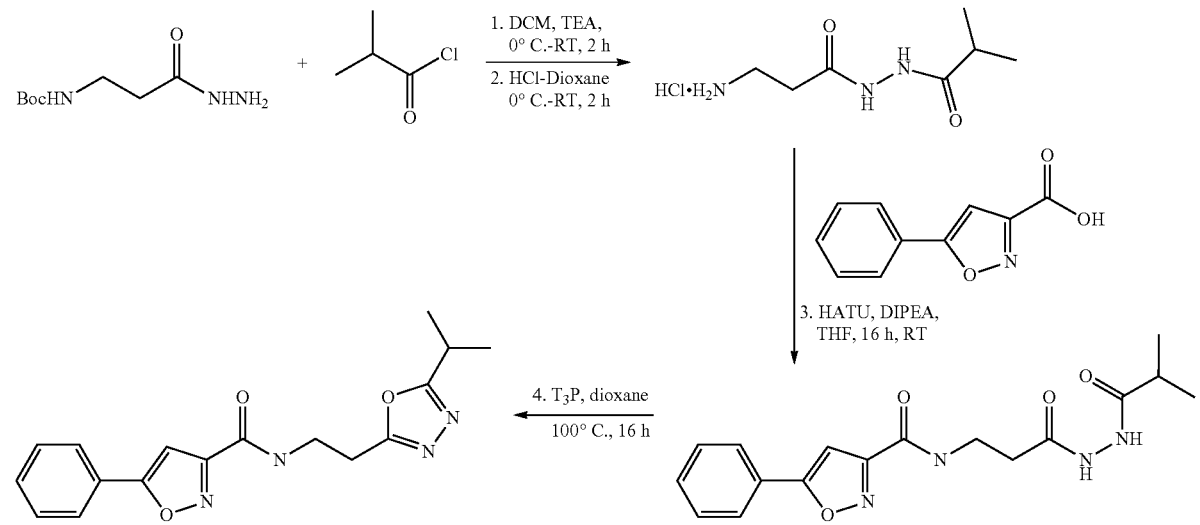

Step 1: tert-butyl (3-(2-isobutyrylhydrazinyl)-3-oxopropyl)carbamate: triethyl amine (0.99 g, 9.85 mmol) was added drop wise to a solution of tert-butyl (3-hydrazinyl-3-oxopropyl)carbamate (1.0 g, 4.92 mmol) in DCM (30 mL). The reaction mixture was cooled in an ice-bath and a solution of isobutyryl chloride (0.62 g, 5.91 mmol) in DCM (10 mL) was added drop-wise. The resulting reaction mixture was stirred at room temperature for 2 h. Then the reaction mixture was diluted with water (25 mL) and the organic layer was separated off. The aqueous was further extracted with DCM (60 mL×3). Combined organic layer was dried over $Na_2SO_4$ and solvent was removed under reduced pressure to get the crude compound which was purified by combiflash chromatography. Elution of 15% ethyl acetate in n-hexane afforded the product (0.6 g, crude) as off white solid. As per 1H-NMR, the compound is impure which was used as such in next step. LC-MS: $[M+H]^+=$ 271.9 m/z.

Step 2: 3-amino-N'-isobutyrylpropanehydrazide hydrochloride: 4N HCl in dioxane (8 mL) was added to an ice-cooled solution of tert-butyl (3-(2-isobutyrylhydrazinyl)-3-oxopropyl)carbamate (0.2 g, 0.73 mmol) in dioxane (2 mL) and the reaction mixture was stirred at room temperature for 2 h. The volatiles were removed under reduced pressure and the crude reaction mixture was azeotropically distilled with toluene. The crude compound was washed with diethyl ether (2 mL) to get hydrochloride salt (0.14 g, crude) which was used as such in next step without further purification. LC-MS: $[M+H]^+=174.1$ m/z.

Step 3: N-(3-(2-isobutyrylhydrazinyl)-3-oxopropyl)-5-phenylisoxazole-3-carboxamide: HATU (0.32 g, 0.84 mmol) and DIPEA (0.16 g, 1.26 mmol) were added sequentially to a solution of 5-phenyl-isoxazole-3-carboxylic acid (0.08 g, 0.42 mmol) in THF (15 mL). After 20 min, 3-amino-N'-isobutyrylpropanehydrazide hydrochloride (0.14 g, 0.84 mmol) was added and the reaction mixture was stirred for 16 h at room temperature. The volatiles were removed in vacuum and the crude reaction mixture was diluted with water (20 mL). The aqueous layer was extracted with ethyl acetate (50 mL×3) and combined organic layer was dried over $Na_2SO_4$. Solvent removed under reduced pressure to get the crude compound which was further purified by combiflash chromatography using 70% ethyl acetate in n-hexane as eluent to afford the product (0.14 g, crude) as off white solid. As per 1H-NMR, the compound is impure which was used as such in next step. LC-MS: $(M+H)^+=345.0$.

Step 4: N-(2-(5-isopropyl-1,3,4-oxadiazol-2-yl)ethyl)-5-phenylisoxazole-3-carboxamide: $T_3P$ (0.64 g, 2.03 mmol) was added to a solution of N-(3-(2-isobutyrylhydrazinyl)-3-oxopropyl)-5-phenylisoxazole-3-carboxamide (0.14 g, 0.40 mmol) in 1,4 dioxane (10 mL) and the reaction mixture was heated to 100° C. for 16 h. The volatiles were removed under reduced pressure the reaction mixture diluted with water (20 mL) and the aq. layer was extracted with ethyl acetate (50 mL×3). Combined organic layer was dried over $Na_2SO_4$ and concentrated under reduced pressure to get the crude compound. The crude compound was purified by combiflash chromatography using 65% ethyl acetate in n-hexane as eluent to afford compound the product (0.031 g)

Yield: 10% over 4 steps

Appearance: off white solid

Analytical data: $^1$H NMR (400 MHz, $CDCl_3$) δ 7.79-7.76 (m, 2H), 7.50-7.46 (m, 3H), 7.41 (t, 1H), 6.93 (s, 1H), 3.94 (q, J=6.3 Hz, 2H), 3.19-3.12 (m, 3H), 1.37 (d, J=7 Hz, 6H).

LC-MS: $(M+H)^+=326.9$ m/z

HPLC purity: 98.18% at 220 nm, 98.63% at 254 nm and 98.8% at 270 nm.

Example 9

N-(2-(5-(2-hydroxypropan-2-yl)-1,3,4-thiadiazol-2-yl)ethyl)-5-phenylisoxazole-3-carboxamide

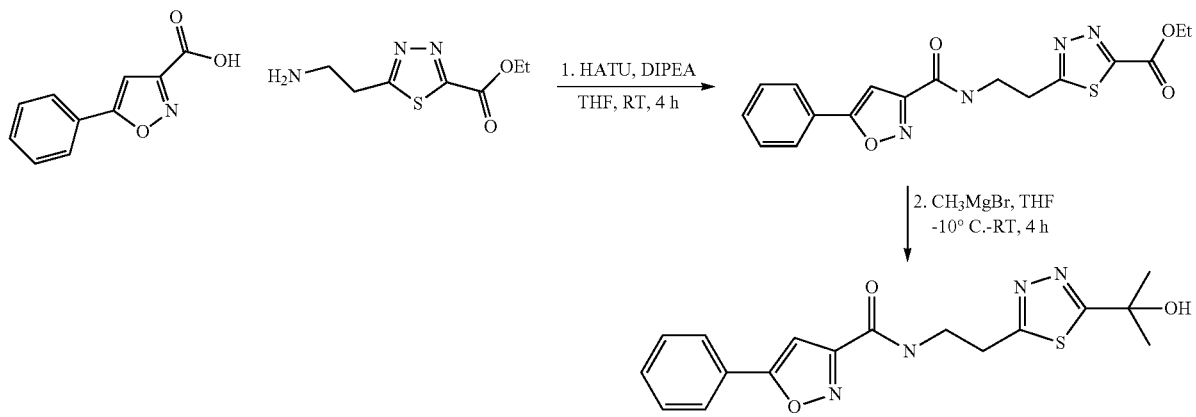

Step 1: ethyl 5-(2-(5-phenylisoxazole-3-carboxamido)ethyl)-1,3,4-thiadiazole-2-carboxylate: HATU (0.45 g, 0.001 mol) was added to a solution of 5-phenylisoxazole-3-carboxylic acid (0.15 g, 0.7 mmol) and ethyl 5-(2-aminoethyl)-1,3,4-thiadiazole-2-carboxylate (0.2 g, 1 mmol) in THF (4 mL) followed by DIPEA (0.3 g, 2 mmol) and the resulting reaction mixture was stirred at room temperature for 4 h. Progress of the reaction was monitored by TLC. The reaction mixture was poured onto ice cooled water (10 mL) and the precipitate thus formed was filtered. Residue was washed with water and hexane (2×10 mL) and dried under reduced pressure to afford the product (0.14 g, 48.2%) as off white solid. $^1$H NMR (400 MHz, $CDCl_3$): δ 7.79-7.76 (m, 2H), 7.50-7.45 (m, 3H), 7.38 (t, J=5.6 Hz, 1H), 6.93 (s, 1H), 4.50 (q, J=7.1 Hz, 2H), 4.00 (q, J=6.3 Hz, 2H), 3.51 (t, J=6.4 Hz, 2H), 1.44 (t, J=7.1 Hz, 3H); LC-MS: $[M+H]^+=373.7$.

Step 2: N-(2-(5-(2-hydroxypropan-2-yl)-1,3,4-thiadiazol-2-yl)ethyl)-5-phenylisoxazole-3-carboxamide: methyl magnesium bromide (1.6 mL, 0.0008 mol, 1M in THF) was added to a solution of ethyl 5-(2-(5-phenylisoxazole-3-carboxamido)ethyl)-1,3,4-thiadiazole-2-carboxylate (0.1 g, 0.0002 mol) in dry THF (5 mL) under nitrogen at −10° C. The reaction mixture was stirred at room temperature for 4 h, quenched with aq ammonium chloride solution (10 mL) and the aq. phase was extracted with ethyl acetate (2×20 mL). Combined organic layer was washed with brine (20 mL), dried over anhydrous $Na_2SO_4$ and concentrated under reduced pressure to obtain crude compound which was further purified by combiflash using 30% ethyl acetate in hexane as eluent to afford N-(2-(5-(2-hydroxypropan-2-yl)-1,3,4-thiadiazol-2-yl)ethyl)-5-phenylisoxazole-3-carboxamide (0.09 g).

Yield: 94%
Appearance: off white solid
Analytical data: $^1$H NMR (400 MHz, DMSO-$d_6$): δ 9.04 (t, J=5.6 Hz, 1H), 7.95-7.92 (m, 2H), 7.58-7.54 (m, 3H), 7.37 (s, 1H), 6.17 (s, 1H), 3.67-3.62 (m, 2H), 3.34-3.31 (m obscured by solvent signal, 2H), 1.53 (s, 6H).
LC-MS: [M+H]$^+$=359.0 m/z
HPLC Purity: 99.8% at 254 nm & 99.77% at 220 nm.

Example 10

N-(2-(5-(2-hydroxypropan-2-yl)-1,3,4-oxadiazol-2-yl)ethyl)-5-phenylisoxazole-3-carboxamide The reaction mixture was stirred for 15 min. To the resulting reaction mixture was added ethyl 2-(2-(3-((tert-butoxycarbonyl)amino)propanoyl)hydrazinyl)-2-oxoacetate (0.7 g, 2 mmol) and the reaction mixture was stirred at room temperature for 3 h. The reaction mixture was concentrated and the residue was purified by silica gel (100-200 mesh) column chromatography using 2% methanol in dichloromethane as eluent to afford product (0.5 g) as off white solid. As per,$^1$H NMR compound is impure and used as such in next step without further purification.

Step 3: ethyl 5-(2-aminoethyl)-1,3,4-oxadiazole-2-carboxylate: HCl (10 mL) was added to a solution of ethyl 5-(2-((tert-butoxycarbonyl)amino)ethyl)-1,3,4-oxadiazole-2-carboxylate (0.5 g, 0.001 mol) in dioxane. The resulting reaction mixture was stirred at room temperature for 3 h, concentrated under reduced pressure to obtain crude product (0.5 g, crude). The crude compound was as such in next step without further purification.

Step 4: ethyl 5-(2-(5-phenylisoxazole-3-carboxamido)ethyl)-1,3,4-oxadiazole-2-carboxylate: HATU (0.9 g, 2 mmol) was added to a solution of 5-phenylisoxozale-3-carboxylic acid (0.3 g, 1 mmol) and ethyl 5-(2-aminoethyl)-1,3,4-oxadiazole-2-carboxylate (0.42 g, 1 mmol) in THF (10 mL) followed by DIPEA (0.6 g, 4 mmol) and the resulting

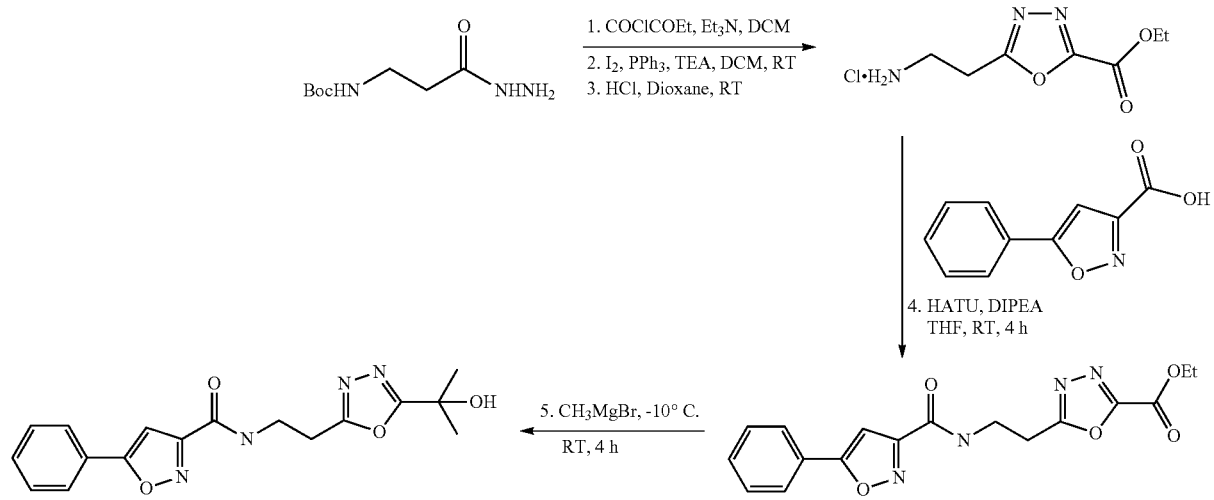

Step 1: ethyl 2-(2-(3-((tert-butoxycarbonyl)amino)propanoyl)hydrazinyl)-2-oxoacetate: triethyl amine (0.9 g, 9 mmol) was added to a solution of tert-butyl (3-hydrazinyl-3-oxopropyl)carbamate (1.0 g, 4 mmol) in DCM (20 mL) followed by ethyl oxalyl chloride (0.8 g, 5 mmol) and the reaction mixture was stirred at room temperature for 4 h. The reaction mixture was poured into ice cooled water (30 mL) and organic layer was separated off. The aq. layer was further extracted with DCM (2×30 mL) and washed with brine (50 mL). Combined organic layer was dried over anhydrous $Na_2SO_4$ and concentrated under reduced pressure to afford the product (7 g, crude) as yellowish viscous oil which was used as such in next step without further purification.

Step 2: ethyl 5-(2-((tert-butoxycarbonyl)amino)ethyl)-1,3,4-oxadiazole-2-carboxylate: to a stirred solution of $PPh_3$ (1.2 g, 4 mmol) in DCM (20 mL) was added $I_2$ (1.1 g, 4 mmol) at room temperature. After $I_2$ was dissolved, triethyl amine (1.16 g, 11 mmol) was added to the reaction mixture.

reaction mixture was stirred at room temperature for 4 h. The reaction mixture was poured onto ice water (10 mL) and the aq. phase was extracted with ethyl acetate (2×30 mL). Combined organic layer was washed with brine (30 mL), dried over anhydrous $Na_2SO_4$ and concentrated under reduced pressure to get the crude compound which was further purified by using silica gel (100-200 mesh) column chromatography using 40% ethyl acetate in hexane as eluent to afford the product (0.2 g, 11% over four steps) as off white solid. $^1$H NMR (400 MHz, CDCl$_3$): δ 7.78-7.76 (m, 2H), 7.50-7.46 (m, 3H), 7.39 (t, J=5.9 Hz, 1H), 6.91 (s, 1H), 4.50 (q, J=7.1Hz, 2H), 4.00 (q, J=6.4 Hz, 2H), 3.29 (t, J=6.3 Hz, 2H), 1.40 (t, J=6 Hz, 3H); LC-MS: [M+H]$^+$=356.8 m/z.

Step 5: N-(2-(5-(2-hydroxypropan-2-yl)-1,3,4-oxadiazol-2-yl)ethyl)-5-phenylisoxazole-3-carboxamide: methyl magnesium bromide (1M in THF; 1.6 mL, 1.6 mmol) was added to a solution of ethyl 5-(2-(5-phenylisoxazole-3-carboxamido)ethyl)-1,3,4-oxadiazole-2-carboxylate (0.2 g, 0.5 mmol) in dry THF (10 mL) under nitrogen at −10° C. The reaction mixture was stirred at room temperature for 4 h, quenched with aq ammonium chloride solution (10 mL) and the aq. phase was extracted with ethyl acetate (2×30 mL). Combined organic layer was washed with brine (30 mL), dried over anhydrous $Na_2SO_4$ and concentrated under reduced pressure to obtain crude compound which was further purified by (100-200 mesh) silica gel column chromatography using 60% ethyl acetate in hexane as eluent to afford the product (0.04 g).

Yield: 21%
Appearance: off white solid
Analytical data: $^1$H NMR (400 MHz, DMSO-$d_6$): δ 9.00 (t, J=5.8 Hz, 1H), 7.94-7.92 (m, 3H), 7.57-7.54 (m, 3H), 7.36 (s, 1H), 5.79 (s, 1H), 3.68-3.62 (m, 2H), 3.12 (t, J=6.8 Hz, 2H), 1.50 (s, 6H)
LC-MS: $[M+H]^+$=343.0 m/z.
HPLC purity: 93.8% at 254 nm and 92.9% at 220 nm.

Example 11

4-fluoro-N-(2-(5-(hydroxymethyl)-1,3,4-thiadiazol-2-yl)ethyl)-5-phenylisoxazole-3-carboxamide Step 3: ethyl 4-fluoro-5-phenyl-1,2-oxazole-3-carboxylate: selectfluor (1.71 g, 4.83 mmol, 1.05 equiv) was added to a solution of ethyl 5-phenyl-1,2-oxazole-3-carboxylate (1 g, 4.60 mmol, 1.00 equiv) in sulfone (5 mL). The resulting solution was stirred for 16 hours at 105° C. and then diluted with 100 mL of ethyl acetate. The resulting mixture was washed with brine (2×100 mL), dried over anhydrous sodium sulfate and concentrated under vacuum. The residue was applied onto a silica gel column with ethyl acetate/petroleum ether (1:20) to give 0.15 g (14%) of ethyl 4-fluoro-5-phenyl-1,2-oxazole-3-carboxylate as a yellow solid. LC-MS: $[M+H]^+$=236.

Step 4: of 4-fluoro-5-phenyl-1,2-oxazole-3-carboxylic acid: LiOH (240 mg, 10.02 mmol, 4.00 equiv) was added to a solution of ethyl 4-fluoro-5-phenyl-1,2-oxazole-3-carboxylate (600 mg, 2.55 mmol, 1.00 equiv) in tetrahydrofuran/$H_2O$ (10/5 mL). The resulting solution was stirred for 1 hour at 25° C., diluted with 100 mL of water. The pH value of the solution was adjusted to 3 with concentrated HCl aqueous. The resulting solution was extracted with ethyl

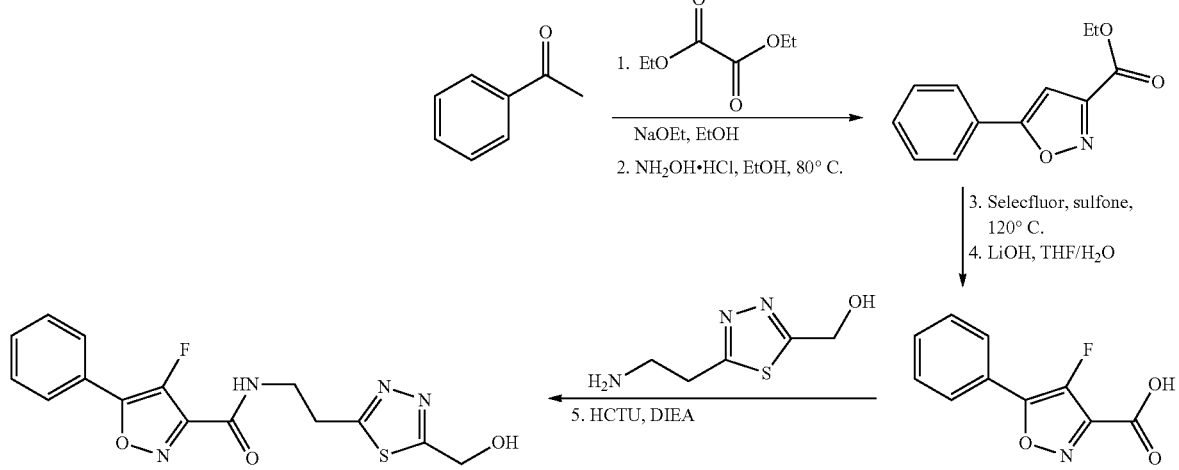

Step 1: ethyl 2,4-dioxo-4-phenylbutanoate: NaOEt (22 g, 323.53 mmol, 2.00 equiv) was added in portions to a 0° C. solution of 1-phenylethan-1-one (20 g, 166.46 mmol, 1.00 equiv) and diethyl oxalate (48.8 g, 333.92 mmol, 2.00 equiv) in ethanol (200 mL). The resulting solution was stirred for 2 hours at 25° C., quenched by the addition of 300 mL of hydrogen chloride aqueous (1N). The resulting solution was extracted with ethyl acetate (2×500 mL) and the organic layers combined. The resulting mixture was washed with brine (2×400 mL), dried over anhydrous sodium sulfate and concentrated under vacuum. This resulted in 21 g (57%) of ethyl 2,4-dioxo-4-phenylbutanoate as yellow oil. LC-MS: $[M+H]^+$=221.

Step 2: ethyl 5-phenyl-1,2-oxazole-3-carboxylate: $NH_4OH \cdot HCl$ (13 g, 185.71 mmol, 2.50 equiv) was added to a solution of ethyl 2,4-dioxo-4-phenylbutanoate (16 g, 72.65 mmol, 1.00 equiv) in ethanol (150 mL). The resulting solution was stirred for 2 hours at 80° C., and then diluted with 800 mL of ethyl acetate. The resulting mixture was washed with brine (2×500 mL), dried over anhydrous sodium sulfate and concentrated under vacuum. This resulted in 14 g (89%) of ethyl 5-phenyl-1,2-oxazole-3-carboxylate as a yellow solid. LC-MS: $[M+H]^+$=218.

acetate (3×50 mL) and the organic layers combined. The resulting mixture was washed with brine (2×100 mL), dried over anhydrous sodium sulfate and concentrated under vacuum to give 480 mg (91%) of 4-fluoro-5-phenyl-1,2-oxazole-3-carboxylic acid as a light yellow solid.

Step 5: [5-(2-aminoethyl)-1,3,4-thiadiazol-2-yl]methanol (400 mg, 2.51 mmol, 1.00 equiv), DIEA (900 mg, 6.96 mmol, 3.00 equiv) and HCTU (1.4 g, 3.38 mmol, 1.50 equiv) were added to a solution of 4-fluoro-5-phenyl-1,2-oxazole-3-carboxylic acid (480 mg, 2.32 mmol, 1.00 equiv) in dichloromethane (50 mL). The resulting solution was stirred for 2 hours at 25° C., then diluted with 250 mL of ethyl acetate. The resulting mixture was washed with water (2×100 mL) and brine (2×100 mL). The mixture was dried over anhydrous sodium sulfate and concentrated under vacuum. The crude product was purified by Prep-HPLC with the following conditions: Column, Xbridge Prep shield RP18, 5 nm, 19×150 mm; mobile phase, $CH_3CN/H_2O$ (0.05% $NH_4HCO_3$)=30% increasing to $CH_3CN/H_2O$(0.05%

NH₄HCO₃)=60% within 8 min; Detector, UV 254 nm. This resulted in 121 mg of 4-fluoro-N-[2-[5-(hydroxymethyl)-1,3,4-thiadiazol-2-yl]ethyl]-5-phenyl-1,2-oxazole-3-carboxamide.

Yield: 15%
Appearance: white solid
Analytical data: ¹H NMR (400MHz, DMSO-d₆, ppm): δ 9.20-9.17 (m, 1H), 7.84-7.82 (m, 2H), 7.65-7.57 (m, 2H), 6.16-6.13 (m, 1H), 4.82-4.80 (m, 2H), 3.70-3.66 (m, 2H), 3.38-3.33 (m, 2H).

J=8.8 Hz, 2H), 6.16-6.13 (m, 1H), 4.82-4.80 (d, J=6.0 Hz 1H), 3.68-3.64 (m, 2H), 3.38-3.34 (m, 2H).

LC-MS: [M+H]⁺=367
HPLC purity: 100% at 254 nm.

Example 13

(R)-N-(2-(5-(1-hydroxyethyl)-1,3,4-thiadiazol-2-yl)ethyl)-5-phenylisoxazole-3-carboxamide

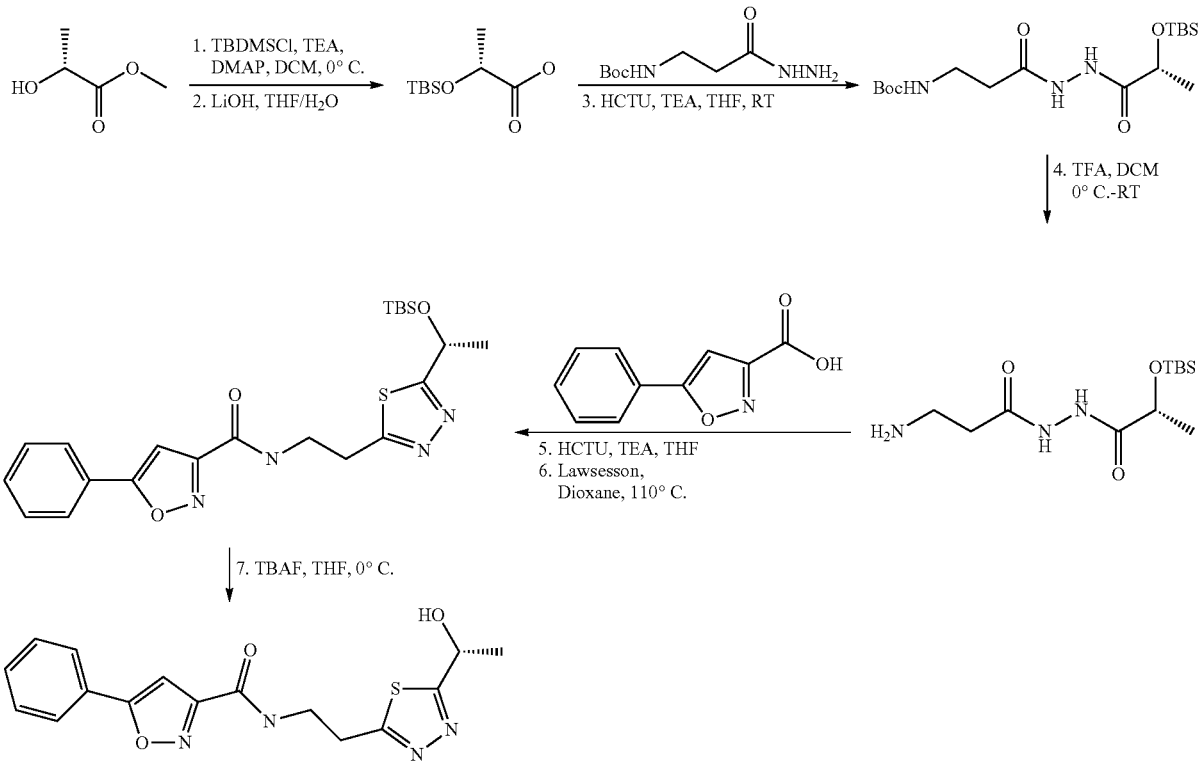

LC-MS: [M+H]⁺=349
HPLC purity: 100% at 254 nm.

Example 12

4-fluoro-5-(4-fluorophenyl)-N-(2-(5-(hydroxymethyl)-1,3,4-thiadiazol-2-yl)ethyl)isoxazole-3-carboxamide This compound was prepared by the procedure described in example 11 using 1-(4-fluorophenyl)ethan-1-one.

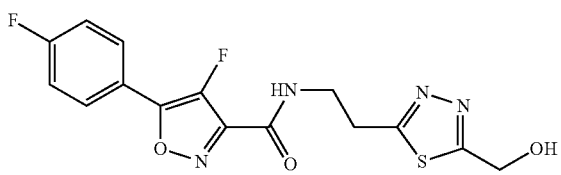 [SMILES: O=C(NCCc1nnc(CO)s1)c1noc(-c2ccc(F)cc2)c1F]

Appearance: white solid
Analytical data: ¹H NMR (400MHz, DMSO-d₆, ppm): δ 9.20-9.17 (t, J=5.6 Hz, 1H), 7.91-7.87 (m, 2H), 7.51-7.46 (t, Step 1: methyl (R)-2-((tert-butyldimethylsilyl)oxy)propanoate: TEA (5.82 mL, 43 mmol) and DMAP (0.35 g, 2.88 mmol) were added sequentially to an ice-cooled solution of (+) D-Methyl lactate (3 g, 28.8 mmol) in DCM (60 mL). To the resulting reaction mixture was added a solution of tert-Butyldimethylsilyl chloride (4.75 g, 31.6 mmol) in DCM (15 mL) and the reaction mixture was stirred for 16 h at room temperature, then diluted with water (70 mL) and organic layer was separated off. The organic layer was washed with 1M citric acid solution (50 mL) followed by saturated sodium bicarbonate solution (50 mL) and dried over anhydrous Na₂SO₄ Solvent was removed under reduced pressure to afford the product (4.78 g, 78%) as colorless oil which was used as such without further purification. ¹H NMR (400 MHz, CDCl₃): δ 4.31 (q, J=6.7 Hz, 1H), 0.90 (s, 1H), 0.89 (s, 9H), 0.09 (s, 3H), 0.07 (s, 3H), LC-MS: [M+H]⁺ 218.9.

Step 2: (R)-2-((tert-butyldimethylsilyl)oxy)propanoic acid: a solution of lithium hydroxide (3.62 g, 87.7 mmol) in water (20 mL) was added to a solution of methyl (R)-2-((tert-butyldimethylsilyl)oxy)propanoate (4.7 g, 21.9 mmol) in THF (40 mL)and the reaction mixture was stirred for 16 h at room temperature. Volatiles were removed under reduced pressure, the crude compound was suspended in water (100 mL) and the aq. layer was washed with diethyl ether (2×100 mL). The aq. layer was acidified with diluted HCl and extracted with ethyl acetate (2×150 mL). Combined organic layer was dried over anhydrous sodium sulfate and concentrated under reduced pressure to afford the product (2.3 g, crude) which was used as such in next step without further purification.

Step 3: tert-butyl (R)-(3-(2-(2-((tert-butyldimethylsilyl)oxy)propanoyl)hydrazinyl)-3-oxopropyl)carbamate: TEA (2.63 mL, 19.6 mmol) and HCTU (4.84 g, 11.7 mmol) were sequentially added to a solution of (R)-2-((tert-butyldimethylsilyl)oxy)propanoic acid (2.3 g, crude) and tert-butyl (3-hydrazinyl-3-oxopropyl)carbamate (2 g, 9.8 mmol) in THF (50 mL)and the reaction mixture was stirred for 16 h at room temperature. Then the reaction mixture was diluted with water (100 mL) and extracted with ethyl acetate (3×50 mL). Combined organic layer was washed with brine (50 mL), dried over anhydrous Na$_2$SO$_4$ and concentrated under reduced pressure to afford crude compound which was further purified by silica gel (230-400 mesh) column chromatography using 30% EtOAc in hexane as eluent to obtain the product (2.25 g, 26% over two steps) as white solid. $^1$H NMR (400 MHz, CDCl$_3$): δ 8.92 (br, 1H), 8.26 (br, 1H), 5.15 (br, 1H), 4.33 (q, J=6.7 Hz, 1H), 3.46-3.42 (m, 2H), 2.49-2.46 (m, 2H), 1.42-1.41 (s overlapped with some impurity, 9H), 0.93 (s, 9H), 0.12 (s, 3H), 0.11 (s, 3H).

Step 4: (R)-3-amino-N'-(2-((tert-butyldimethylsilyl)oxy)propanoyl)propanehydrazide: TFA (3.24 mL, 28.0 mmol) was added to an ice-cooled solution of tert-butyl (R)-(3-(2-(2-((tert-butyldimethylsilyl) oxy)propanoyl)hydrazinyl)-3-oxopropyl)carbamate (2.25 g, 5.7 mmol) in DCM (30 mL and the reaction mixture was stirred for 4 h at room temperature, the volatiles were removed under reduced pressure to obtain the product (2.7 g, crude) which was used as such in next step without further purification.

Step 5: tert-butyl (R)-(3-(2-(2-((tert-butyldimethylsilyl)oxy)propanoyl)hydrazinyl)-3-oxopropyl)carbamate: TEA (3.8 mL, 28 mmol) and HCTU (2.81 g, 6.8 mmol) were added sequentially to a solution of R)-3-amino-N'-(2-((tert-butyldimethylsilyl)oxy)propanoyl)propanehydrazide (1.67 g, crude) and 5-phenylisoxazole-3-carboxylic acid (1.09 g, 5.7 mmol) in THF (50 mL) and the reaction mixture was stirred for 16 h at room temperature. Then the reaction mixture was diluted with water (100 mL) and extracted with ethyl acetate (3×50 mL). Combined organic layer was washed with brine (50 mL), dried over anhydrous Na$_2$SO$_4$ and concentrated under reduced pressure to afford crude compound which was further purified by silica gel (230-400 mesh) column chromatography using 50% EtOAc in hexane as eluent to obtain product (1.53 g, 57% over two steps) as off-white solid. $^1$H NMR (400 MHz, DMSO): δ 9.99 (s, 1H), 9.44 (s, 1H), 8.81 (t, J=5.8 Hz, 1H), 7.94-7.92 (m, 2H), 7.57-7.53 (m, 3H), 7.35 (s, 1H), 4.26 (q, J=6.5 Hz, 1H), 3.51-3.46 (m, 2H), 2.49-2.44 (m, 2H), 1.27 (d, J=6.6 Hz, 3H), 0.87 (s, 9H), 0.08 (s, 6H); LC-MS: [M+H]$^+$ 461.0.

Step 6: (R)-N-(2-(5-(1-((tert-butyldimethylsilyl)oxy)ethyl)-1,3,4-thiadiazol-2-yl)ethyl)-5-phenylisoxazole-3-carboxamide: Lawesson's reagent (0.34 g, 0.86 mmol) was added to a solution of tert-butyl (R)-(3-(2-(2-((tert-butyldimethylsilyl)oxy)propanoyl) hydrazinyl)-3-oxopropyl)carbamate (0.4 g, 0.86 mmol) in 1,4-dioxane (8 mL)and the reaction mixture was heated to 110° C. for 2 h. Then the reaction mixture was diluted with water (25 mL) and extracted with ethyl acetate (2×20 mL). The organic layer was washed with brine (20 mL), dried over anhydrous Na$_2$SO$_4$ and concentrated under reduced pressure to afford crude compound which was purified by silica gel (230-400 mesh) column chromatography using 30% EtOAc in hexane as eluent to obtain compound 7 (0.070 g, 17%) as off-white solid. $^1$H NMR (400 MHz, CDCl$_3$): δ 7.79-7.76 (m, 2H), 7.49-7.45 (m, 4H), 6.94 (s, 1H), 5.22 (q, J=6.4 Hz, 1H), 3.98-3.93 (m, 2H), 3.39-3.36 (m, 2H), 0.88 (s, 9H), 0.11 (s, 3H), 0.05 (s, 3H); LC-MS: [M+H]$^+$ 459.3.

Step 7: (R)-N-(2-(5-(1-hydroxyethyl)-1,3,4-thiadiazol-2-yl)ethyl)-5-phenylisoxazole-3-carboxamide: TBAF (1 M solution in THF) (0.3 mL, 0.30 mmol) was added to an ice-cooled solution of (R)-N-(2-(5-(1-((tert-butyldimethylsilyl)oxy)ethyl)-1,3,4-thiadiazol-2-yl)ethyl)-5-phenylisoxazole-3-carboxamide (0.07 g, 0.15 mmol) in THF (2 mL) and the reaction mixture was stirred for 2 h at room temperature. After completion of reaction (monitored by TLC), volatiles were removed under reduced pressure. The crude reaction mixture was diluted with water (30 mL) and the aq. phase was extracted with ethyl acetate (2×20 mL). Combined organic layer was washed with brine (20 mL), dried over anhydrous Na$_2$SO$_4$ and concentrated under reduced pressure to afford crude product (0.080 g) which was triturated with diethyl ether (20 mL) and pentane (30 mL) to give the product (0.030 g)

Yield: 57%

Appearance: off-white solid.

Analytical data: $^1$H NMR (400 MHz, CDCl$_3$): δ 7.79-7.77 (m, 2H), 7.48-7.45 (m, 4H), 6.94 (s, 1H), 5.28 (q, J=6.5 Hz, 1H), 3.99-3.94 (m, 2H), 3.41 (t, J=6.3 Hz, 2H), 3.33 (br, 1H), 1.68 (d, J=6.5 Hz, 3H), 0.98 (m, 1H).

LC-MS: [M+H]$^+$ 345.0

HPLC purity: 95.47% at 270 nm and 94.12% at 220 nm.

Example 14

(R)-N-(2-(5-(1-hydroxyethyl)-1,3,4-oxadiazol-2-yl)ethyl)-5-phenylisoxazole-3-carboxamide This compound was prepared by the procedures described in example 10.

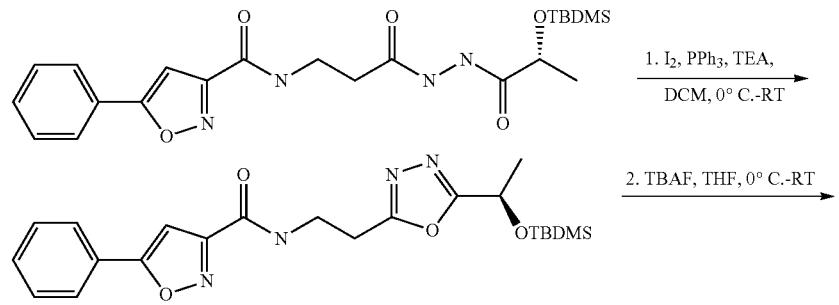

-continued

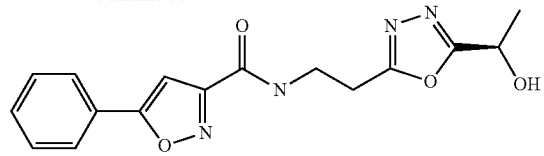

Step 1: (R)-N-(2-(5-(1-((tert-butyldimethylsilyl)oxy) ethyl)-1,3,4-oxadiazol-2-yl)ethyl)-5-phenylisoxazole-3-carboxamide: iodine (0.275 g, 1.0 mmol) was added to a solution of triphenyl phosphine (0.262 g, 1.0 mmol) in DCM (10 mL) and the reaction mixture was stirred for 10 min. Then the reaction mixture was cooled to 0° C. To the resulting reaction mixture were added TEA (0.34 g, 2.5 mmol) and (R)-N-(3-(2-(2-((tert-butyldimethylsilyl)oxy) propanoyl)hydrazinyl)-3-oxopropyl)-5-phenylisoxazole-3-carboxamide (0.250 g, 0.5 mmol) sequentially and the reaction mixture was stirred for 2 h at room temperature. Volatiles were removed under reduced pressure and the crude reaction mixture was diluted with ethyl acetate. The precipitate thus formed was filtered, filtrate concentrated and purified by silica gel (200-400 mesh) column chromatography using 50% ethyl acetate in n-hexane as eluent to afford the product (0.140 g, crude) as off-white solid. As per 1H-NMR, the compound is impure which was used as such in next step. LC-MS: [M+H]+ 443.3.

Step 2: (R)-N-(2-(5-(1-hydroxyethyl)-1,3,4-oxadiazol-2-yl)ethyl)-5-phenylisoxazole-3-carboxamide: TBAF (1 M solution in THF) (0.6 mL, 0.6 mmol) was added to a solution of (R)-N-(2-(5-(1-(((tert-butyldimethylsilyl)oxy)ethyl)-1,3,4-oxadiazol-2-yl)ethyl)-5-phenylisoxazole-3-carboxamide (0.140 g, crude) in THF (10 mL) and the reaction mixture was stirred for 2 h at room temperature. The volatiles were removed under reduced pressure, and the reaction mixture was diluted with water (30 mL) and the aq. phase was extracted with ethyl acetate (2×20 mL). Combined organic layer was washed with brine (20 mL), dried over anhydrous Na$_2$SO$_4$ and concentrated under reduced pressure to afford crude product (0.080 g) which was triturated with diethyl ether (20 mL) and pentane (30 mL) to obtain (0.100 g)

Yield: 54% over two steps

Appearance: off-white solid.

Analytical data: $^1$H NMR (400 MHz, CDCl$_3$): δ 7.79-7.76 (m, 2H), 7.48-7.46 (m, 3H), 7.44-7.41 (m, 1H), 6.93 (s, 1H), 5.09-5.06 (m, 1H), 3.95 (q, J=6.3 Hz, 2H), 3.38-3.34 (m, 1H), 3.20-3.17 (m, 2H), 2.61 (d, 1H), 1.65 (d, J=6.6 Hz, 3H).

LC-MS: [M+H]+ 329.1

HPLC purity: 99.85% at 270 nm and 98.76% at 220 nm.

Example 15

5-phenyl-N-(2-(5-((trifluoromethoxy)methyl)-1,3,4-oxadiazol-2-yl)ethyl)isoxazole-3-carboxamide

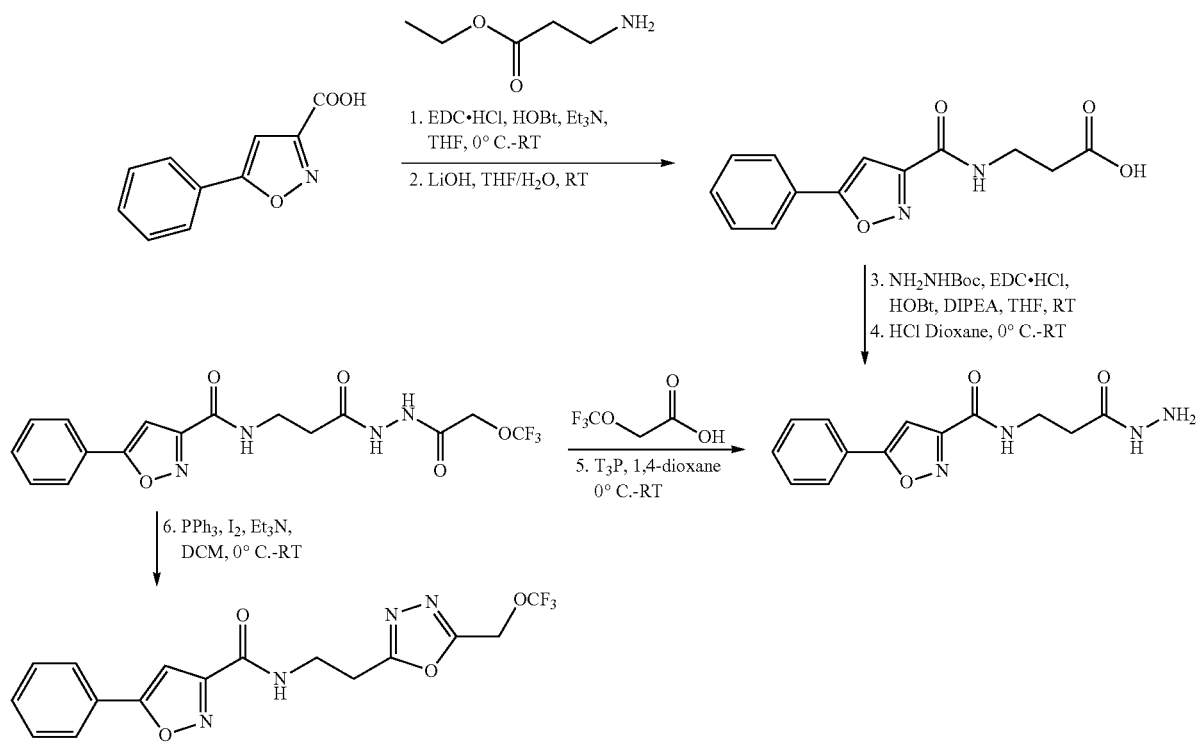

Step 1: ethyl 3-(5-phenylisoxazole-3-carboxamido)propanoate: HOBt (7.50 g, 0.055 mol), ethyl 3-aminopropanoate (5.0 g, 42.0 mmol), triethylamine (17.30 g, 170 mmol) and EDC.HCl (12.20 g, 65.0 mmol) were added sequentially to an ice cooled stirred solution of 5-phenylisoxazole-3-carboxylic acid (8.07 g, 42.0 mmol) in THF (170 mL) and the reaction mixture was stirred at room temperature for 16 h. Volatiles were concentrated under reduced pressure and ice-water (200 mL) was added to the crude reaction mixture. The precipitate thus obtained was filtered and dried to afford crude compound which was further purified by flash column chromatography using 25% EtOAc in hexane as eluent to obtain the product (6.5 g, 53%) as off-white solid. $^1$H NMR (400 MHz, CDCl$_3$): δ 7.79-7.76 (m, 2H), 7.50-7.45 (m, 3H), 7.35 (br s, 1H), 6.94 (s, 1H), 4.17 (q, J=7.1 Hz, 2H), 3.75-3.71 (m, 2H), 2.66-2.63 (t, J=6.1 Hz, 2H), 1.27 (t, J=7.1 Hz, 3H); LC-MS: [M+H]$^+$ 289.1.

Step 2: 3-(5-phenylisoxazole-3-carboxamido)propanoic acid: a solution of LiOH.H$_2$O (0.61 g, 14.0 mmol) in water (17 mL) was added to solution of ethyl 3-(5-phenylisoxazole-3-carboxamido)propanoate (3.5 g, 12.0 mmol) in THF (50 mL) and the reaction mixture was stirred at room temperature for 16 h. Volatiles were concentrated under reduced pressure and the residue was suspended in ice-water (100 mL). Then the reaction mixture was acidified with cold diluted HCl (5 mL) and the solid was filtered and dried to obtain the product (2.30 g, 72.80%) as off-white solid. $^1$H NMR (400 MHz, DMSO-d$_6$): δ 12.30 (br, 1H), 8.81 (t, J=5.5 Hz, 1H), 7.94-7.92 (m, 2H), 7.57-7.53 (m, 3H), 7.36 (s, 1H), 3.47 (q, J=7 Hz, 2H), 2.55-2.51 (signal obscured by solvent signal, 2H); LC-MS: [M+H]$^+$ 261.2.

Step 3: tert-butyl 2-(3-(5-phenylisoxazole-3-carboxamido)propanoyl)hydrazine-1-carboxylate: HOBt (1.49 g, 10.99 mmol), EDC.HCl (2.42 g, 12.70 mmol), DIPEA (4.36 g, 33.84 mmol) and Boc-hydrazine (1.51 g, 10.15 mmol) were added to a solution of 3-(5-phenylisoxazole-3-carboxamido)propanoic acid (2.20 g, 8.46 mmol) in THF (35 mL) and the reaction mixture was stirred for 16 h. Volatiles were removed under reduced pressure to obtain crude reaction mixture which was partitioned between water/EtOAc (60 mL/200 mL). Organic layer was dried over anhydrous Na$_2$SO$_4$, concentrated under reduced pressure to obtain crude compound which was subjected to flash column chromatography using 86% EtOAc in hexane as eluent to obtain product (2.48 g, 78.5%) as white solid. $^1$H NMR (400 MHz, DMSO-d$_6$): δ 9.63 (br s, 1H), 8.81-8.75 (m, 2H), 7.94-7.92 (m, 2H), 7.59-7.51 (m, 3H), 7.37 (s, 1H), 3.49-3.44 (m, 2H), 2.40 (t, J=7.5 Hz, 2H), 1.39 (s, 9H); LC-MS: [M+H]$^+$ 375.0.

Step 4: N-(3-hydrazinyl-3-oxopropyl)-5-phenylisoxazole-3-carboxamide hydrochloride: HCl in 1,4-dioxane (4 M HCl solution) was added to a solution of tert-butyl 2-(3-(5-phenylisoxazole-3-carboxamido)propanoyl)hydrazine-1-carboxylate (2.48 g, 6.6 mmol) in 1,4-dioxane (20 mL) and the reaction mixture was stirred at room temperature for 16 h. Volatiles were removed under reduced pressure and the crude reaction mixture was azeotropically distilled with toluene (2×50 mL) to afford hydrochloride salt of the product (2.10 g, 100%) as white solid. $^1$H NMR (400 MHz, DMSO-d$_6$): δ 10.99 (br s, 1H), 10.26 (br s, 3H), 8.87 (t, J=5.6 Hz, 1H), 7.94-7.92 (m, 2H), 7.57-7.53 (m, 3H), 7.38 (s, 1H), 3.56-3.50 (signal obscured by signal of some impurity, 2H), 2.56 (t, J=7.1 Hz, 2H); LC-MS: [M+H]$^+$ 274.9.

Step 5: N-(3-oxo-3-(2-(2-(trifluoromethoxy)acetyl)hydrazinyl)propyl)-5-phenylisoxazole-3-carboxamide: triethylamine (1.48 g, 14.60 mmol), T$_3$P (1.74 g, 5.47 mmol, 50% solution in EtOAc) and N-(3-hydrazinyl-3-oxopropyl)-5-phenylisoxazole-3-carboxamide hydrochloride (1.0 g, 3.65 mmol) were added sequentially to an ice cooled solution of trifluoromethoxy acetic acid (0.48 g, 3.65 mmol) in dry 1,4-dioxane (15 mL) and the resulting reaction mixture was stirred at room temperature for 48 h. Volatiles were removed under reduced pressure and the crude compound was diluted with water. The precipitate thus formed was filtered and dried to get the crude compound which was further purified by silica gel column chromatography using 5% MeOH in DCM as eluent to obtain the product (0.60 g, 41%) as off-white solid. $^1$H NMR (400 MHz, DMSO-d$_6$): δ 10.25 (br, 1H), 10.08 (br, 1H), 8.81 (t, J=5.6 Hz, 1H), 7.94-7.92 (m, 2H), 7.58-7.53 (m, 3H), 7.37 (s, 1H), 4.66 (s, 2H), 3.52-3.47 (m, 2H), 2.49-2.46 (signal obscured by solvent signal, 2H); LC-MS: [M+H]$^+$ 400.7.

Step 6: 5-phenyl-N-(2-(5-((trifluoromethoxy)methyl)-1,3,4-oxadiazol-2-yl)ethyl)isoxazole-3-carboxamide: iodine granules were added to a solution of PPh$_3$ (0.26 g, 1.0 mmol) in DCM (10 mL) and the reaction mixture was cooled to 0° C. To the resulting reaction mixture were added Et$_3$N (0.25 g, 2.5 mmol) and N-(3-oxo-3-(2-(2-(trifluoromethoxy)acetyl)hydrazinyl)propyl)-5-phenylisoxazole-3-carboxamide (0.2 g, 0.50 mmol) sequentially and the reaction mixture was stirred for 4 h at room temperature. Volatiles were removed under reduced pressure to obtain the crude reaction mixture which was suspended in EtOAc (30 mL) and filtered. Filtrate was concentrated to obtain crude compound which was purified by flash column chromatography using 30% EtOAc in hexane as eluent to obtain the product (0.1 g)

Yield: 52.35%

Appearance: off-white solid

Analytical data: $^1$H NMR (400 MHz, CDCl$_3$): δ 7.78-7.76 (m, 2H), 7.51-7.44 (m, 2H), 7.41-7.37 (br, 1H), 6.93 (s, 1H), 5.14 (s, 2H), 3.97 (q, J=6.3 Hz, 2H), 3.23 (t, J=6.3 Hz, 2H).

LC-MS: [M+H]$^+$ 383.1

HPLC purity: 98.18% at 220 nm and 99.08% at 254 nm.

Example 16

5-phenyl-N-(2-(5-((trifluoromethoxy)methyl)-1,3,4-thiadiazol-2-yl)ethyl)isoxazole-3-carboxamide

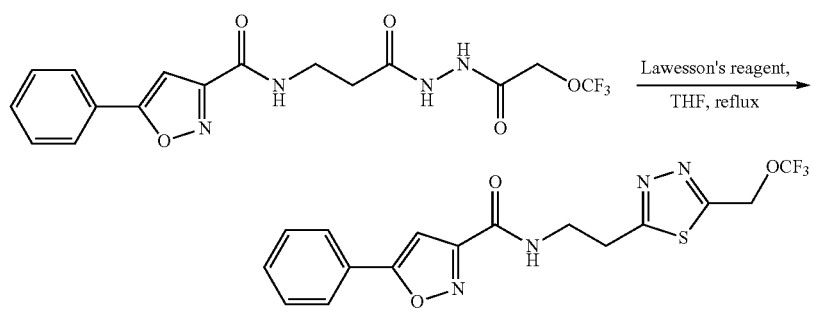

A solution of N-(3-oxo-3-(2-(2-(trifluoromethoxy)acetyl) hydrazinyl)propyl)-5-phenylisoxazole-3-carboxamide (0.4 g, 1.00 mmol) and Lawesson's reagent (1.01 g, 2.50 mmol) in THF (5 mL) was refluxed for 30 min in a sealed tube. To the resulting reaction mixture was added EDC.HCl (0.47 g, 2.50 mmol) and refluxed for 1 h. Then the reaction mixture was partitioned between water/EtOAc (20:60 mL) and separated EtOAc layer was dried over Na$_2$SO$_4$. Organic layer was concentrated under reduced pressure to obtain the crude compound which was further purified by flash column chromatography using 40% EtOAc in hexane as eluent to afford the product (0.11 g).

Yield: 27.6%

Appearance: off-white solid.

Analytical data: $^1$H NMR (400 MHz, CDCl$_3$): δ 7.78-7.76 (m, 2H), 7.51-7.46 (m, 3H), 7.44-7.38 (br, 1H), 6.94 (s, 1H), 5.37 (s, 2H), 3.98 (q, J=6.3 Hz, 2H), 3.46 (t, J=6.3 Hz, 2H).

LC-MS: [M+H]$^+$ 399.0

HPLC purity: 97.48% at 220 nm and 97.23% at 254 nm.

Example 17

(S)-N-(2-(5-(1-hydroxyethyl)-1,3,4-thiadiazol-2-yl) ethyl)-5-phenylisoxazole-3-carboxamide reaction mixture was diluted with water (100 mL). The aq. phase was extracted with ethyl acetate (2×100 mL). Combined organic layer was washed with brine (100 mL), dried over anhydrous Na$_2$SO$_4$ and concentrated under reduced pressure to afford crude compound which was further purified by silica gel (230-400 mesh) column chromatography using 50% EtOAc in hexane as eluent to afford compound 4 (0.650 g, 14% over two steps) as white solid. $^1$H NMR (400 MHz, DMSO): δ 9.98 (s, 1H), 9.44 (s, 1H), 8.80 (t, J=5.6 Hz, 1H), 7.94-7.92 (m, 2H), 7.57-7.53 (m, 3H), 7.35 (s, 1H), 4.29-4.24 (m, 1H), 3.51-3.46 (m, 2H), 2.49-2.44 (m obscured by solvent signal, 2H), 1.27 (d, 3H, J=6.6 Hz), 0.87 (s, 9H), 0.08 (s, 6H); LC-MS: [M+H]$^+$ 461.0.

Step 2: (S)-N-(2-(5-(1-((tert-butyldimethylsilyl)oxy) ethyl)-1,3,4-thiadiazol-2-yl)ethyl)-5-phenylisoxazole-3-carboxamide: Lawesson's reagent (0.63 g, 1.56 mmol) was added to a solution of (R)-N-(3-(2-(2-((tert-butyldimethylsilyl)oxy)propanoyl)hydrazinyl)-3-oxopropyl)-5-phenylisoxazole-3-carboxamide (0.36 g, 0.78 mmol) in THF (50 mL) and the reaction mixture was heated to 110° C. for 2 h. Then the reaction mixture was diluted with water (25 mL) and extracted with ethyl acetate (2×20 mL). Combined

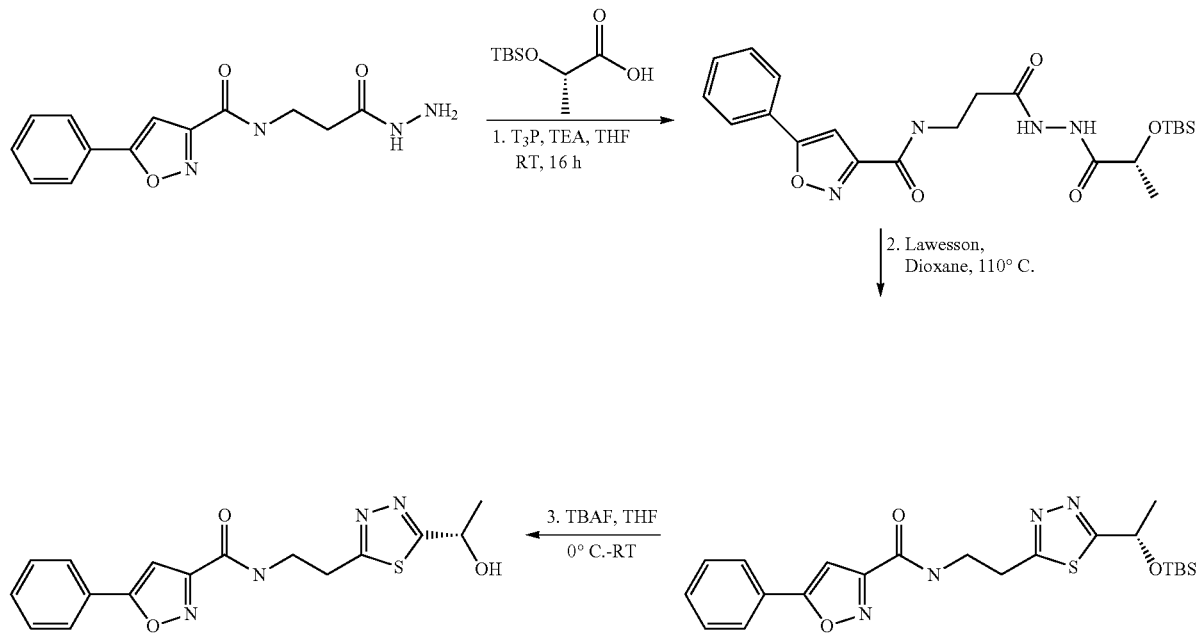

Step 1: (R)-N-(3-(2-(2-((tert-butyldimethylsilyl)oxy)propanoyl)hydrazinyl)-3-oxopropyl)-5-phenylisoxazole-3-carboxamide: TEA (1.96 mL, 14.5 mmol) and T$_3$P (3.47 mL, 5.4 mmol) were added to an ice-cooled solution of (S)-2-((tert-butyldimethylsilyl)oxy)propanoic acid (0.89 g, crude) and (R)-N-(3-(2-(2-((tert-butyldimethylsilyl)oxy)propanoyl)hydrazinyl)-3-oxopropyl)-5-phenylisoxazole-3-carboxamide (1 g, 3.6 mmol) in dioxane (50 mL) and the reaction mixture was stirred for 3 h at room temperature. Volatiles were removed under reduced pressure and the organic layer was washed with brine (20 mL), dried over anhydrous Na$_2$SO$_4$ and concentrated under reduced pressure to afford crude compound which was purified by silica gel (230-400 mesh) column chromatography using 30% EtOAc in hexane as eluent to obtain the product (0.220 g, 61%) as off-white solid. $^1$H NMR (400 MHz, CDCl$_3$): δ 7.79-7.76 (m, 2H), 7.55-7.52 (m, 1H), 7.48-7.46 (m, 3H), 5.24-5.22 (m, 1H), 3.97-3.95 (m, 2H), 3.40 (t, J=6.3 Hz, 2H), 1.59 (d, J=6.4 Hz, 3H), 0.89 (s, 9H), 0.11 (s, 3H), 0.05 (s, 3H); LC-MS: [M+H]$^+$ 459.2.

Step 3: (S)-N-(2-(5-(1-hydroxyethyl)-1,3,4-thiadiazol-2-yl)ethyl)-5-phenylisoxazole-3-carboxamide: TBAF (1 M solution in THF) (0.9 mL, 0.87 mmol) was added to an ice-cooled solution of (S)-N-(2-(5-(1-((tert-butyldimethylsilyl)oxy)ethyl)-1,3,4-thiadiazol-2-yl)ethyl)-5-phenylisoxazole-3-carboxamide (0.2 g, 0.43 mmol) in THF (20 mL) and the reaction mixture was stirred for 2 h at room temperature. Volatiles were removed under reduced pressure and the crude reaction mixture was diluted with water (30 mL). The aq. phase was extracted with ethyl acetate (2×40 mL). Combined layer was washed with brine (20 mL), dried over anhydrous Na$_2$SO$_4$ and concentrated under reduced pressure to afford crude compound which was washed with diethyl ether and n-pentane to obtain the product (0.12 g).

Appearance: off white solid

Analytical data: $^1$H NMR (400 MHz, DMSO): δ 9.01 (t, J=5.8 Hz, 1H), 7.94-7.92 (m, 2H), 7.58-7.53 (m, 3H), 7.36 (s, 1H), 5.93-5.91 (d, 1H), 4.91-4.84 (m, 1H), 3.67-3.62 (m, 2H) 3.12 (t, J=6.9 Hz, 2H), 1.43 (d, J=6.6 Hz, 3H).

LC-MS: [M+H]$^+$ 329.0

HPLC purity: 98.70% at 270 nm and 96.34% at 220 nm.

Example 19

(R)-N-(2-(5-(1,2-dihydroxyethyl)-1,3,4-oxadiazol-2-yl)ethyl)-5-phenylisoxazole-3-carboxamide

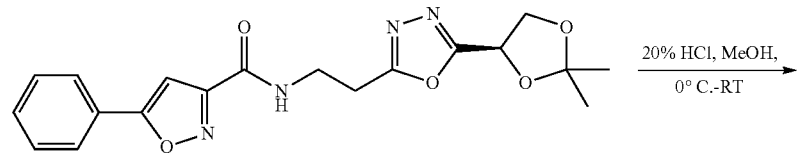

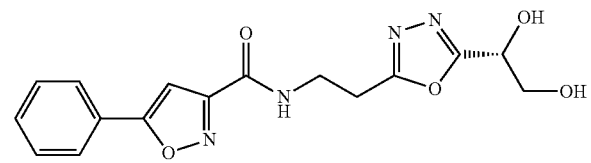

Yield: 62%

Appearance: off white solid

Analytical data: $^1$H NMR (400 MHz, DMSO): δ 9.04 (t, J=5.7 Hz, 1H), 7.95-7.92 (m, 2H), 7.57-7.54 (m, 3H), 7.37 (s, 1H), 6.27 (d, J=5 Hz, 1H), 5.06-5.03 (m, 1H), 3.67-3.62 (m, 2H), 3.36-3.32 (m obscured by solvent signal, 2H), 1.47 (d, J=6.4 Hz, 3H).

LC-MS: [M+H]$^+$ 344.9

HPLC: 99.21% at 254 nm and 99.17% at 200 nm.

Example 18

(S)-N-(2-(5-(1-hydroxyethyl)-1,3,4-oxadiazol-2-yl)ethyl)-5-phenylisoxazole-3-carboxamide This compound was prepared following the procedure described in example 14.

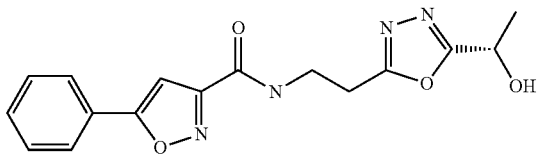

20% aq. HCl (10 mL) was added to an ice cooled solution of (R)-N-(2-(5-(2,2-dimethyl-1,3-dioxolan-4-yl)-1,3,4-oxadiazol-2-yl)ethyl)-5-phenylisoxazole-3-carboxamide (prepared using the procedure described in example 14 using methyl (R)-2,2-dimethyl-1,3-dioxolane-4-carboxylate) (0.3 g, 0.7821 mmol) in methanol (20 mL) and the reaction mixture was stirred for 2 h at room temperature. Volatiles were removed under reduced pressure, basified with saturated NaHCO$_3$ solution and extracted with EtOAc (3×50 mL). Combined organic layer was dried over anhydrous sodium sulfate and concentrated under reduced pressure to obtain the crude product. The crude product was chromatographed on silica gel (230-400 mesh) using 1% MeOH in EtOAc as eluent to afford the product (50 mg, 13% over two steps) as a white solid.

Analytical data: $^1$H NMR (400 MHz, DMSO-d$_6$): δ 9.01 (t, J=5.7 Hz, 1H), 7.95-7.92 (m, 2H), 7.57-7.53 (m, 3H), 7.37 (s, 1H), 6.04 (d, J=5.7 Hz, 1H), 4.96 (t, J=6.0 Hz, 1H), 4.72 (q, J=6.3 Hz, 1H), 3.68-3.63 (m, 4H), 3.13 (t, J=7.1 Hz, 2H).

LC-MS: [M+H]$^+$=344.9

HPLC purity: 97.78% at 254 nm and 96.45% at 220 nm.

Example 20

(R)-N-(2-(5-(1,2-dihydroxyethyl)-1,3,4-thiadiazol-2-yl)ethyl)-5-phenylisoxazole-3-carboxamide

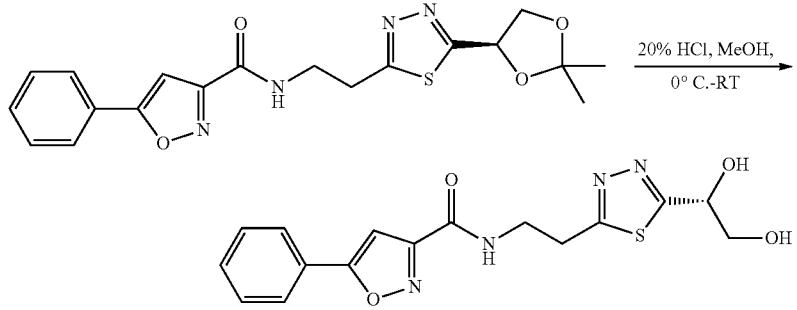

20% HCl (8 mL) was added to an ice cooled solution of (R)-N-(2-(5-(2,2-dimethyl-1,3-dioxolan-4-yl)-1,3,4-thiadiazol-2-yl)ethyl)-5-phenylisoxazole-3-carboxamide (0.15 g, 0.375 mmol, prepared according procedure described in example 17 using methyl (R)-2,2-dimethyl-1,3-dioxolane-4-carboxylate) in methanol (15 mL)and the reaction mixture was stirred for 2 h at room temperature. Volatiles were removed under reduced pressure, basified with saturated NaHCO$_3$ solution and extracted with EtOAc. Separated organic layer was dried over anhydrous Na$_2$SO$_4$ and concentrated under reduced pressure to afford crude compound. The crude compound was purified by silica gel (100-200 mesh) column chromatography using 2%-MeOH in EtOAc as eluent to obtain the product(60 mg, 45%) as off white solid.

Analytical data: $^1$H NMR (400 MHz, DMSO-d$_6$): δ 9.04 (t, J=5 Hz,1H), 7.94-7.92 (m, 2H), 7.57-7.53 (m, 3H), 7.36 (s, 1H), 4.90 (dd, J=6.0, 4.6 Hz, 1H), 3.71-3.63 (m, 3H), 3.57 (dd, J=11.3, 6.1 Hz, 1H), 3.36-3.32 (m, 2H).

LC-MS: [M+H]$^+$=361.2

HPLC Purity: 96.87% at 254 nm and 97.52% at 220 nm.

Example 21

(S)-N-(2-(5-(1,2-dihydroxyethyl)-1,3,4-thiadiazol-2-yl)ethyl)-5-phenyl isoxazole-3-carboxamide This compound was prepared using the procedure described in example 17 using methyl (S)-2,2-dimethyl-1,3-dioxolane-4-carboxylate as the starting material.

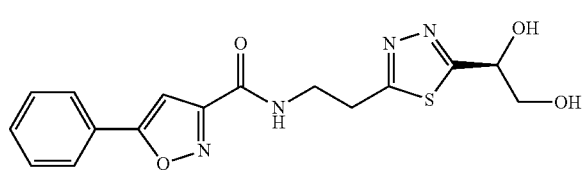

Appearance: off white solid

Analytical data: $^1$H NMR (400 MHz, DMSO-d$_6$): δ 9.04 (t, J=5.7 Hz, 1H), 7.95-7.92 (m, 2H), 7.57-7.54 (m, 3H), 7.37 (s, 1H), 6.33 (d, J=5.1 Hz, 1H), 5.04 (t, J=6.0 Hz, 1H), 4.92-4.88 (m, 1H), 3.72-3.63 (m, 3H), 3.60-3.55 (m, 1H), 3.36-3.33 (m, 2H).

LC-MS: [M+H]$^+$=361.0

HPLC purity: 96.29% at 220 nm and 95.87% at 254 nm.

Example 22

(S)-N-(2-(5-(1,2-dihydroxyethyl)-1,3,4-oxadiazol-2-yl)ethyl)-5-phenyl isoxazole-3-carboxamide carboxamide This compound was prepared using the procedure described in example 14 using methyl (S)-2,2-dimethyl-1,3-dioxolane-4-carboxylate as the starting material.

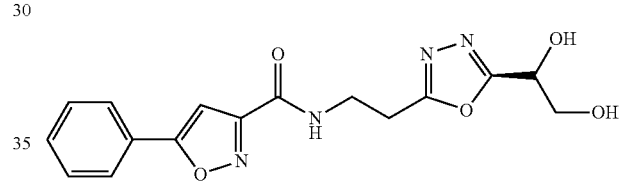

Example 23

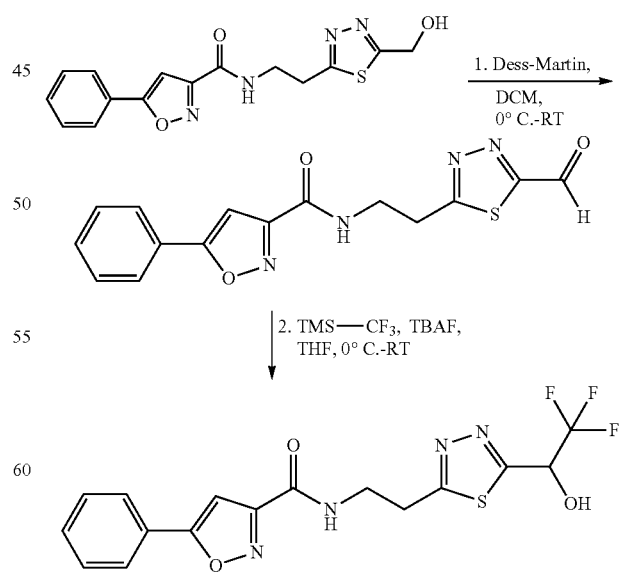

Step 1: N-(2-(5-formyl-1,3,4-thiadiazol-2-yl)ethyl)-5-phenylisoxazole-3-carboxamide: Dess-Martin periodinane (0.7 g, 4.5 mmol) was added to an ice cooled solution of N-(2-(5-(hydroxymethyl)-1,3,4-thiadiazol-2-yl)ethyl)-5-phenylisoxazole-3-carboxamide (1 g, 3.03 mmol) in DCM (50 mL) and the resultant reaction mixture was stirred at room temperature for 24 h. Then the reaction mixture was poured onto saturated NaHCO₃ solution (80 mL) and extracted with DCM (2×50 mL). Combined organic layer was washed with sodium thiosulfate solution followed by water and brine. Combined organic layer was dried over anhydrous Na₂SO₄ and concentrated under reduced pressure to afford crude compound. The crude compound was purified by silica gel (100-200 mesh) column chromatography using 5% methanol in DCM as eluent to obtain the product (0.8 g, 80%) as off-white solid. $^1$H NMR (400 MHz, DMSO): δ 10.13 (s, 1H), 9.09-9.06 (br, 1H), 7.94-7.92 (m, 2H), 7.57-7.54 (m, 3H), 7.37 (s, 1H), 3.72 (q, J=6.3 Hz, 2H), 3.53-3.50 (m, 2H); LC-MS: [M+H]$^+$ 329.1.

Step 2: 5-phenyl-N-(2-(5-(2,2,2-trifluoro-1-hydroxyethyl)-1,3,4-thiadiazol-2-yl)ethyl)isoxazole-3-carboxamide: (trifluoromethyl)trimethylsilane (0.48 mL, 3.4 mmol) was added to an ice cooled solution of N-(2-(5-formyl-1,3,4-thiadiazol-2-yl)ethyl)-5-phenylisoxazole-3-carboxamide (0.8 g, 2.4 mmol) in THF (50 mL) followed by tetrabutyl ammonium fluoride (1M THF) (0.015 mL, 0.00733 mmol) and the resultant reaction mixture was stirred at room temperature for 24 h. The reaction mixture was quenched with saturated ammonium chloride solution and extracted with DCM (2×10 mL). Combined organic layer was washed with brine, dried over anhydrous Na₂SO₄ and concentrated under reduced pressure to obtain the crude compound which was purified by flash column chromatography using 5% methanol in DCM as eluent to afford a racemic mixture (0.08 g, 8%) as off-white solid. The racemic mixture was further separated by chiral preparative HPLC to obtain pure Isomer-I and II.

Isomer-I: Yield: 0.01 g; off-white solid; $^1$H NMR (400 MHz, CDCl₃+2-drops DMSO): δ 7.75-7.73 (m, 2H), 7.65 (br, 1H), 7.46-7.43 (m, 3H), 7.12 (br, 1H), 6.91 (s, 1H), 5.46-5.41 (m, 1H), 3.93 (q, J=6.4 Hz, 2H), 3.41 (t, J=6.4 Hz, 2H).

LC-MS: [M+H]$^+$ 398.8

HPLC Purity: 99.29% at 220 nm and 99.10% at 254 nm.

Isomer-II: Yield: 0.02 g; off-white solid; $^1$H NMR (400 MHz, CDCl₃+2-drops DMSO): δ 7.74-7.72 (m, 3H), 7.44-7.41 (m, 3H), 7.21 (br, 1H), 6.89 (s, 1H), 5.42 (q, J=6.4 Hz, 1H), 3.90 (q, J=6.4 Hz, 2H), 3.40 (t, J=6.4 Hz, 2H).

LC-MS: [M+H]$^+$ 399.1

HPLC Purity: 98.69% at 220 nm and 98.75% at 254 nm.

Example 24

Preparation of (R)-N-(2-(5-(1-methoxyethyl)-1,3,4-oxadiazol-2-yl)ethyl)-5-phenylisoxazole-3-carboxamide and (S)-N-(2-(5-(1-methoxyethyl)-1,3,4-oxadiazol-2-yl)ethyl)-5-phenylisoxazole-3-carboxamide

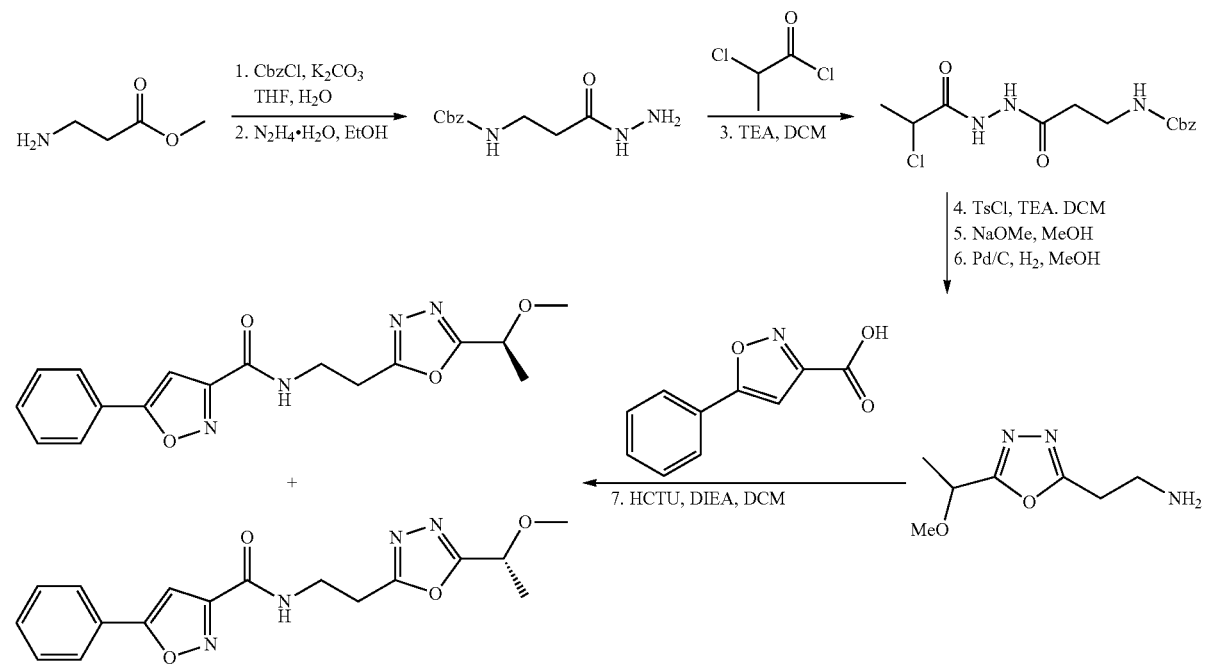

Step 1: methyl 3-[[(benzyloxy)carbonyl]amino]propanoate: K₂CO₃ (118.3 g, 849.77 mmol, 3.00 equiv) and benzyl chloroformate (58.7 g, 344.09 mmol, 1.20 equiv) were added dropwise to a 0° C. solution of 3-aminopropanoate hydrochloride (40 g, 286.74 mmol, 1.00 equiv) in tetrahydrofuran/water (500/300 mL) in 20 min. The resulting solution was stirred for 3 hours at 25° C. and then diluted with 500 mL of water. The resulting solution was extracted with ethyl acetate (3×500 mL) and the organic layers combined. The resulting mixture was washed with brine (2×500 mL), dried over anhydrous sodium sulfate and concentrated under vacuum. This resulted in 60 g (88%) of methyl 3-[[(benzyloxy)carbonyl]amino]propanoate as a white solid. LC-MS: [M+H]$^+$=238.

Step 2: benzyl N-[2-(hydrazinecarbonyl)ethyl]carbamate: a solution of methyl 3-[[(benzyloxy)carbonyl]amino]propanoate (60 g, 252.90 mmol, 1.00 equiv) in ethanol (500 mL) and NH₂NH₂H₂O (65 mL, 80%) was stirred for 3 hours at 80° C. The resulting mixture was concentrated under vacuum. The residue was recrystallized from petroleum ether\ethyl acetate (3:1). This resulted in 51 g (85%) of benzyl N-[2-(hydrazinecarbonyl)ethyl]carbamate as a white solid. LC-MS: [M+H]$^+$=238.

Step 3: of benzyl N-[2-[N-(2-chloropropanoyl)hydrazinecarbonyl]ethyl]carbamate: 2-chloropropanoyl chloride (25.2 g, 198.47 mmol, 1.00 equiv) was added dropwise to a 0° C. a solution of benzyl N-[2-(hydrazinecarbonyl)ethyl]carbamate (51 g, 214.96 mmol, 1.00 equiv) and TEA (43.4 g, 428.90 mmol, 2.00 equiv) in tetrahydrofuran (500 mL). The resulting solution was stirred for 1 hour at 25° C., diluted with 700 mL of water and then extracted with ethyl acetate (3×500 mL) and the organic layers combined. The resulting mixture was washed with brine (3×500 mL), dried over anhydrous sodium sulfate and concentrated under vacuum. The residue was applied onto a silica gel column with ethyl acetate/petroleum ether (1:5) to give 42 g (60%) of benzyl N-[2-[N-(2-chloropropanoyl)hydrazinecarbonyl]ethyl]carbamate as a white solid. LC-MS: [M+H]$^+$=328.

Step 4: of benzyl N-[2-[5-(1-chloroethyl)-1,3,4-oxadiazol-2-yl]ethyl]carbamate: methylbenzene-1-sulfonyl chloride (5.6 g, 29.37 mmol, 1.20 equiv) was added to a solution of benzyl N-[2-[N-(2-chloropropanoyl)hydrazinecarbonyl]ethyl]carbamate (8 g, 24.41 mmol, 1.00 equiv) and TEA (4.8 g, 47.44 mmol, 2.00 equiv) in dichloromethane (250 mL) and the mixture was stirred for 16 hours at 25° C. The resulting solution was diluted with 800 mL of ethyl acetate, washed with brine (2×500 mL), dried over anhydrous sodium sulfate and concentrated under vacuum. The crude product was purified by Flash-Prep-HPLC with the following conditions (IntelFlash-1): Column, C18 silica gel; mobile phase, CAN/H$_2$O=10/90 increasing to 80/20 within 30 min; Detector, UV 220 nm to give 4.5 g (60%) of benzyl N-[2-[5-(1-chloroethyl)-1,3,4-oxadiazol-2-yl]ethyl]carbamate as a yellow solid. LC-MS: [M+H]$^+$=310.

Step 5: benzyl N-[2-[5-(1-methoxyethyl)-1,3,4-oxadiazol-2-yl]ethyl]carbamate: sodium methoxide(518 mg, 9.59 mmol, 1.50 equiv) was added to a solution of benzyl N-[2-[5-(1-chloroethyl)-1,3,4-oxadiazol-2-yl]ethyl]carbamate (2 g, 6.46 mmol, 1.00 equiv) in methanol (50 mL) and the reaction mixture was stirred for 16 hours at 25° C. The resulting solution was diluted with 200 mL of water, extracted with ethyl acetate (2×300 mL) and the organic layers combined. The resulting mixture was washed with brine (2×300 mL), dried over anhydrous sodium sulfate and concentrated under vacuum to give 550 mg (28%) of benzyl N-[2-[5-(1-methoxyethyl)-1,3,4-oxadiazol-2-yl]ethyl]carbamate as yellow oil. LC-MS: [M+H]$^+$=306.

Step 6: 2-[5-(1-methoxyethyl)-1,3,4-oxadiazol-2-yl]ethan-1-amine: palladium on carbon (50 mg) was added to a solution of benzyl N-[2-[5-(1-methoxyethyl)-1,3,4-oxadiazol-2-yl]ethyl]carbamate (550 mg, 1.80 mmol, 1.00 equiv) in methanol (10 mL). The resulting solution was degassed and back filled with hydrogen gas and the mixture was stirred for 3 hours at 25° C. under hydrogen atmosphere. After removing the solids by filtration, the resulting mixture was concentrated under vacuum to give 172 mg (56%) of 2-[5-(1-methoxyethyl)-1,3,4-oxadiazol-2-yl]ethan-1-amine as a yellow solid. LC-MS: [M+H]$^+$=172.

Step 7: (R and S)-N-(2-(5-(1-methoxyethyl)-1,3,4-oxadiazol-2-yl)ethyl)-5-phenylisoxazole-3-carboxamide: a solution of 2-[5-(1-methoxyethyl)-1,3,4-oxadiazol-2-yl]ethan-1-amine (172 mg, 1.00 mmol, 1.00 equiv), DIEA (260 mg, 2.01 mmol, 2.00 equiv), HCTU (480 mg, 1.15 mmol, 1.20 equiv) and 5-phenyl-1,2-oxazole-3-carboxylic acid (190 mg, 1.00 mmol, 1.00 equiv) in dichloromethane (10 mL) was stirred for 2 hours at 25° C. The resulting solution was diluted with 50 mL of water, ethyl acetate (2×50 mL) and the organic layers combined. The resulting mixture was washed with brine (2×50 mL), dried over anhydrous sodium sulfate and concentrated under vacuum. The crude product was purified by Prep-TLC (petroleum ether:ethyl acetate=2:1). The resulting isomers were separated by Chiral-Prep-HPLC with the following conditions (Prep-HPLC-009): Column, chiral pak AS-H, 2*25CM; mobile phase, Hex and ethanol (hold 10.0% ethanol in 30 min); Detector, UV 254/220nm. This resulted in 35.5 mg of Isomer I as a white solid and 38.6 mg of Isomer II as a white solid. LC-MS: [M+H]$^+$=

Isomer I:
LC-MS: [M+H]$^+$=343
Analytical data: $^1$H NMR (300MHz, DMSO-d$_6$): δ: 9.03-8.99 (m, 1H), 7.96-7.93 (m, 2H), 7.57-7.55 (m, 3H), 7.35 (s, 1H), 4.69-4.62 (m, 1H), 3.70-3.64 (m, 2H), 3.25 (s, 3H), 3.17-3.13 (m, 2H), 1.47-1.44 (d, J=6.6 Hz, 2H).
HPLC purity: 98.8% at 254 nm.

Isomer II
LC-MS: [M+H]$^+$=343
Analytical data: $^1$H NMR (300MHz, DMSO-d$_6$): δ: 9.03-8.99 (m, 1H), 7.96-7.93 (m, 2H), 7.60-7.55 (m, 3H), 7.35 (s, 1H), 4.69-4.62 (m, 1H), 3.70-3.64 (m, 2H), 3.25 (s, 3H), 3.17-3.13 (m, 2H), 1.47-1.44 (d, J=6.6Hz, 2H).
HPLC purity: 98.9% at 254 nm.

Example 25

Preparation of (S)-N-(2-(5-(1-methoxyethyl)-1,3,4-thiadiazol-2-yl)ethyl)-5-phenylisoxazole-3-carboxamide and (R)-N-(2-(5-(1-methoxyethyl)-1,3,4-thiadiazol-2-yl)ethyl)-5-phenylisoxazole-3-carboxamide

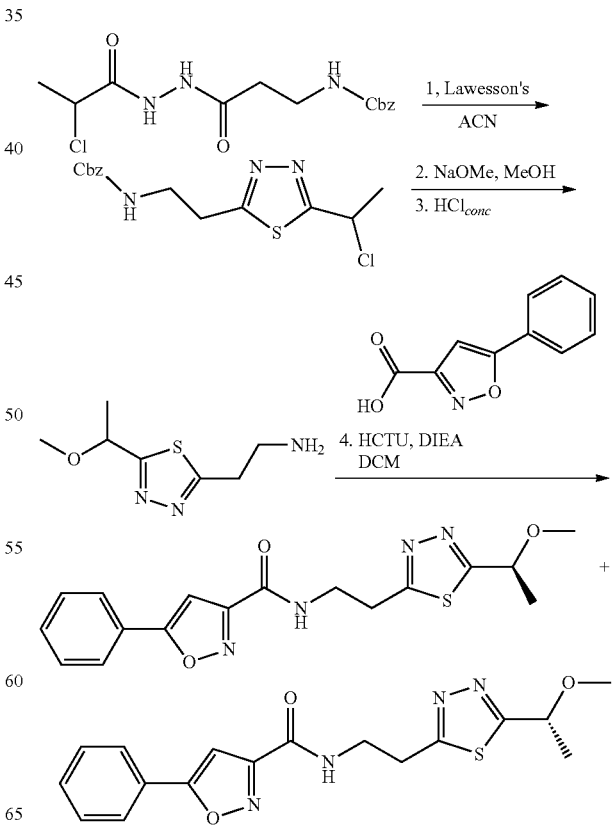

Step 1: of benzyl N-[2-[5-(1-chloroethyl)-1,3,4-thiadiazol-2-yl]ethyl]carbamate: Lawesson's reagent (4.6 g, 11.37 mmol, 1.00 equiv) was added to a solution of benzyl N-[2-[N-(2-chloropropanoyl)hydrazinecarbonyl]ethyl]carbamate (4 g, 12.20 mmol, 1.00 equiv) in ACN (100 mL) and the solution was stirred for 2 hours at 60° C. The reaction mixture was diluted with 300 mL of water, extracted with ethyl acetate (2×300 mL) and the organic layers combined. The mixture was washed with brine (2×300 mL), dried over anhydrous sodium sulfate and concentrated under vacuum. The residue was applied onto a silica gel column with ethyl acetate/petroleum ether (1:5). The crude product was purified by Flash-Prep-HPLC with the following conditions (IntelFlash-1): Column, C18 silica gel; mobile phase, ACN:$H_2O$=5/95 increasing to CAN:$H_2O$=80/20 within 30 min; Detector, UV 254 nm to give 1.9 g (48%) of benzyl N-[2-[5-(1-chloroethyl)-1,3,4-thiadiazol-2-yl]ethyl]carbamate as a yellow solid. LC-MS: $[M+H]^+$=326.

Step 2: of benzyl N-[2-[5-(1-methoxyethyl)-1,3,4-thiadiazol-2-yl]ethyl]carbamate: sodium methoxide (1.57 g, 8.72 mmol, 1.50 equiv) was added to a solution of benzyl N-[2-[5-(1-chloroethyl)-1,3,4-thiadiazol-2-yl]ethyl]carbamate (1.9 g, 5.83 mmol, 1.00 equiv) in methanol (20 mL) under $N_2$ and the mixture was stirred for 16 hours at 25° C. The reaction mixture was diluted with 100 mL of water, extracted with ethyl acetate (2×100 mL) and the organic layers combined. The resulting mixture was washed with brine (2×100 mL), dried over anhydrous sodium sulfate and concentrated under vacuum. The residue was applied onto a silica gel column with ethyl acetate/petroleum ether (1:7) to give 950 mg (51%) of benzyl N-[2-[5-(1-methoxyethyl)-1,3,4-thiadiazol-2-yl]ethyl]carbamate as a yellow solid. LC-MS: $[M+H]^+$=322.

Step 3: 2-[5-(1-methoxyethyl)-1,3,4-thiadiazol-2-yl]ethan-1-amine hydrochloride: hydrogen chloride aqueous (6N, 10 mL) was added to a solution of benzyl N-[2-[5-(1-methoxyethyl)-1,3,4-thiadiazol-2-yl]ethyl]carbamate (950 mg, 2.96 mmol, 1.00 eq.) and the mixture was stirred for 1 hour at 80° C. The resulting mixture was concentrated under vacuum. This resulted in 550 mg (83%) of 2-[5-(1-methoxyethyl)-1,3,4-thiadiazol-2-yl]ethan-1-amine hydrogen chloride salt as a yellow solid. LC-MS: $[M+H]^+$=188.

Step 4: (R/S)-N-(2-(5-(1-methoxyethyl)-1,3,4-thiadiazol-2-yl)ethyl)-5-phenylisoxazole-3-carboxamide: HCTU (1.7 g, 4.08 mmol, 1.50 equiv), DIEA (948 mg, 7.34 mmol, 3.00 equiv) and 5-phenyl-1,2-oxazole-3-carboxylic acid (465 mg, 2.46 mmol, 1.00 equiv) were added to a solution of 2-[5-(1-methoxyethyl)-1,3,4-thiadiazol-2-yl]ethan-1-amine hydrochloride salt (550 mg, 2.46 mmol, 1.00 equiv) in dichloromethane (10 mL). The resulting solution was stirred for 3 hours at 25° C., diluted with 100 mL of ethyl acetate. The resulting mixture was washed with brine (2×50 mL), dried over anhydrous sodium sulfate and concentrated under vacuum. The crude product was purified by Prep-HPLC with the following conditions (Waters): Column, Xbridge Prep shield RP18, 5 nm, 19×150 mm; mobile phase, $CH_3CN/H_2O$(with 0.05% $NH_4HCO_3$)=30% increasing to $CH_3CN/H_2O$(with 0.05% $NH_4HCO_3$)=60% within 8 min; Detector, UV 254 nm. The pure isomers were separated by Chiral-Prep-HPLC with the following conditions (Prep-HPLC-032): Column, Phenomenex Lux 5u Cellulose-4AXIA Packed, 250*21.2 mm,5 um; mobile phase, Hex and ethanol (hold 30.0% ethanol in 35 min); Detector, UV 254/220nm. This resulted in 53.4 mg of Isomer I as a white solid and 50.9 mg of Isomer II as a white solid.

Isomer I:
LC-MS: $[M+H]^+$=359
Analytical data: $^1$H NMR (300MHz, DMSO-$d_6$): δ: 9.03-9.01 (m, 1H), 7.95-7.92 (m, 2H), 7.60-7.54 (m, 3H), 7.36 (s, 1H), 4.84-4.77 (m, 1H), 3.70-3.63 (m, 2H), 3.39-3.35 (m, 2H), 3.28 (s, 3H), 1.50-1.47 (d, J=6.6Hz, 2H).
HPLC purity: 98.60% at 254 nm.

Isomer II:
LC-MS: $[M+H]^+$=359
Analytical data: $^1$H NMR (300MHz, DMSO-$d_6$): δ: 9.05-9.02 (m, 1H), 7.95-7.92 (m, 2H), 7.58-7.54 (m, 3H), 7.36 (s, 1H), 4.84-4.79 (m, 1H), 3.70-3.64 (m, 2H), 3.40-3.35 (m, 2H), 3.28 (s, 3H), 1.50-1.47 (d, J=6.6Hz, 2H).
HPLC purity: 98.6% at 254 nm.

Example 26

CFTR Activity Assays i. Ussing Measurements

As discussed above, Ussing measurements can be used to measure CFTR activity. In this method, primary lung epithelial cells (hBEs) homozygous for the Cystic Fibrosis-causing ΔF508 mutation are differentiated for a minimum of 4 weeks in an air-liquid interface on SnapWell filter plates prior to the Ussing measurements. Cells are apically mucus-washed for 30 minutes prior to treatment with compounds. The basolateral media is removed and replaced with media containing the compound of interest diluted to its final concentration from DMSO stocks. Treated cells are incubated at 37° C. and 5% $CO_2$ for 24 hours. At the end of the treatment period, the cells on filters are transferred to the Ussing chamber and equilibrated for 30 minutes. The short-circuit current is measured in voltage clamp-mode ($V_{hold}$=0 mV), and the entire assay is conducted at a temperature of 36° C.-36.5° C. Once the voltages stabilized, the chambers are clamped, and data is recorded by pulse readings every 5 seconds. Following baseline current stabilization, the following additions can be applied and the changes in current and resistance of the cells can be monitored:

1. Benzamil to the apical chamber to inhibit ENaC sodium channel.
2. Forskolin to both chambers to activate ΔF508-CFTR by phosphorylation.
3. Genistein to both chambers to potentiate ΔF508-CFTR channel opening.
4. CFTRinh-172 to the apical chamber to inhibit ΔF508-CFTR Cl-conductance.

The inhibitable current (that current that is blocked by CFTRinh-172) is measured as the specific activity of the ΔF508-CFTR channel, and increases in response to compound in this activity over that observed in vehicle-treated samples are identified as the correction of ΔF508-CFTR function imparted by the compound tested.

ii. hBE Equivalent Current (Ieq) Assay

Primary lung epithelial cells homozygous for the Cystic Fibrosis-causing ΔF508 mutation were differentiated for a minimum of 4 weeks in an air-liquid interface on Costar 24 well HTS filter plates prior to the equivalent current (Ieq) measurements. Cells were apically mucus-washed for 30 minutes 24 h prior to treatment with compounds. The basolateral media was removed and replaced with media containing the compound of interest diluted to its final concentration from DMSO stocks. Treated cells were incubated at 37° C. and 5% $CO_2$ for 24 hours. At the end of the treatment period, the media was changed to the Ieq experimental solution for 30 minutes before the experiment and plates are maintained in a $CO_2$-free incubator during this period. The plates containing the cells were then placed in pre-warmed heating blocks at 36° C.±0.5 for 15 minutes before measurements are taken. The transepithelial voltage ($V_T$) and conductance ($G_T$) were measured using a custom 24 channel current clamp (TECC-24) with 24 well electrode manifold. The Ieq assay measurements were made following additions with standardized time periods:
1. The baseline $V_T$ and $G_T$ values were measured for approximately 20 minutes.
2. Benzamil was added to block ENaC for 15 minutes.
3. Forskolin plus VX-770 were added to maximally activate ΔF508-CFTR for 27 minutes.
4. Bumetanide was added to inhibit the $NaK_2Cl$ cotransporter and shut-off secretion of chloride.

The activity data captured was the area under the curve (AUC) for the traces of the equivalent chloride current. The AUC was collected from the time of the forskolin/VX-770 addition until the inhibition by bumetanide addition. Correction in response to compound treatment was scored as the increase in the AUC for compound-treated samples over that of vehicle-treated samples. The results are shown below in Table 2 (++indicates activity ≥25% run at 10 uM of VX-809 at 1 uM; +indicates activity 10 to <25% run at 10 uM of VX-809 at 1 uM; ** indicates activity ≥200% of VX-809 (1 uM) with compound at 10 uM and VX-809 at 1 uM; * indicates activity 100-200% of VX-809 (1 uM) with compound at 10 uM and VX-809 at 1 uM)

TABLE 2

| Compound | Structure | Ieq Activity | Ussing |
|---|---|---|---|
| A1 (Example 6) | 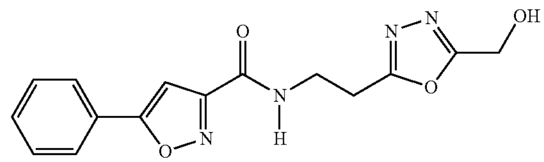 | ++, | ++, |
| A2 (Example 3) | 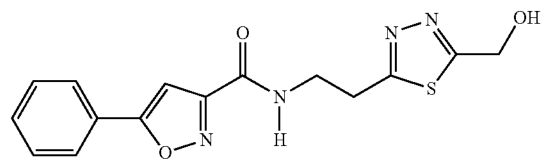 [SMILES: O=C(NCCc1nnc(CO)s1)c1cc(-c2ccccc2)on1] | ++, | ++, |
| A3 (Example 4) | 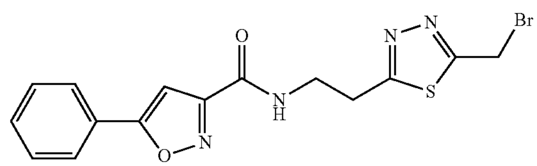 [SMILES: O=C(NCCc1nnc(CBr)s1)c1cc(-c2ccccc2)on1] | ** | |
| A4 (Example 2) | 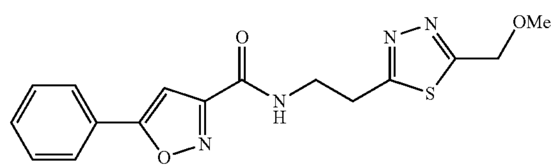 [SMILES: COCc1nnc(CCNC(=O)c2cc(-c3ccccc3)on2)s1] | ** | |
| A5 (Example 5) | 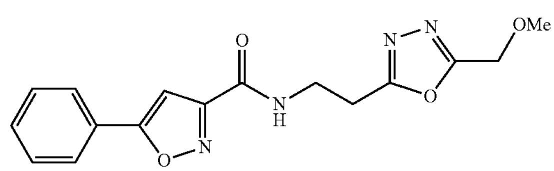 [SMILES: COCc1nnc(CCNC(=O)c2cc(-c3ccccc3)on2)o1] | ** | |
| A6 (Example 1) | 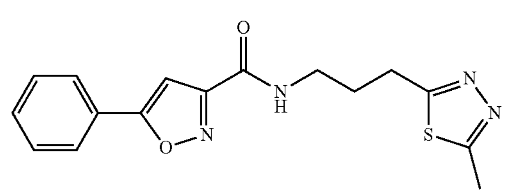 [SMILES: Cc1nnc(CCCNC(=O)c2cc(-c3ccccc3)on2)s1] | ** | |

TABLE 2-continued

| Compound | Structure | Ieq Activity Ussing |
|---|---|---|
| A7 (Example 7) | 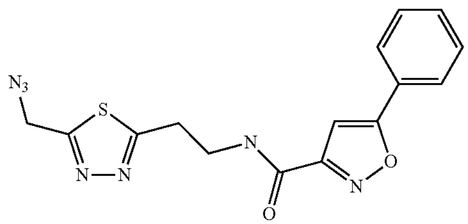 [SMILES: [N-]=[N+]=NCc1nnc(CCNC(=O)c2cc(-c3ccccc3)on2)s1] | ** |
| A8 (Example 8) | 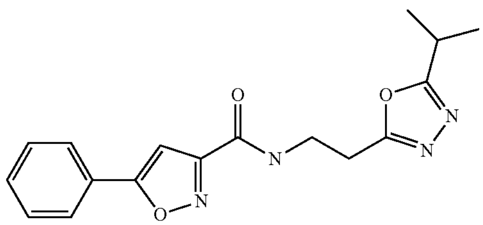 [SMILES: CC(C)c1nnc(CCNC(=O)c2cc(-c3ccccc3)on2)o1] | ** |
| A9 (Example 9) | 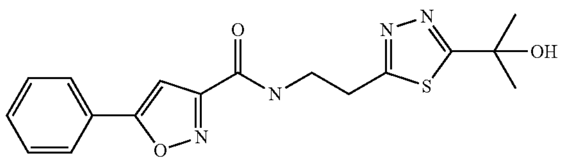 | ** |
| A10 (Example 10) | 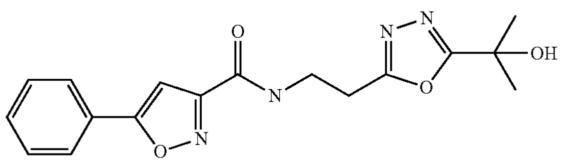 | ** |
| A11 (Example 11) | 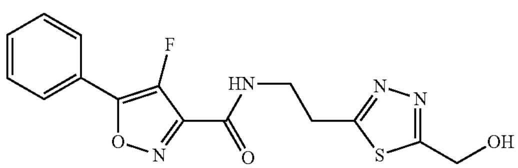 [SMILES: O=C(NCCc1nnc(CO)s1)c1noc(-c2ccccc2)c1F] | * |
| A12 (Example 12) | 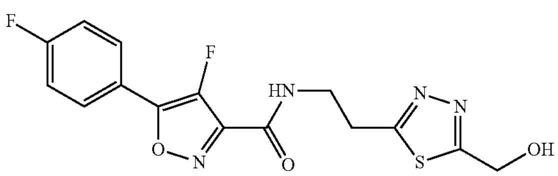 [SMILES: O=C(NCCc1nnc(CO)s1)c1noc(-c2ccc(F)cc2)c1F] | * |
| A13 (Example 13) | 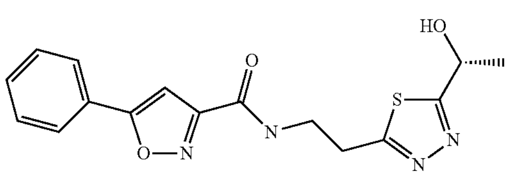 [SMILES: C[C@@H](O)c1nnc(CCNC(=O)c2cc(-c3ccccc3)on2)s1] | ** |
| A14 (Example 14) | 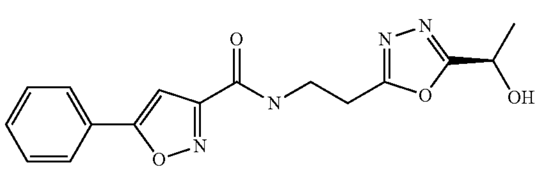 [SMILES: C[C@@H](O)c1nnc(CCNC(=O)c2cc(-c3ccccc3)on2)o1] | * |

TABLE 2-continued

| Compound | Structure | Ieq Activity | Ussing |
|---|---|---|---|
| A15 (Example 15) | 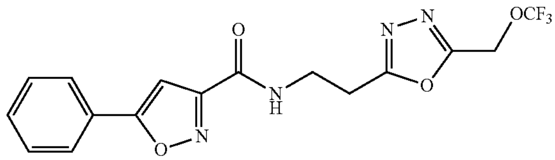 [SMILES: O=C(NCCc1nnc(COC(F)(F)F)o1)c1cc(-c2ccccc2)on1] | * | |
| A16 (Example 16) | 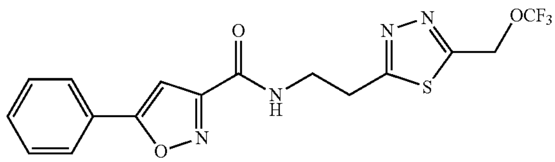 [SMILES: O=C(NCCc1nnc(COC(F)(F)F)s1)c1cc(-c2ccccc2)on1] | * | |
| A17 (Example 17) | 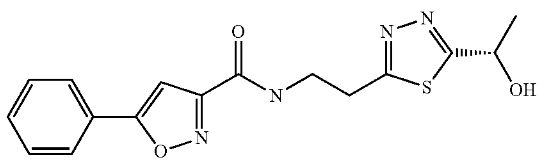 [SMILES: C[C@H](O)c1nnc(CCNC(=O)c2cc(-c3ccccc3)on2)s1] |  |  |
| A18 (Example 18) | 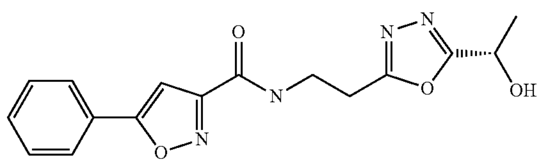 [SMILES: C[C@H](O)c1nnc(CCNC(=O)c2cc(-c3ccccc3)on2)o1] |  |  |
| A19 (Example 19) | 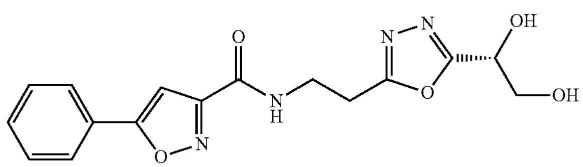 |  |  |
| A20 (Example 20) | 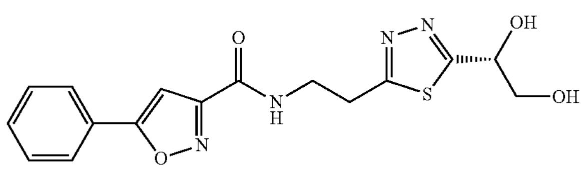 [SMILES: O=C(NCCc1nnc([C@H](O)CO)o1)c1cc(-c2ccccc2)on1] |  |  |
| A21 (Example 21) | 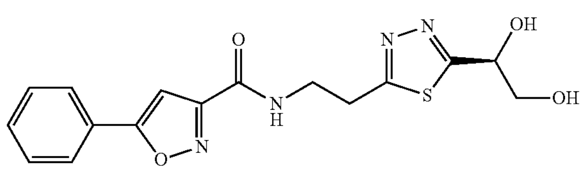 [SMILES: O=C(NCCc1nnc([C@@H](O)CO)s1)c1cc(-c2ccccc2)on1] |  |  |
| A22 (Example 22) | 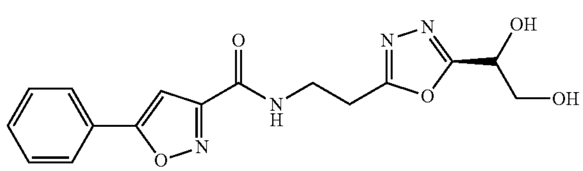 |  |  |
| A23 (Example 23) | 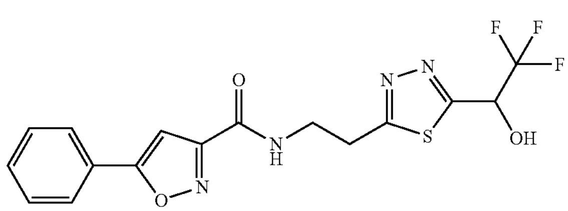 [SMILES: O=C(NCCc1nnc(C(O)C(F)(F)F)s1)c1cc(-c2ccccc2)on1] | ** | |

TABLE 2-continued

| Compound | Structure | Ieq Activity | Ussing |
|---|---|---|---|
| A24-a (Example 24) | 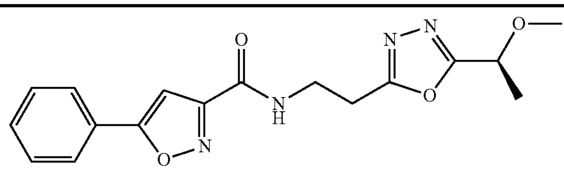 | | * |
| A24-b (Example 24) | 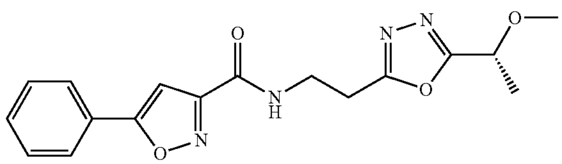 [SMILES: CO[C@H](C)c1nnc(CCNC(=O)c2cc(-c3ccccc3)on2)o1] | | * |
| A25-a (Example 25) | 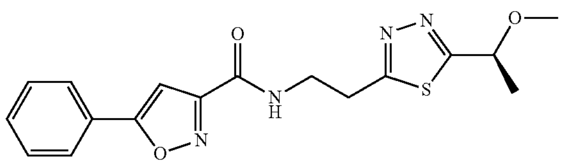 [SMILES: CO[C@@H](C)c1nnc(CCNC(=O)c2cc(-c3ccccc3)on2)s1] | | ** |
| A25-b (Example 25) | 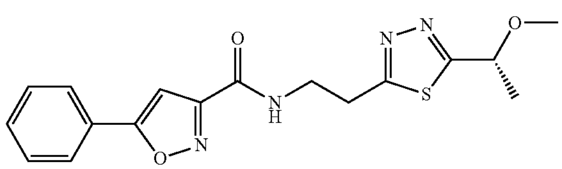 | | ** |

Example 27 i. Ussing Measurements

As discussed above, Ussing measurements can be used to measure CFTR activity. In this method, primary lung epithelial cells (hBEs) with a Cystic fibrosis causing class I mutation are differentiated for a minimum of 4 weeks in an air-liquid interface on SnapWell™ filter plates prior to the Ussing measurements. Cells are apically mucus-washed for 30 minutes prior to treatment with compounds. The basolateral media is removed and replaced with media containing the compound of interest diluted to its final concentration from DMSO or aqueous stocks. Treated cells are incubated at 37° C. and 5% $CO_2$ for 24 hours. At the end of the treatment period, the cells on filters are transferred to the Ussing chamber and equilibrated for 30 minutes. The short-circuit current is measured in voltage clamp-mode ($V_{hold}$=0 mV), and the entire assay is conducted at a temperature of 36° C.-36.5° C. Once the voltages stabilize, the chambers are clamped, and data are recorded by pulse readings every 5 seconds. Following baseline current stabilization, the following additions are applied and the changes in current and resistance of the cells are monitored:
1. Benzamil to the apical chamber to inhibit ENaC sodium channel.
2. Forskolin to both chambers to activate ΔF508-CFTR by phosphorylation.
3. Ivacaftor or Genistein to the apical chamber to potentiate ΔF508-CFTR channel opening.
4. CFTRinh-172 to the apical chamber to inhibit ΔF508-CFTR Cl-conductance.

The forskolin-sensitive current and inhibitable current (that potentiated current that is blocked by CFTRinh-172) are measured as the specific activity of the ΔF508-CFTR channel, and increase in response to compound in this activity over that observed in vehicle-treated samples are identified as the correction of ΔF508-CFTR function imparted by the compound tested.

Example 28 i. Ussing Measurements

As discussed above, Ussing measurements can be used to measure CFTR activity. In this method, primary lung epithelial cells (hBEs) with a Cystic Fibrosis-causing class III mutation are differentiated for a minimum of 4 weeks in an air-liquid interface on SnapWell™ filter plates prior to the Ussing measurements. Cells are apically mucus-washed for 30 minutes prior to treatment with compounds. The basolateral media is removed and replaced with media containing the compound of interest diluted to its final concentration from DMSO stocks. Treated cells are incubated at 37° C. and 5% $CO_2$ for 24 hours. At the end of the treatment period, the cells on filters are transferred to the Ussing chamber and equilibrated for 30 minutes. The short-circuit current is measured in voltage clamp-mode ($V_{hold}$=0 mV), and the entire assay is conducted at a temperature of 36° C.-36.5° C. Once the voltages stabilize, the chambers are clamped, and data is recorded by pulse readings every 5 seconds. Following baseline current stabilization, the following additions are applied and the changes in current and resistance of the cells is monitored:
1. Benzamil to the apical chamber to inhibit ENaC sodium channel.
2. Forskolin to both chambers to activate ΔF508-CFTR by phosphorylation.
3. VX-770 or Genistein to the apical chamber to potentiate ΔF508-CFTR channel opening.

4. CFTRinh-172 to the apical chamber to inhibit ΔF508-CFTR Cl-conductance.

The forskolin-sensitive current and inhibitable current (that potentiated current that is blocked by CFTRinh-172) are measured as the specific activity of the ΔF508-CFTR channel, and increase in response to compound in this activity over that observed in vehicle-treated samples are identified as the correction of ΔF508-CFTR function imparted by the compound tested.

Example 29 i. Ussing Measurements

As discussed above, Ussing measurements can be used to measure CFTR activity. In this method, primary lung epithelial cells (hBEs) with a Cystic Fibrosis-causing class V mutation are differentiated for a minimum of 4 weeks in an air-liquid interface on SnapWell™ filter plates prior to the Ussing measurements. Cells are apically mucus-washed for 30 minutes prior to treatment with compounds. The basolateral media is removed and replaced with media containing the compound of interest diluted to its final concentration from DMSO stocks. Treated cells are incubated at 37° C. and 5% $CO_2$ for 24 hours. At the end of the treatment period, the cells on filters are transferred to the Ussing chamber and equilibrated for 30 minutes. The short-circuit current is measured in voltage clamp-mode ($V_{hold}$=0 mV), and the entire assay is conducted at a temperature of 36° C.-36.5° C. Once the voltages stabilize, the chambers are clamped, and data is recorded by pulse readings every 5 seconds. Following baseline current stabilization, the following additions are applied and the changes in current and resistance of the cells is monitored:
1. Benzamil to the apical chamber to inhibit ENaC sodium channel.
2. Forskolin to both chambers to activate ΔF508-CFTR by phosphorylation.
3. VX-770 or Genistein to the apical chamber to potentiate ΔF508-CFTR channel opening.
4. CFTRinh-172 to the apical chamber to inhibit ΔF508-CFTR Cl-conductance.

The forskolin-sensitive current and inhibitable current (that potentiated current that is blocked by CFTRinh-172) are measured as the specific activity of the ΔF508-CFTR channel, and increases in response to compound in this activity over that observed in vehicle-treated samples are identified as the correction of ΔF508-CFTR function imparted by the compound tested.

ii. hBE Equivalent Current (Ieq) Assay

Primary lung epithelial cells homozygous for the Cystic Fibrosis-causing ΔF508 mutation are differentiated for a minimum of 4 weeks in an air-liquid interface on Costar 24 well HTS filter plates prior to the equivalent current (Ieq) measurements. Cells are apically mucus-washed for 30 minutes 24 h prior to treatment with compounds. The basolateral media is removed and replaced with media containing the compound of interest diluted to its final concentration from DMSO stocks. Treated cells are incubated at 37° C. and 5% $CO_2$ for 24 hours. At the end of the treatment period, the media is changed to the Ieq experimental solution for 30 minutes before the experiment and plates are maintained in a $CO_2$-free incubator during this period. The plates containing the cells are then placed in pre-warmed heating blocks at 36° C.±0.5 for 15 minutes before measurements are taken. The transepithelial voltage ($V_T$) and conductance ($G_T$) are measured using a custom 24 channel current clamp (TECC-24) with 24 well electrode manifold. The Ieq assay measurements are made following additions with standardized time periods:
1. The baseline $V_T$ and $G_T$ values are measured for approximately 20 minutes.
2. Benzamil is added to block ENaC for 15 minutes.
3. Forskolin plus VX-770 (ivacaftor) are added to maximally activate ΔF508-CFTR for 27 minutes.
4. Bumetanide is added to inhibit the $NaK_2Cl$ cotransporter and shut-off secretion of chloride.

The activity data captured is the area under the curve (AUC) for the traces of the equivalent chloride current. The AUC is collected from the time of the forskolin/VX-770 addition until the inhibition by bumetanide addition. Correction in response to compound treatment is scored as the increase in the AUC for compound-treated samples over that of vehicle-treated samples.

While this invention has been particularly shown and described with references to embodiments thereof, it will be understood by those skilled in the art that various changes in form and details may be made therein without departing from the scope of the invention encompassed by the appended claims.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A compound having the Formula (I):

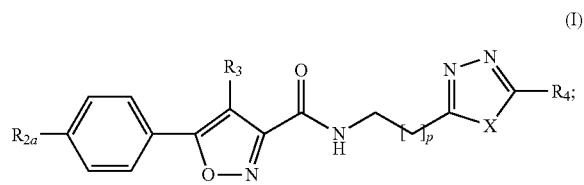

or a pharmaceutically acceptable salt, prodrug or solvate thereof, wherein:
X is oxygen or sulfur;
$R_{2a}$ is hydrogen or fluoro;
$R_3$ is hydrogen or fluoro;

$R_4$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $NR_d(COOR_c)$, $NR_dC(O)C(O)R_c$, $NR_dC(O)NR_dR_d$, $NR_dS(O)_n NR_dR_d$, $NR_dS(O)_nR_c$, $S(O)_nR_c$, $S(O)_nNR_dR_d$, $OC(O)OR_c$, $(C\!\!=\!\!NR_d)R_c$, optionally substituted heterocyclic and optionally substituted heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl;

each n is independently 0, 1 or 2; and p is 1 or 2;

provided that the compound is not N-[2-(5-phenyl-1,3,4-oxadiazol-2-yl)ethyl]-5-phenyl-3-isoxazolecarboxamide, N-[2-(5-methyl-1,3,4-thiadiazol-2-yl)ethyl]-5-phenyl-3-isoxazolecarboxamide, N-[2-(5-ethyl-1,3,4-thiadiazol-2-yl)ethyl]-5-phenyl-3-isoxazolecarboxamide, or N-(3-(5-amino-1,3,4-thiadiazol-2-yl)propyl)-5-phenylisoxazole-3-carboxamide.

2. The compound of claim 1, wherein $R_3$ is hydrogen.

3. The compound of claim 1 or 2, wherein $R_{2a}$ is hydrogen.

4. The compound of claim 1 or 2, wherein $R_{2a}$ is fluoro.

5. The compound of claim 1, wherein $R_4$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, halo, $OR_c$, $NR_dR_d$, $S(O)_nR_c$, $C(O)OR_c$, $NO_2$, CN and $C(O)R_c$.

6. The compound of claim 5, wherein $R_4$ is selected from the group consisting of optionally substituted $C_1$-$C_{10}$ alkyl, optionally substituted $C_3$-$C_{12}$ cycloalkyl, and $OR_j$, wherein $R_j$ is an optionally substituted $C_1$-$C_{10}$ alkyl.

7. The compound of claim 6, wherein $R_4$ is $C_1$-$C_4$ alkyl or $C_3$-$C_7$ cycloalkyl, where the $C_1$-$C_4$ alkyl and $C_3$-$C_7$ cycloalkyl are each optionally substituted with one or more groups selected from $OR_f$, $NR_gR_g$, and $SR_h$, wherein each of $R_f$ and $R_h$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; and each $R_g$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, optionally substituted heteroaryl; or alternatively, two geminal $R_g$ groups are taken together with the nitrogen atom to which they are attached to form an optionally substituted heterocyclic or an optionally substituted heteroaryl.

8. The compound of claim 7, wherein $R_4$ is $C_1$-$C_4$ alkyl optionally substituted with $OR_f$, wherein $R_f$ is selected from the group consisting of hydrogen, optionally substituted $C_1$-$C_{10}$ alkyl, and optionally substituted $C_3$-$C_{12}$ cycloalkyl.

9. The compound of claim 8, wherein $R_f$ is hydrogen.

10. The compound of claim 8, wherein $R_f$ is optionally substituted $C_1$-$C_4$ alkyl.

11. The compound of claim 5, wherein $R_4$ is a $C_1$-$C_4$ alkyl substituted with one or more halo, and optionally further substituted.

12. The compound of claim 11, wherein $R_4$ is a $C_1$-$C_4$ alkyl substituted with one or more fluoro, and optionally further substituted.

13. The compound of claim 1, wherein $R_4$ is:

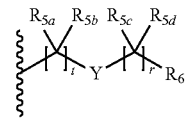

wherein $R_{5a}$, $R_{5b}$, $R_{5c}$, and $R_{5d}$ are each independently selected from the group consisting of hydrogen, optionally substituted $C_1$-$C_{10}$ alkyl and optionally substituted $C_3$-$C_{12}$ cycloalkyl; or alternatively, a geminal $R_{5a}$ and $R_{5b}$, or a geminal $R_{5c}$ and $R_{5d}$, can each independently be taken together with the carbon atom to which they are attached to form an optionally substituted $C_3$-$C_{12}$ cycloalkyl or an optionally substituted heterocyclic;

Y is O, S or $NR_i$;

t and r are each independently 0, 1, 2 or 3;

$R_6$ is selected from the group consisting of optionally substituted $C_1$-$C_{10}$ alkyl and optionally substituted $C_3$-$C_{12}$ cycloalkyl, optionally substituted heterocyclic, optionally substituted aryl, and optionally substituted heteroaryl; and $R_i$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl.

14. The compound of claim 1, wherein p is 1.

15. The compound of claim 1, wherein p is 2.

16. The compound of claim 1, wherein X is oxygen.

17. The compound of claim 1, wherein X is sulfur.

18. The compound of claim 1, wherein the compound is selected from the group consisting of:

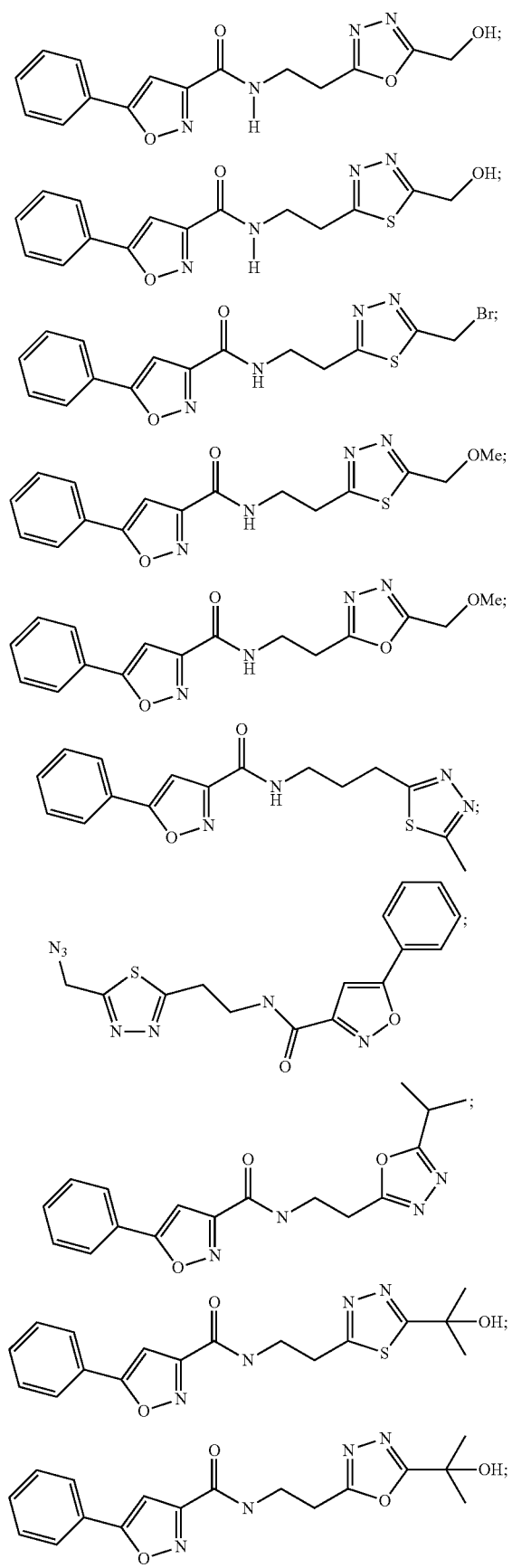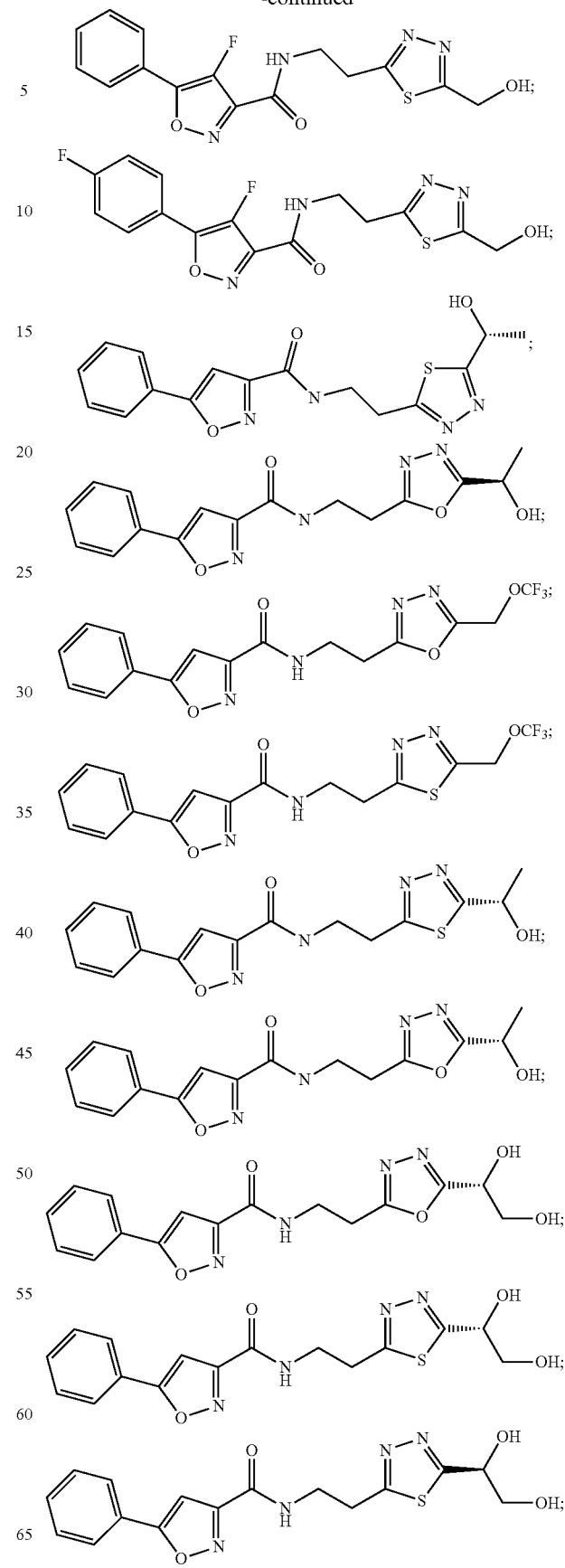

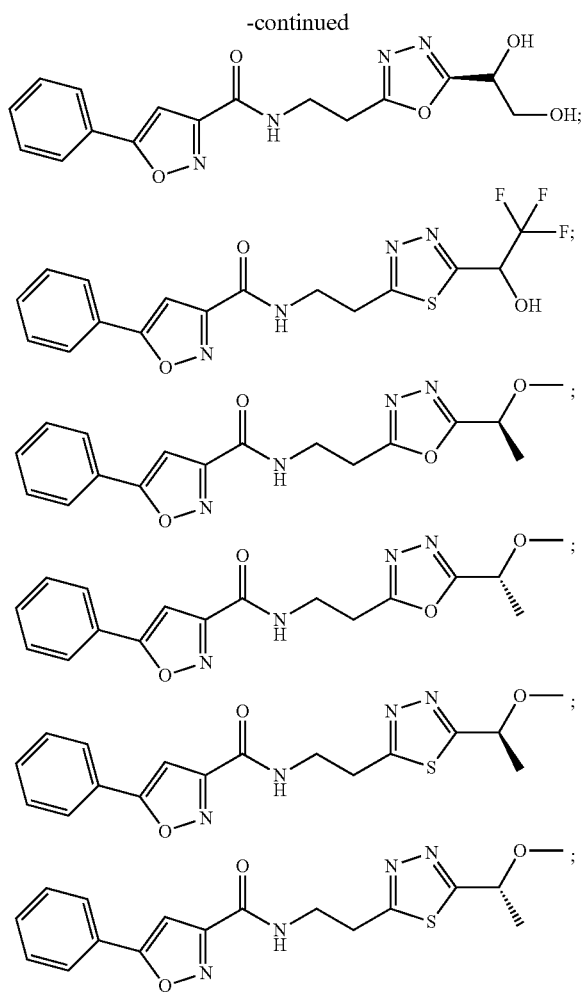

and a pharmaceutically acceptable salt thereof.

19. A pharmaceutical composition comprising a compound of claim 1 and a pharmaceutically acceptable carrier or excipient.

20. A method of enhancing cystic fibrosis transmembrane conductance regulator (CFTR) activity in a subject in need thereof comprising: administering to said subject an effective amount of a compound of claim 1, or a pharmaceutical composition of claim 19.

21. The method of claim 20, wherein the activity of a mutant CFTR is enhanced.

22. The method of claim 21, wherein ΔF508 CFTR activity is enhanced.

23. The method of claim 20, wherein the subject is suffering from a disease associated with decreased CFTR activity.

24. The method of claim 23, wherein the disease is cystic fibrosis.

25. The method of claim 24, wherein the subject is a human patient.

26. A method of treating a patient suffering from cystic fibrosis comprising administering to said patient an effective amount of a compound of claim 1, or a pharmaceutical composition of claim 19.

27. The method of claim 20, further comprising administering an additional therapeutic agent.

28. The method of claim 27, wherein at least two additional therapeutic agents are administered.

29. The method of claim 27, wherein at least one additional therapeutic agent is a CFTR corrector or potentiator.

30. The method of claim 29, wherein each CFTR corrector or potentiator is independently selected from the group consisting of VX-770 (Ivacaftor), VX-809 (3-(6-(1-(2,2-difluorobenzo[d][1,3]dioxol-5-yl)cyclopropanecarboxamido)-3-methylpyridin-2-yl)benzoic acid, VX661 ((R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropane-1-carboxamide), GLPG -2222, and GLPG-1837.

31. A pharmaceutical composition comprising a pharmaceutically acceptable carrier or excipient and a compound having the Formula (I):

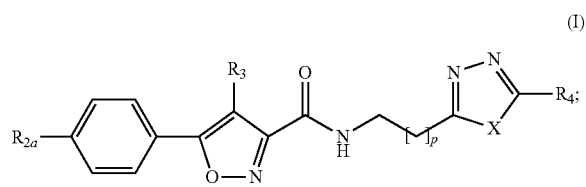

or a pharmaceutically acceptable salt, prodrug or solvate thereof, wherein:

X is oxygen or sulfur;

$R_{2a}$ is hydrogen or fluoro;

$R_3$ is hydrogen or fluoro;

$R_4$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, optionally substituted heterocyclic and optionally substituted heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl;

each n is independently 0, 1 or 2; and p is 1 or 2;

provided that the compound is not N-[2-(5-ethyl-1,3,4-thiadiazol-2-yl)ethyl]-5-phenyl-3-isoxazolecarboxamide.

32. A method of enhancing cystic fibrosis transmembrane conductance regulator (CFTR) activity in a subject in need thereof comprising administering to said subject an effective amount of a compound having the Formula (I):

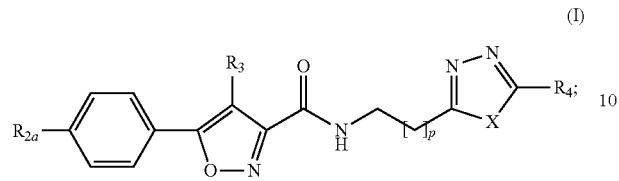

or a pharmaceutically acceptable salt, prodrug or solvate thereof, wherein:
X is oxygen or sulfur;
$R_{2a}$ is hydrogen or fluoro;
$R_3$ is hydrogen or fluoro;
$R_4$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$cycloalkenyl, optionally substituted aryl, halo, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_n R_c$, $N(R_d)(COOR_c)$, $NR_dC(O)C(O)R_c$, $NR_dC(O)NR_dR_d$, $NR_dS(O)_n NR_dR_d$, $NR_dS(O)_n R_c$, $S(O)_n R_c$, $S(O)_n NR_dR_d$, $OC(O)OR_c$, $(C=NR_d)R_c$, optionally substituted heterocyclic and optionally substituted heteroaryl;
each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl;
each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl and optionally substituted heteroaryl; or two geminal $R_d$ groups are taken together with the nitrogen atom to which they are attached to form an optionally substituted heterocyclic or an optionally substituted heteroaryl;
each n is independently 0, 1 or 2; and
p is 1 or 2;
provided that the compound is not N-[2-(5-ethyl-1,3,4-thiadiazol-2-yl)ethyl]-5-phenyl-3-isoxazolecarboxamide.

33. A compound represented by formula (II):

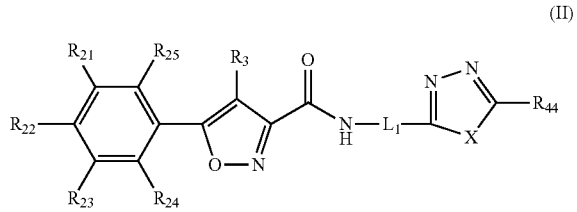

or a pharmaceutically acceptable salt, prodrug or solvate thereof, wherein:
X is oxygen or sulfur;
$R_{21}$, $R_{22}$, $R_{23}$, $R_{24}$, and $R_{25}$ are each independently selected from hydrogen or fluoro;
$R_3$ is hydrogen or fluoro;
$L_1$ is $C_{2-3}$alkylene, optionally substituted by one, two or three substituents selected from the group consisting of halogen, hydroxyl, $C_{1-3}$alkyl (optionally substituted by one, two or three substituents each selected independently from $R_{ff}$);
$R_{44}$ is selected from the group consisting of halogen, hydroxyl, $C_{1-6}$alkyl, $C_{1-6}$alkoxy, $C_{2-6}$alkenyl, $C_{2-6}$alkynyl, and $C_{3-7}$cycloalkyl, wherein $C_{1-6}$alkyl is substituted by one, two or three substituents each independently selected from $R_{gg}$, and each of $C_{1-6}$alkoxy, $C_{2-6}$alkenyl, $C_{2-6}$alkynyl, and $C_{3-7}$cycloalkyl may be optionally substituted by one, two or three substituents each independently selected from $R_{gg}$;
$R_{gg}$ is selected from the group consisting of halogen, $C_{1-6}$alkyl, $C_{1-6}$alkoxy, hydroxyl, C(O)OH, —C(O)OC$_{1-6}$alkyl, —O—C$_{3-6}$cycloalkyl, —O-heterocycle, —O-heteroaryl, —O-phenyl, CN, $N_3$, —NR'R", —NR'—S(O)$_w$—C$_{1-3}$alkyl, S(O)$_w$—NR'R", and —S(O)$_w$—C$_{1-3}$alkyl, where w is 0, 1, or 2;
$R_{ff}$ is selected for each occurrence from group consisting of halogen, hydroxyl, $C_{1-4}$alkyl, $C_{1-4}$alkoxy, $C_{2-4}$alkenyl, $C_{3-6}$cycloalkyl, —NR'R", —NR'—S(O)$_w$—C$_{1-3}$alkyl, S(O)$_w$—NR'R", and —S(O)$_w$—C$_{1-3}$alkyl, where w is 0, 1, or 2, wherein $C_{1-4}$alkyl, $C_{1-4}$alkyoxy, $C_{2-4}$alkenyl and $C_{3-6}$cycloalkyl may be optionally substituted by one, two or three substituents each independently selected from the group consisting of halogen, hydroxyl, —NR'R", —NR'—S(O)$_w$—C$_{1-3}$alkyl, S(O)$_w$—NR'R", and —S(O)$_w$—C$_{1-3}$alkyl; and
R' and R" are each independently selected for each occurrence from H and $C_{1-4}$alkyl or taken together with the nitrogen to which they are attached form a heterocyclic ring.

34. The compound of claim 33, wherein $R_{44}$ is $C_{1-6}$alkyl substituted by one, two or three substituents each independently selected from $R_{gg}$.

35. The compound of claim 33, wherein $R_{44}$ is methyl substituted by one, two or three substituents each selected from halogen, CN, $N_3$, hydroxyl, methoxy and ethoxy, ethyl substituted by one, two or three substituents each selected from halogen, hydroxyl, CN, $N_3$, methoxy and ethoxy, propyl substituted by one, two or three substituents each selected from halogen, CN, $N_3$, hydroxyl, methoxy and ethoxy, isopropyl substituted by one, two or three substituents each selected from halogen, hydroxyl, CN, $N_3$, methoxy and ethoxy, n-butyl substituted by one, two or three substituents each selected from halogen, CN, $N_3$,hydroxyl, methoxy and ethoxy, t-butyl substituted by one, two or three substituents each selected from halogen, CN, $N_3$, hydroxyl, methoxy and ethoxy, s- butyl substituted by one, two or three substituents each selected from halogen, CN, $N_3$, hydroxyl, methoxy and ethoxy and isobutyl substituted by one, two or three substituents each selected from halogen, CN, $N_3$, hydroxyl, methoxy and ethoxy.

36. The compound of claim 33, wherein $R_{44}$ is substituted on a primary, secondary, and/or tertiary carbon.

37. A pharmaceutical composition comprising a compound of claim 33 and a pharmaceutically acceptable excipient.

38. A method of treating a patient suffering from cystic fibrosis comprising administering to said patient an effective amount of a compound of claim 33, or a pharmaceutical composition of claim 37.

* * * * *